United States Patent
Rader et al.

(10) Patent No.: US 11,242,388 B2
(45) Date of Patent: *Feb. 8, 2022

(54) ROR1 ANTIBODY COMPOSITIONS AND RELATED METHODS

(71) Applicants: NBE-Therapeutics AG, Basel (CH); The Scripps Research Institute, La Jolla, CA (US)

(72) Inventors: Christoph Rader, Jupiter, FL (US); Haiyong Peng, Jupiter, FL (US); Roger Beerli, Adlikon (CH); Lorenz Waldmeier, Basel (CH); Ulf Grawunder, Hersberg (CH)

(73) Assignees: NBE-Therapeutics AG, Basel (CH); The Scripps Research Institute, La Jolla, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/805,102

(22) Filed: Feb. 28, 2020

(65) Prior Publication Data

US 2020/0299381 A1 Sep. 24, 2020

Related U.S. Application Data

(63) Continuation of application No. 16/040,244, filed on Jul. 19, 2018, now Pat. No. 10,618,959, which is a continuation of application No. PCT/US2017/014311, filed on Jan. 20, 2017.

(60) Provisional application No. 62/280,843, filed on Jan. 20, 2016.

(51) Int. Cl.
| | |
|---|---|
| C07K 16/28 | (2006.01) |
| A61K 39/395 | (2006.01) |
| A61K 47/68 | (2017.01) |
| C07K 14/725 | (2006.01) |
| A61K 47/69 | (2017.01) |
| C07K 14/705 | (2006.01) |
| C12N 9/12 | (2006.01) |
| A61P 35/02 | (2006.01) |
| A61P 35/00 | (2006.01) |
| A61K 39/00 | (2006.01) |

(52) U.S. Cl.
CPC ...... *C07K 16/2803* (2013.01); *A61K 47/6809* (2017.08); *A61K 47/6849* (2017.08); *A61K 47/6889* (2017.08); *A61K 47/6903* (2017.08); *A61P 35/00* (2018.01); *A61P 35/02* (2018.01); *C07K 14/705* (2013.01); *C07K 14/7051* (2013.01); *C12N 9/12* (2013.01); *C12Y 207/10001* (2013.01); *A61K 2039/505* (2013.01); *C07K 2317/24* (2013.01); *C07K 2317/33* (2013.01); *C07K 2317/73* (2013.01); *C07K 2317/90* (2013.01); *C07K 2317/92* (2013.01); *C07K 2319/00* (2013.01); *C07K 2319/02* (2013.01); *C07K 2319/03* (2013.01)

(58) Field of Classification Search
None
See application file for complete search history.

(56) References Cited

U.S. PATENT DOCUMENTS

| | | |
|---|---|---|
| 7,462,608 B2 | 12/2008 | Chen et al. |
| 8,212,009 B2 | 7/2012 | Kipps et al. |
| 8,703,801 B2 | 4/2014 | Nair et al. |
| 9,150,647 B2 | 10/2015 | Mellstedt et al. |
| 9,163,258 B2 | 10/2015 | Riddell et al. |
| 9,228,023 B2 | 1/2016 | Rohlff et al. |
| 9,242,014 B2 | 1/2016 | Kipps et al. |
| 9,266,952 B2 | 2/2016 | Teige |
| 9,316,646 B2 | 4/2016 | Rader et al. |
| 9,758,586 B2 | 9/2017 | Rader et al. |
| 9,933,434 B2 | 4/2018 | Kipps et al. |
| 9,938,350 B2 | 4/2018 | Kipps et al. |
| 10,041,090 B2 | 8/2018 | Gao et al. |
| 10,618,959 B2* | 4/2020 | Rader .......... C07K 14/705 |
| 2003/0113762 A1 | 6/2003 | Warrington et al. |
| 2008/0318212 A1 | 12/2008 | Wilson et al. |
| 2011/0008347 A1 | 1/2011 | Ullrich et al. |
| 2012/0058051 A1 | 3/2012 | Rader et al. |
| 2012/0219506 A1 | 8/2012 | Moore et al. |
| 2012/0282177 A1 | 11/2012 | Rohlff et al. |
| 2013/0131139 A1 | 5/2013 | Tyner et al. |
| 2013/0251723 A1 | 9/2013 | Rohlff et al. |

(Continued)

FOREIGN PATENT DOCUMENTS

| | | |
|---|---|---|
| EP | 2649098 B2 | 11/2017 |
| WO | 2007146957 A2 | 12/2007 |

(Continued)

OTHER PUBLICATIONS

Karvonen et al., Targeting ROR1 identifies new treatment strategies in hematological cancers, Apr. 13, 2017, Biochemical Society Transactions 45:457-464 (Year: 2017).

(Continued)

*Primary Examiner* — Robert C Hayes

(74) *Attorney, Agent, or Firm* — Morgan, Lewis & Bockius LLP; Christopher J. Betti; Alia M. Orbin

(57) ABSTRACT

The invention provides antibodies, antibody drug conjugates, antibody-based fragments or antibody fragments (antigen-binding fragments), as well as antibody drug conjugates (ADCs) and chimeric antigen receptors (CARs), that specifically recognize human ROR1 and related compositions. Also provided in the invention are methods of using such antibodies in various diagnostic and therapeutic applications.

12 Claims, 29 Drawing Sheets

Specification includes a Sequence Listing.

(56) References Cited

U.S. PATENT DOCUMENTS

| | | |
|---|---|---|
| 2013/0273073 A1 | 10/2013 | Kipps et al. |
| 2013/0281922 A1 | 10/2013 | Teige |
| 2014/0004156 A1 | 2/2014 | Mellstedt et al. |
| 2015/0258143 A1 | 9/2015 | Malarkannan |
| 2015/0306141 A1 | 10/2015 | Jensen et al. |
| 2016/0297881 A1 | 10/2016 | Vu et al. |
| 2016/0362472 A1 | 12/2016 | Bitter et al. |
| 2017/0015746 A1 | 1/2017 | Jensen |
| 2017/0029774 A1 | 2/2017 | Jensen et al. |
| 2017/0051252 A1 | 2/2017 | Morgan et al. |
| 2017/0152297 A1 | 6/2017 | Jensen |
| 2017/0198045 A1 | 7/2017 | Johnson et al. |
| 2017/0204176 A1 | 7/2017 | Bonvini et al. |
| 2017/0210799 A1 | 7/2017 | Anderson et al. |
| 2017/0226183 A1 | 8/2017 | Schiffer-Mannioui |
| 2017/0233472 A1 | 8/2017 | Barat et al. |
| 2017/0246279 A1 | 8/2017 | Berger et al. |
| 2017/0267742 A1 | 9/2017 | Jensen et al. |
| 2017/0275374 A1 | 9/2017 | Schiffer-Mannioui |
| 2017/0283497 A1 | 10/2017 | Schiffer-Mannioui |
| 2017/0306018 A1 | 10/2017 | Vu et al. |
| 2017/0306044 A1 | 10/2017 | Vu et al. |
| 2017/0335281 A1 | 11/2017 | Loew et al. |
| 2017/0363630 A1 | 12/2017 | Petricoin et al. |
| 2018/0009891 A1 | 2/2018 | Jensen |
| 2018/0066063 A1 | 3/2018 | Kipps et al. |
| 2018/0112002 A1 | 4/2018 | Kipps et al. |
| 2018/0127503 A1 | 5/2018 | Liu et al. |
| 2018/0142016 A1 | 5/2018 | Wong et al. |
| 2018/0147271 A1 | 5/2018 | Morgan et al. |
| 2019/0040132 A1 | 2/2019 | Balakrishnan et al. |
| 2019/0153092 A1 | 5/2019 | Waldmeier et al. |

FOREIGN PATENT DOCUMENTS

| | | |
|---|---|---|
| WO | 2008076868 A2 | 6/2008 |
| WO | 2008103849 A2 | 8/2008 |
| WO | 2009099741 A1 | 8/2009 |
| WO | 2010016634 A2 | 2/2010 |
| WO | 2012073217 A1 | 6/2012 |
| WO | 2014013026 A1 | 1/2014 |
| WO | 2014140317 A2 | 9/2014 |
| WO | 2015113110 A1 | 8/2015 |
| WO | 2016094873 A2 | 6/2016 |
| WO | 2016102679 A1 | 6/2016 |
| WO | 2017053469 A2 | 3/2017 |
| WO | 2017107541 A1 | 6/2017 |

OTHER PUBLICATIONS

Masiakowski and Carroll, J Biol Chem. (1992), 267 (36):26181-26190.
Mackeigan et al., Nat Cell Biol. (2005), DOI: 10.1038/ncb1258:1-10.
Basker et al., Clin Cancer Res. (2008), 14(2):396-404.
Fukuda et al., PNAS. (2008), 105(8):3047-3052.
Daneshmanesh et al. Int. J. Cancer (2008), 123: 1190-1195.
Tyner et al., PNAS (2009), 106(21):8695-8700.
Daneshmanesh et al., Leukemia. (2012), 26:1348-1355.
Baskar et al., mAbs. (2012), 4:3, 349-361.
Patterson et al., Bioconjugate Chemistry 25:1402, 2014.
Choi et al., Clinical Lymphoma Myeloma and leukemia 15:S167, 2015.
Peng et al., J Mal Biol. 429, 2954-2973, 2017.
Balakrishnan et al. (Nov. 16, 2016) "Analysis of ROR1 Protein Expression in Human Cancer and Normal Tissues", Clinical Cancer Research 23:3061-3071 doi: 10.1158/1078-0432.
Beerli, R. et al. (Jul. 1, 2015) "Sortase Enzyme-Mediated Generation of Site-Specifically Conjugated Antibody Drug Conjugates with High In Vitro and In Vivo Potency", PLOS One e0131177.
Berger et al. (Feb. 2015) "Safety of Targeting ROR1 in Primates with Chimeric Antigen Receptor-Modified T Cells", Cancer Immunol. Res. 3(2):206-216 doi: 10.1158/2326-6066.CIR-14-0163.
Cui et al. (Dec. 22, 2016) "High-level ROR1 Associates with Accelerated Disease Progression in Chronic Lymphocytic Leukemia", Blood 128(25):2931-2940.
Hudecek et al. (Apr. 25, 2013) "Receptor Affinity and Extracellular Domain Modifications Affect Tumor Recognition by ROR1-Specific Chimeric Antigen Receptor T Cells", Clinical Cancer Res; 19(12):3153-3164 doi: 10.1158/1078-0432.CCR-13-0330.
International Search Report with Written Opinion corresponding to International Patent Application No. PCT/EP2016/076244, dated Mar. 27, 2017 (19 pages).
Quintieri et al. (Feb. 15, 2005) "Formation and Antitumor Activity of PNU-159682, A Major Metabolite of Nemorubicin in Human Liver Microsomes", Clinical Cancer Research, 11(4):1608-1617.
Rebagay et al. (Apr. 18, 2012) "ROR1 and ROR2 in Human Malignancies: Potentials for Targeted Therapy", Frontiers in Oncology 2(34):1-8 doi: 10.3389/fonc.2012.00034.
Shabani et al. (2015) "Receptor Tyrosine Kinase-Like Orphan Receptor 1: A Novel Target for Cancer Immunotherapy" Expert Opin. Ther. Targets 19(7):1-15.
Spirig et al. (Nov. 7, 2011) "Sortase Enzymes in Gram-Positive Bacteria", Molecular Microbiology, 82(5), 1044-1059 doi: 10.1111/j.1365-2958.2011.07887.x.
Ulf Grawunder (Feb. 2016) "Development of Best-In-Class, Homogeneous Antibody Drug Conjugates (ADCs) for Highly Effective and Safer Cancer Therapy", NBE-Therapeutics AG, (25 pages).
A.T. Fiyas et al., "Chronic Lymphocytic Leukemia: Diagnostics and Treatment", Department of Hospital Therapy, EE Grodno State Medical University, pp. 93-97 with English Translation (16 pages).
Hudecek et al., "The B-cell Tumor-Associated Antigen ROR1 Can Be Targeted With T Cells Modified to Express a ROR1-Specific Shimeric Antigen Receptor," Blood 116:4532-4541 (2010).

* cited by examiner

| ADC clone | T20 score HC | T20 score LC | $K_{on}$ ($10^4 M^{-1} s^{-1}$) | $K_{off}$ ($10^{-3} s^{-1}$) | $K_D$ (nM) |
|---|---|---|---|---|---|
| XBR1-402*1 | 80.64 | 78.85 | 116 | 5.91 | 5.1 |
| XBR1-402*1 | 80.64 | 78.85 | 110 | 5.56 | 5.1 |
| huXBR1-402-3 | 80.34 | 88.26 | 119 | 3.75 | 3.2 |
| huXBR1-402-8 | 81.20 | 82.75 | 129 | 2.76 | 2.1 |
| huXBR1-402-15 | 81.20 | 91.15 | 111 | 3.94 | 3.5 |
| huXBR1-402-17 | 80.34 | 91.15 | 96 | 3.22 | 3.4 |
| huXBR1-402-19 | 80.30 | 91.15 | 111 | 3.32 | 3.0 |
| huXBR1-402-26 | 80.30 | 86.56 | 105 | 3.28 | 3.1 |

*1: two independent measurements

FIG. 24

```
                         SEQUENCE LISTING

<160> NUMBER OF SEQ ID NOS: 163

<210> SEQ ID NO 1
    <211> LENGTH: 117
    <212> TYPE: PRT
    <213> ORGANISM: Oryctolagus cuniculus

<400> SEQUENCE: 1

Gln Glu Gln Gln Lys Glu Ser Gly Gly Gly Leu Phe Lys Pro Thr Asp
    1               5                   10                  15

Thr Leu Thr Leu Thr Cys Thr Ala Ser Gly Phe Asp Ile Ser Ser Tyr
                20                  25                  30

Tyr Met Ser Trp Val Arg Gln Ala Pro Gly Asn Gly Leu Glu Trp Ile
                35                  40                  45

Gly Ala Ile Gly Ile Ser Gly Asn Ala Tyr Tyr Ala Ser Trp Ala Lys
            50                  55                  60

Ser Arg Ser Thr Ile Thr Arg Asn Thr Asn Leu Asn Thr Val Thr Leu
    65                  70                  75                  80

Lys Met Thr Ser Leu Thr Ala Ala Asp Thr Ala Thr Tyr Phe Cys Ala
                85                  90                  95

Arg Asp His Pro Thr Tyr Gly Met Asp Leu Trp Gly Pro Gly Thr Leu
                    100                 105                 110

Val Thr Val Ser Ser
            115

<210> SEQ ID NO 2
    <211> LENGTH: 118
    <212> TYPE: PRT
    <213> ORGANISM: Oryctolagus cuniculus

<400> SEQUENCE: 2

Gln Glu Gln Leu Glu Glu Ser Gly Gly Gly Leu Val Thr Pro Gly Gly
    1               5                   10                  15

Ser Leu Thr Leu Thr Cys Thr Ala Ser Gly Phe Thr Ile Ser Thr Tyr
                20                  25                  30

His Met Ser Trp Val Arg Gln Ala Pro Gly Lys Gly Leu Glu Trp Ile
                35                  40                  45

Gly Ser Ile Tyr Ala Gly Ser Gly Ser Thr Tyr Tyr Ala Ser Trp Val
            50                  55                  60

Asn Gly Arg Phe Thr Ile Ser Ser Asn Thr Thr Gln Asn Thr Val Ser
    65                  70                  75                  80

Leu Gln Met Asn Ser Leu Thr Val Ala Asp Thr Ala Thr Tyr Phe Cys
                85                  90                  95

Ala Arg Asp His Pro Ser Tyr Gly Met Asp Leu Trp Gly Pro Gly Thr
                    100                 105                 110

Leu Val Thr Val Ser Ser
```

<210> SEQ ID NO 3
<211> LENGTH: 125
<212> TYPE: PRT
<213> ORGANISM: Oryctolagus cuniculus

<400> SEQUENCE: 3

Gln Glu Gln Leu Lys Glu Ser Gly Gly Gly Leu Val Gln Pro Gly Gly
1               5                   10                  15

Ser Leu Lys Leu Ser Cys Lys Ala Ser Gly Phe Asp Leu Ser Asn Tyr
            20                  25                  30

Gly Val Ser Trp Val Arg Gln Ala Pro Gly Lys Gly Leu Glu Trp Ile
        35                  40                  45

Gly Tyr Ile Asp Pro Thr Phe Asp Tyr Thr Tyr Tyr Ala Ser Trp Val
    50                  55                  60

Asn Gly Arg Phe Ser Ile Ser Arg Glu Asn Thr Gln Asn Thr Val Ser
65                  70                  75                  80

Leu Gln Ile Asn Ser Leu Thr Pro Ala Asp Thr Ala Thr Tyr Phe Cys
                85                  90                  95

Ala Arg Trp Val Tyr Gly Val Asp Asp Tyr Gly Asp Gly Asn Trp Leu
            100                 105                 110

Asp Leu Trp Gly Gln Gly Thr Leu Val Thr Ile Ser Ser
        115                 120                 125

<210> SEQ ID NO 4
<211> LENGTH: 117
<212> TYPE: PRT
<213> ORGANISM: Oryctolagus cuniculus

<400> SEQUENCE: 4

Gln Glu Gln Leu Glu Glu Ser Gly Gly Arg Leu Val Thr Pro Gly Thr
1               5                   10                  15

Pro Leu Thr Leu Thr Cys Thr Ala Ser Gly Phe Phe Leu Ser Ser Tyr
            20                  25                  30

Tyr Val Ser Trp Val Arg Gln Ala Pro Gly Lys Gly Leu Glu Trp Ile
        35                  40                  45

Gly Ala Ile Gly Thr Gly Gly Ser Ala Tyr Tyr Ala Ser Trp Ala Lys
    50                  55                  60

Ser Arg Ser Thr Ile Thr Arg Asn Thr Asn Leu Ser Thr Val Thr Leu
65                  70                  75                  80

Lys Met Thr Ser Leu Thr Ala Ala Asp Thr Ala Thr Tyr Phe Cys Ala
                85                  90                  95

Arg Asp His Pro Asn Tyr Gly Met Asp Leu Trp Gly Pro Gly Thr Leu
            100                 105                 110

Val Thr Val Ser Ser
        115

<210> SEQ ID NO 5
<211> LENGTH: 113
<212> TYPE: PRT
<213> ORGANISM: Oryctolagus cuniculus

<400> SEQUENCE: 5

Gln Ser Leu Glu Glu Ser Gly Gly Gly Leu Val Gln Pro Gly Glu Ser
1               5                   10                  15

Leu Thr Leu Thr Cys Thr Val Ser Gly Phe Ser Leu Ser Arg Asn Gly
            20                  25                  30

```
Met Thr Trp Val Arg Gln Ala Pro Gly Lys Gly Leu Glu Trp Ile Gly
         35                  40                  45

Ile Ile Thr Ser Ser Gly Asp Lys Tyr Tyr Ala Thr Trp Ala Lys Gly
 50                  55                  60

Arg Phe Thr Ile Ser Lys Thr Ser Ser Thr Thr Val Asp Leu Lys Met
 65                  70                  75                  80

Thr Ser Leu Thr Thr Glu Asp Thr Ala Thr Tyr Phe Cys Ala Arg Gly
                 85                  90                  95

Thr Val Ser Ser Asp Ile Trp Gly Pro Gly Thr Leu Val Thr Ile Ser
                100                 105                 110

Ser
```

```
<210> SEQ ID NO 6
<211> LENGTH: 115
<212> TYPE: PRT
<213> ORGANISM: Oryctolagus cuniculus

<400> SEQUENCE: 6

Gln Glu Gln Leu Lys Glu Ser Gly Arg Gly Leu Val Gln Pro Gly Gly
 1               5                   10                  15

Ser Leu Lys Leu Ser Cys Lys Ala Ser Gly Phe Asp Phe Ser Gly Trp
                 20                  25                  30

Tyr Met Thr Trp Val Arg Gln Ala Pro Gly Lys Gly Leu Glu Trp Ile
             35                  40                  45

Gly Thr Ile Gly Thr Thr Lys Gly Arg Thr Tyr Tyr Ala Ser Trp Val
         50                  55                  60

Asn Gly Arg Phe Thr Ile Ser Ser Asn Ala Gln Asn Thr Val Asp Leu
 65                  70                  75                  80

Gln Met Asn Ser Leu Thr Ala Ala Asp Arg Ala Thr Tyr Phe Cys Val
                 85                  90                  95

Arg Gly Ser Asp Tyr Phe Asp Leu Trp Gly Pro Gly Thr Leu Val Thr
                100                 105                 110

Ile Ser Ser
        115
```

```
<210> SEQ ID NO 7
<211> LENGTH: 120
<212> TYPE: PRT
<213> ORGANISM: Oryctolagus cuniculus

<400> SEQUENCE: 7

Gln Glu Gln Leu Val Glu Ser Gly Gly Arg Leu Val Thr Pro Gly Gly
 1               5                   10                  15

Ser Leu Thr Leu Thr Cys Thr Ala Ser Gly Phe Ser Leu Ser Ser Tyr
                 20                  25                  30

Tyr Met Gly Trp Val Arg Gln Ala Pro Gly Lys Gly Leu Glu Trp Ile
             35                  40                  45

Gly Thr Ile Tyr Gly Gly Ser Gly Ser Thr Trp Tyr Ala Ser Trp Val
         50                  55                  60

Lys Gly Arg Phe Thr Ile Ser Lys Thr Ser Thr Ala Val Asp Leu Lys
 65                  70                  75                  80

Ile Thr Ser Leu Thr Thr Glu Asp Thr Ala Thr Tyr Phe Cys Ala Arg
                 85                  90                  95

Ser Tyr Pro Gly Trp Thr Thr Gly Pro Tyr Phe Asp Ile Trp Gly Pro
                100                 105                 110
```

```
Gly Thr Leu Val Thr Val Ser Ser
        115                 120

<210> SEQ ID NO 8
<211> LENGTH: 121
<212> TYPE: PRT
<213> ORGANISM: Oryctolagus cuniculus

<400> SEQUENCE: 8

Gln Ser Val Glu Glu Ser Gly Gly Arg Leu Val Thr Pro Gly Thr Pro
1               5                   10                  15

Leu Thr Leu Thr Cys Thr Ala Ser Gly Ile Asp Leu Ser Arg Tyr Ala
            20                  25                  30

Val Asn Trp Val Arg Gln Ala Pro Gly Lys Gly Leu Glu Trp Ile Gly
        35                  40                  45

Val Ile Ser Gly Ser Gly Thr Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Gly Trp
                85                  90                  95

Ala Thr Asp Gly Ile Phe Asp Tyr Asp Asp Thr Phe Asn Leu Trp Gly
            100                 105                 110

Pro Gly Thr Leu Val Thr Val Ser Ser
        115                 120

<210> SEQ ID NO 9
<211> LENGTH: 115
<212> TYPE: PRT
<213> ORGANISM: Oryctolagus cuniculus

<400> SEQUENCE: 9

Gln Glu Gln Leu Val Glu Ser Gly Gly Arg Leu Val Thr Pro Gly Gly
1               5                   10                  15

Ser Leu Thr Leu Thr Cys Ala Ala Ser Gly Phe Ser Pro Ser Ser Tyr
            20                  25                  30

Trp Met Ser Trp Val Arg Gln Ala Pro Gly Lys Gly Leu Glu Trp Ile
        35                  40                  45

Gly Ala Ile Tyr Val Asp Ser Gly Ser Ala Tyr Tyr Ala Ser Trp Ala
    50                  55                  60

Lys Ser Arg Phe Thr Ile Ser Lys Thr Ser Thr Thr Val Asp Leu
65                  70                  75                  80

Lys Met Thr Ser Leu Thr Thr Glu Asp Thr Ala Ile Tyr Phe Cys Ala
                85                  90                  95

Arg Asp Gly Trp Gly Ser Asp Val Trp Gly Pro Gly Thr Leu Val Thr
            100                 105                 110

Ile Ser Ser
        115

<210> SEQ ID NO 10
<211> LENGTH: 113
<212> TYPE: PRT
<213> ORGANISM: Oryctolagus cuniculus

<400> SEQUENCE: 10

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Tyr
```

```
                20                  25                  30
Met Ser Trp Val Arg Gln Ala Pro Gly Lys Gly Leu Glu Trp Ile Gly
            35                  40                  45

Thr Ile Ser Ser Ser Gly Ser Thr Tyr Tyr Ala Ser Trp Val Lys Gly
    50                  55                  60

Arg Phe Thr Ile Ser Lys Thr Ser Thr Thr Val Asp Leu Lys Met Thr
65                  70                  75                  80

Ser Leu Thr Thr Glu Asp Thr Ala Thr Tyr Phe Cys Ala Arg Asp Leu
                85                  90                  95

Asp Tyr Asp Met Asp Leu Trp Gly Pro Gly Thr Leu Val Thr Val Ser
            100                 105                 110

Ser

<210> SEQ ID NO 11
<211> LENGTH: 117
<212> TYPE: PRT
<213> ORGANISM: Oryctolagus cuniculus

<400> SEQUENCE: 11

Gln Glu Gln Leu Glu Glu Ser Gly Gly Arg Leu Val Thr Pro Gly Thr
1               5                   10                  15

Pro Leu Thr Leu Thr Cys Thr Ala Ser Gly Phe Ser Leu Ser Asn Tyr
                20                  25                  30

Tyr Met Ser Trp Val Arg Gln Ala Pro Gly Lys Gly Leu Glu Tyr Ile
            35                  40                  45

Gly Ile Ile Ser Ser Ser Gly Ser Thr Tyr Tyr Ala Ser Trp Ala Lys
    50                  55                  60

Gly Arg Phe Thr Ile Ser Lys Thr Ser Ser Thr Val Asp Leu Lys Leu
65                  70                  75                  80

Ile Thr Ser Pro Thr Thr Glu Asp Thr Ala Thr Tyr Phe Cys Ala Arg
                85                  90                  95

Leu Tyr Val Ser Asp Ser Thr Ala Asn Leu Trp Gly Pro Gly Thr Leu
            100                 105                 110

Val Thr Val Ser Ser
            115

<210> SEQ ID NO 12
<211> LENGTH: 114
<212> TYPE: PRT
<213> ORGANISM: Oryctolagus cuniculus

<400> SEQUENCE: 12

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Trp
                20                  25                  30

Met Ser Trp Val Arg Gln Ala Pro Gly Lys Gly Leu Glu Trp Ile Gly
            35                  40                  45

Ala Ile Tyr Gly Ser Gly Asn Thr Tyr Tyr Ala Ser Trp Ala Lys Gly
    50                  55                  60

Arg Phe Thr Ile Ser Lys Thr Ser Thr Thr Val Asp Leu Lys Ile Thr
65                  70                  75                  80

Ser Pro Thr Thr Glu Asp Thr Ala Thr Tyr Phe Cys Ala Arg Asp Val
                85                  90                  95

His Ser Thr Ala Thr Asp Leu Trp Gly Pro Gly Thr Leu Val Thr Ile
            100                 105                 110
```

Ser Ser

<210> SEQ ID NO 13
<211> LENGTH: 115
<212> TYPE: PRT
<213> ORGANISM: Oryctolagus cuniculus

<400> SEQUENCE: 13

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Asp Tyr Tyr
            20                  25                  30

Met Ser Trp Val Arg Gln Ala Pro Gly Glu Gly Leu Glu Trp Ile Gly
        35                  40                  45

Thr Ile Tyr Gly Gly Ser Gly Asn Thr Trp Tyr Ala Thr Trp Ala Lys
    50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Asp
                85                  90                  95

Phe Gly Leu Ser Thr Gly Gly Leu Trp Gly Pro Gly Thr Leu Val Thr
            100                 105                 110

Ile Ser Ser
        115

<210> SEQ ID NO 14
<211> LENGTH: 107
<212> TYPE: PRT
<213> ORGANISM: Oryctolagus cuniculus

<400> SEQUENCE: 14

Ser Tyr Glu Leu Thr Gln Leu Pro Ser Val Ser Val Ser Leu Gly Gln
1               5                   10                  15

Thr Ala Arg Ile Thr Cys Glu Gly Asn Asn Ile Gly Ser Lys Ala Val
            20                  25                  30

His Trp Tyr Gln Gln Lys Pro Gly Leu Ala Pro Gly Leu Leu Ile Tyr
        35                  40                  45

Asp Asp Asp Glu Arg Pro Ser Gly Val Pro Asp Arg Phe Ser Gly Ser
    50                  55                  60

Asn Ser Gly Asp Thr Ala Thr Leu Thr Ile Ser Gly Ala Gln Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Gln Leu Thr Val Thr Gly
            100                 105

<210> SEQ ID NO 15
<211> LENGTH: 109
<212> TYPE: PRT
<213> ORGANISM: Oryctolagus cuniculus

<400> SEQUENCE: 15

Ser Tyr Glu Leu Thr Gln Leu Pro Ser Val Ser Val Ser Leu Gly Gln
1               5                   10                  15

Thr Ala Arg Ile Thr Cys Gly Gly Asn Ser Ile Gly Ser Lys Ala Val
            20                  25                  30

Asn Trp Tyr Gln Gln Lys Pro Gly Leu Ala Pro Gly Leu Leu Ile Tyr

```
            35                  40                  45
Asp Asp Asp Glu Arg Pro Ser Gly Val Pro Asp Arg Phe Ser Ala Ser
         50                  55                  60

Asn Ser Gly Asp Thr Ala Thr Leu Thr Ile Ser Gly Ala Gln Ala Glu
 65                  70                  75                  80

Asp Glu Ala Asp Tyr Tyr Cys Gln Leu Trp Asp Ser Ser Ala Val Ala
                 85                  90                  95

Tyr Val Phe Gly Gly Gly Thr Gln Leu Thr Val Thr Gly
                100                 105

<210> SEQ ID NO 16
<211> LENGTH: 112
<212> TYPE: PRT
<213> ORGANISM: Oryctolagus cuniculus

<400> SEQUENCE: 16

Gln Phe Val Leu Thr Gln Ser Pro Ser Val Ser Ala Ala Leu Gly Ala
 1               5                  10                  15

Ser Ala Lys Leu Thr Cys Thr Leu Ser Ser Ala His Lys Thr Tyr Thr
                20                  25                  30

Ile Asp Trp Tyr Gln Gln Gln Gly Glu Ala Pro Arg Tyr Leu Met
             35                  40                  45

Glu Leu Lys Ser Asp Gly Ser Tyr Thr Lys Gly Thr Gly Val Pro Asp
         50                  55                  60

Arg Phe Ser Gly Ser Ser Ser Gly Ala Asp Arg Tyr Leu Ile Ile Pro
 65                  70                  75                  80

Ser Val Gln Ala Asp Asp Glu Ala Asp Tyr Tyr Cys Gly Thr Asp Tyr
                 85                  90                  95

Ser Gly Gly Tyr Val Phe Gly Gly Gly Thr Gln Leu Thr Val Thr Gly
                100                 105                 110

<210> SEQ ID NO 17
<211> LENGTH: 109
<212> TYPE: PRT
<213> ORGANISM: Oryctolagus cuniculus

<400> SEQUENCE: 17

Ser Tyr Glu Leu Thr Gln Leu Pro Ser Val Ser Val Ser Leu Gly Gln
 1               5                  10                  15

Thr Ala Arg Ile Thr Cys Gly Gly Asn Ser Ile Gly Ser Lys Ala Val
                20                  25                  30

Asn Trp Tyr Gln Gln Lys Pro Gly Leu Ala Pro Gly Leu Leu Ile Tyr
             35                  40                  45

Asp Asp Asp Glu Arg Pro Ser Gly Val Pro Asp Arg Phe Ser Gly Ser
         50                  55                  60

Asn Ser Gly Asp Thr Ala Thr Leu Thr Ile Ser Gly Ala Gln Ala Gly
 65                  70                  75                  80

Asp Glu Ala Asp Tyr Tyr Cys Gln Leu Trp Asp Ser Ser Thr Gly Ala
                 85                  90                  95

Tyr Ala Phe Gly Gly Gly Thr Gln Leu Thr Val Thr Gly
                100                 105

<210> SEQ ID NO 18
<211> LENGTH: 112
<212> TYPE: PRT
<213> ORGANISM: Oryctolagus cuniculus

<400> SEQUENCE: 18
```

```
Glu Leu Val Leu Thr Gln Thr Pro Ser Pro Val Ser Ala Ala Val Gly
1               5                   10                  15

Gly Thr Val Thr Ile Asn Cys Gln Ala Ser Gln Ser Val Tyr Gly Asn
            20                  25                  30

Asn Glu Leu Ala Trp Tyr Gln Gln Lys Pro Gly Gln Pro Pro Lys Leu
        35                  40                  45

Leu Ile Tyr Arg Ala Ser Ile Leu Thr Ser Gly Val Pro Ser Arg Phe
    50                  55                  60

Lys Gly Ser Gly Ser Gly Thr Gln Phe Thr Leu Thr Ile Ser Asn Val
65                  70                  75                  80

Gln Arg Glu Asp Ala Ala Thr Tyr Tyr Cys Leu Gly Gly Tyr Val Ser
                85                  90                  95

Gln Ser Tyr Arg Ala Ala Phe Gly Gly Gly Thr Glu Leu Glu Ile Leu
                100                 105                 110

<210> SEQ ID NO 19
<211> LENGTH: 109
<212> TYPE: PRT
<213> ORGANISM: Oryctolagus cuniculus

<400> SEQUENCE: 19

Ser Tyr Glu Leu Thr Gln Leu Pro Ser Val Ser Val Ser Leu Gly Gln
1               5                   10                  15

Thr Ala Arg Ile Thr Cys Gly Gly Asn Ser Ile Gly Ser Lys Ala Val
            20                  25                  30

Asn Trp Tyr Gln Gln Lys Pro Gly Leu Ala Pro Gly Leu Leu Ile Tyr
        35                  40                  45

Asp Asp Asp Glu Arg Pro Ser Gly Val Pro Ala Arg Phe Ser Gly Ser
    50                  55                  60

Asn Ser Gly Asp Thr Ala Thr Leu Thr Ile Ser Gly Ala Gln Ala Gly
65                  70                  75                  80

Asp Glu Ala Asp Tyr Tyr Cys Gln Leu Trp Asp Ser Ser Ala Gly Ala
                85                  90                  95

Tyr Val Phe Gly Gly Gly Thr Gln Leu Thr Val Thr Gly
                100                 105

<210> SEQ ID NO 20
<211> LENGTH: 111
<212> TYPE: PRT
<213> ORGANISM: Oryctolagus cuniculus

<400> SEQUENCE: 20

Gln Phe Val Leu Thr Gln Pro Gln Ser Val Ser Gly Ser Leu Gly Gln
1               5                   10                  15

Thr Val Ser Ile Ser Cys Asn Arg Asp Ser Gly Asn Ile Glu Asp Tyr
            20                  25                  30

Tyr Val His Trp Tyr Gln Gln His Pro Gly Lys Ala Pro Thr Thr Val
        35                  40                  45

Ile Tyr Asn Asp Asp Gln Arg Pro Ser Gly Val Pro Asp Arg Phe Ser
    50                  55                  60

Gly Ser Ile Asp Ser Thr Ser Asn Ser Ala Ser Leu Thr Ile Thr Gly
65                  70                  75                  80

Leu Leu Ala Glu Asp Glu Ala Asp Tyr Tyr Cys Leu Ser Ser Asp Ser
                85                  90                  95

Ser Ala Tyr Val Phe Gly Gly Gly Thr Gln Leu Thr Val Thr Gly
                100                 105                 110
```

<210> SEQ ID NO 21
<211> LENGTH: 107
<212> TYPE: PRT
<213> ORGANISM: Oryctolagus cuniculus

<400> SEQUENCE: 21

Ser Tyr Glu Leu Thr Gln Leu Pro Ser Val Ser Val Ser Leu Gly Gln
1               5                   10                  15

Thr Ala Arg Ile Thr Cys Gly Gly Asp Ser Ile Glu Ser Lys Ala Val
            20                  25                  30

His Trp Tyr Gln Gln Lys Pro Gly Leu Ala Pro Gly Leu Leu Val Tyr
        35                  40                  45

Asn Asp Asp Glu Arg Pro Ser Gly Val Pro Asp Arg Phe Ser Gly Ser
    50                  55                  60

Asn Ser Gly Asp Thr Ala Thr Leu Thr Ile Ser Gly Ala Gln Ala Gly
65                  70                  75                  80

Asp Glu Ala Asp Tyr Tyr Cys Gln Leu Trp Asp Gly Ser Ala Tyr Val
                85                  90                  95

Phe Gly Gly Gly Thr Gln Leu Thr Val Thr Gly
            100                 105

<210> SEQ ID NO 22
<211> LENGTH: 109
<212> TYPE: PRT
<213> ORGANISM: Oryctolagus cuniculus

<400> SEQUENCE: 22

Ser Tyr Glu Leu Thr Gln Leu Pro Ser Val Ser Val Ser Leu Gly Gln
1               5                   10                  15

Thr Ala Arg Ile Thr Cys Gly Gly Asn Ser Ile Gly Ser Lys Ala Val
            20                  25                  30

His Trp Tyr Gln Gln Lys Pro Gly Leu Ala Pro Gly Leu Leu Ile Tyr
        35                  40                  45

Asp Asp Asp Glu Arg Pro Ser Gly Val Pro Asp Arg Phe Ser Gly Ser
    50                  55                  60

Asn Ser Gly Asp Thr Ala Thr Leu Thr Ile Ser Gly Ala Gln Ala Gly
65                  70                  75                  80

Asp Glu Ala Asp Tyr Tyr Cys Gln Leu Trp Asp Ser Ser Ala Gly Ala
                85                  90                  95

Tyr Val Phe Gly Gly Gly Thr Gln Leu Thr Val Thr Gly
            100                 105

<210> SEQ ID NO 23
<211> LENGTH: 107
<212> TYPE: PRT
<213> ORGANISM: Oryctolagus cuniculus

<400> SEQUENCE: 23

Ser Tyr Glu Leu Thr Gln Leu Pro Ser Val Ser Val Ser Leu Gly Gln
1               5                   10                  15

Thr Ala Arg Ile Thr Cys Gly Gly Asn Ser Ile Gly Ser Lys Ala Val
            20                  25                  30

His Trp Tyr Gln Gln Lys Pro Gly Leu Ala Pro Gly Leu Leu Ile Tyr
        35                  40                  45

Asn Asp Asp Glu Arg Pro Ser Gly Val Pro Asp Arg Phe Ser Gly Ser
    50                  55                  60

```
Asn Ser Gly Asp Thr Ala Thr Leu Thr Ile Ser Gly Ala Gln Ala Gly
 65                  70                  75                  80

Asp Glu Ala Asp Tyr Tyr Cys Gln Leu Trp Asp Asn Asn Ala Ala Val
                 85                  90                  95

Phe Gly Gly Gly Thr Gln Leu Thr Val Thr Gly
            100                 105

<210> SEQ ID NO 24
<211> LENGTH: 110
<212> TYPE: PRT
<213> ORGANISM: Oryctolagus cuniculus

<400> SEQUENCE: 24

Asp Ile Val Leu Thr Gln Thr Pro Ser Ser Thr Ser Ala Ala Val Gly
  1               5                  10                  15

Gly Thr Val Thr Ile Lys Cys Gln Ala Ser Gln Ser Ile Asp Ser Tyr
                 20                  25                  30

Leu Ala Trp Tyr Gln Gln Lys Pro Gly Gln Pro Pro Lys Leu Leu Ile
             35                  40                  45

Tyr Gly Ala Ser Asn Leu Ala Ser Gly Val Pro Ser Arg Phe Ser Gly
 50                  55                  60

Ser Arg Ser Gly Thr Glu Tyr Ile Leu Thr Ile Ser Gly Val Gln Arg
 65                  70                  75                  80

Glu Asp Ala Ala Thr Tyr Tyr Cys Leu Gly Gly Tyr Pro Asn Tyr Phe
                 85                  90                  95

His Arg Thr Ala Phe Gly Gly Gly Thr Lys Leu Glu Ile Lys
            100                 105                 110

<210> SEQ ID NO 25
<211> LENGTH: 109
<212> TYPE: PRT
<213> ORGANISM: Oryctolagus cuniculus

<400> SEQUENCE: 25

Ser Tyr Glu Leu Thr Gln Leu Pro Ser Val Ser Val Ser Leu Gly Gln
  1               5                  10                  15

Thr Ala Arg Ile Thr Cys Gly Gly Asn Ile Gly Ser Lys Ala Val
                 20                  25                  30

Asn Trp Tyr Gln Gln Lys Pro Gly Leu Ala Pro Gly Leu Leu Ile Tyr
             35                  40                  45

Asn Asp Asp Glu Arg Pro Ser Gly Val Pro Asp Arg Phe Ser Gly Ser
 50                  55                  60

Asn Ser Gly Asp Thr Ala Thr Leu Thr Ile Ser Gly Ala Gln Ala Gly
 65                  70                  75                  80

Asp Glu Ala Asp Tyr Tyr Cys Gln Leu Trp Asp Ser Ser Ala Gly Ala
                 85                  90                  95

Tyr Val Phe Gly Gly Gly Thr Gln Leu Thr Val Thr Gly
            100                 105

<210> SEQ ID NO 26
<211> LENGTH: 109
<212> TYPE: PRT
<213> ORGANISM: Oryctolagus cuniculus

<400> SEQUENCE: 26

Ser Tyr Glu Leu Thr Gln Leu Pro Ser Val Ser Val Ser Leu Gly Gln
  1               5                  10                  15

Thr Ala Arg Ile Thr Cys Gly Gly Asn Ser Ile Gly Ser Lys Ala Val
```

```
            20                  25                  30
Asn Trp Tyr Gln Gln Lys Pro Gly Leu Ala Pro Gly Leu Leu Ile Tyr
            35                  40                  45

Asp Asp Asp Glu Arg Pro Ser Gly Val Pro Asp Arg Phe Ser Gly Ser
    50                  55                  60

Asn Ser Gly Asp Thr Ala Thr Leu Thr Ile Ser Gly Ala Gln Ala Gly
65                  70                  75                  80

Asp Glu Ala Asp Tyr Tyr Cys Gln Leu Trp Asp Ser Ser Ala Arg Ala
                85                  90                  95

Phe Val Phe Gly Gly Gly Thr Gln Leu Thr Val Thr Gly
                100                 105

<210> SEQ ID NO 27
<211> LENGTH: 5
<212> TYPE: PRT
<213> ORGANISM: Oryctolagus cuniculus

<400> SEQUENCE: 27

Ser Tyr Tyr Met Ser
1               5

<210> SEQ ID NO 28
<211> LENGTH: 16
<212> TYPE: PRT
<213> ORGANISM: Oryctolagus cuniculus

<400> SEQUENCE: 28

Ala Ile Gly Ile Ser Gly Asn Ala Tyr Tyr Ala Ser Trp Ala Lys Ser
1               5                   10                  15

<210> SEQ ID NO 29
<211> LENGTH: 9
<212> TYPE: PRT
<213> ORGANISM: Oryctolagus cuniculus

<400> SEQUENCE: 29

Asp His Pro Thr Tyr Gly Met Asp Leu
1               5

<210> SEQ ID NO 30
<211> LENGTH: 5
<212> TYPE: PRT
<213> ORGANISM: Oryctolagus cuniculus

<400> SEQUENCE: 30

Thr Tyr His Met Ser
1               5

<210> SEQ ID NO 31
<211> LENGTH: 17
<212> TYPE: PRT
<213> ORGANISM: Oryctolagus cuniculus

<400> SEQUENCE: 31

Ser Ile Tyr Ala Gly Ser Gly Ser Thr Tyr Tyr Ala Ser Trp Val Asn
1               5                   10                  15

Gly

<210> SEQ ID NO 32
<211> LENGTH: 9
<212> TYPE: PRT
<213> ORGANISM: Oryctolagus cuniculus
```

```
<400> SEQUENCE: 32

Asp His Pro Ser Tyr Gly Met Asp Leu
1               5

<210> SEQ ID NO 33
<211> LENGTH: 5
<212> TYPE: PRT
<213> ORGANISM: Oryctolagus cuniculus

<400> SEQUENCE: 33

Asn Tyr Gly Val Ser
1               5

<210> SEQ ID NO 34
<211> LENGTH: 17
<212> TYPE: PRT
<213> ORGANISM: Oryctolagus cuniculus

<400> SEQUENCE: 34

Tyr Ile Asp Pro Thr Phe Asp Tyr Thr Tyr Tyr Ala Ser Trp Val Asn
1               5                   10                  15

Gly

<210> SEQ ID NO 35
<211> LENGTH: 16
<212> TYPE: PRT
<213> ORGANISM: Oryctolagus cuniculus

<400> SEQUENCE: 35

Trp Val Tyr Gly Val Asp Asp Tyr Gly Asp Gly Asn Trp Leu Asp Leu
1               5                   10                  15

<210> SEQ ID NO 36
<211> LENGTH: 5
<212> TYPE: PRT
<213> ORGANISM: Oryctolagus cuniculus

<400> SEQUENCE: 36

Ser Tyr Tyr Val Ser
1               5

<210> SEQ ID NO 37
<211> LENGTH: 16
<212> TYPE: PRT
<213> ORGANISM: Oryctolagus cuniculus

<400> SEQUENCE: 37

Ala Ile Gly Thr Gly Gly Ser Ala Tyr Tyr Ala Ser Trp Ala Lys Ser
1               5                   10                  15

<210> SEQ ID NO 38
<211> LENGTH: 9
<212> TYPE: PRT
<213> ORGANISM: Oryctolagus cuniculus

<400> SEQUENCE: 38

Asp His Pro Asn Tyr Gly Met Asp Leu
1               5

<210> SEQ ID NO 39
<211> LENGTH: 5
<212> TYPE: PRT
<213> ORGANISM: Oryctolagus cuniculus
```

<400> SEQUENCE: 39

Arg Asn Gly Met Thr
1               5

<210> SEQ ID NO 40
<211> LENGTH: 16
<212> TYPE: PRT
<213> ORGANISM: Oryctolagus cuniculus

<400> SEQUENCE: 40

Ile Ile Thr Ser Ser Gly Asp Lys Tyr Tyr Ala Thr Trp Ala Lys Gly
1               5                   10                  15

<210> SEQ ID NO 41
<211> LENGTH: 7
<212> TYPE: PRT
<213> ORGANISM: Oryctolagus cuniculus

<400> SEQUENCE: 41

Gly Thr Val Ser Ser Asp Ile
1               5

<210> SEQ ID NO 42
<211> LENGTH: 5
<212> TYPE: PRT
<213> ORGANISM: Oryctolagus cuniculus

<400> SEQUENCE: 42

Gly Trp Tyr Met Thr
1               5

<210> SEQ ID NO 43
<211> LENGTH: 17
<212> TYPE: PRT
<213> ORGANISM: Oryctolagus cuniculus

<400> SEQUENCE: 43

Thr Ile Gly Thr Thr Lys Gly Arg Thr Tyr Tyr Ala Ser Trp Val Asn
1               5                   10                  15

Gly

<210> SEQ ID NO 44
<211> LENGTH: 7
<212> TYPE: PRT
<213> ORGANISM: Oryctolagus cuniculus

<400> SEQUENCE: 44

Gly Ser Asp Tyr Phe Asp Leu
1               5

<210> SEQ ID NO 45
<211> LENGTH: 5
<212> TYPE: PRT
<213> ORGANISM: Oryctolagus cuniculus

<400> SEQUENCE: 45

Ser Tyr Tyr Met Gly
1               5

<210> SEQ ID NO 46
<211> LENGTH: 17
<212> TYPE: PRT
<213> ORGANISM: Oryctolagus cuniculus

<400> SEQUENCE: 46

Thr Ile Tyr Gly Gly Ser Gly Ser Thr Trp Tyr Ala Ser Trp Val Lys
1               5                   10                  15
Gly

<210> SEQ ID NO 47
<211> LENGTH: 13
<212> TYPE: PRT
<213> ORGANISM: Oryctolagus cuniculus

<400> SEQUENCE: 47

Ser Tyr Pro Gly Trp Thr Thr Glu Pro Tyr Phe Asp Ile
1               5                   10

<210> SEQ ID NO 48
<211> LENGTH: 5
<212> TYPE: PRT
<213> ORGANISM: Oryctolagus cuniculus

<400> SEQUENCE: 48

Arg Tyr Ala Val Asn
1               5

<210> SEQ ID NO 49
<211> LENGTH: 16
<212> TYPE: PRT
<213> ORGANISM: Oryctolagus cuniculus

<400> SEQUENCE: 49

Val Ile Ser Gly Ser Gly Thr Thr Tyr Tyr Ala Ser Trp Ala Lys Gly
1               5                   10                  15

<210> SEQ ID NO 50
<211> LENGTH: 16
<212> TYPE: PRT
<213> ORGANISM: Oryctolagus cuniculus

<400> SEQUENCE: 50

Gly Trp Ala Thr Asp Gly Ile Phe Asp Tyr Asp Asp Thr Phe Asn Leu
1               5                   10                  15

<210> SEQ ID NO 51
<211> LENGTH: 5
<212> TYPE: PRT
<213> ORGANISM: Oryctolagus cuniculus

<400> SEQUENCE: 51

Ser Tyr Trp Met Ser
1               5

<210> SEQ ID NO 52
<211> LENGTH: 17
<212> TYPE: PRT
<213> ORGANISM: Oryctolagus cuniculus

<400> SEQUENCE: 52

Ala Ile Tyr Val Asp Ser Gly Ser Ala Tyr Tyr Ala Ser Trp Ala Lys
1               5                   10                  15
Ser

<210> SEQ ID NO 53
<211> LENGTH: 7

<212> TYPE: PRT
<213> ORGANISM: Oryctolagus cuniculus

<400> SEQUENCE: 53

Asp Gly Trp Gly Ser Asp Val
1               5

<210> SEQ ID NO 54
<211> LENGTH: 5
<212> TYPE: PRT
<213> ORGANISM: Oryctolagus cuniculus

<400> SEQUENCE: 54

Ser Tyr Tyr Met Ser
1               5

<210> SEQ ID NO 55
<211> LENGTH: 16
<212> TYPE: PRT
<213> ORGANISM: Oryctolagus cuniculus

<400> SEQUENCE: 55

Thr Ile Ser Ser Ser Gly Ser Thr Tyr Tyr Ala Ser Trp Val Lys Gly
1               5                   10                  15

<210> SEQ ID NO 56
<211> LENGTH: 10
<212> TYPE: PRT
<213> ORGANISM: Oryctolagus cuniculus

<400> SEQUENCE: 56

Leu Tyr Val Ser Asp Ser Thr Ala Asn Leu
1               5                   10

<210> SEQ ID NO 57
<211> LENGTH: 5
<212> TYPE: PRT
<213> ORGANISM: Oryctolagus cuniculus

<400> SEQUENCE: 57

Asn Tyr Tyr Met Ser
1               5

<210> SEQ ID NO 58
<211> LENGTH: 16
<212> TYPE: PRT
<213> ORGANISM: Oryctolagus cuniculus

<400> SEQUENCE: 58

Ile Ile Ser Ser Ser Gly Ser Thr Tyr Tyr Ala Ser Trp Ala Lys Gly
1               5                   10                  15

<210> SEQ ID NO 59
<211> LENGTH: 10
<212> TYPE: PRT
<213> ORGANISM: Oryctolagus cuniculus

<400> SEQUENCE: 59

Leu Tyr Val Ser Asp Ser Thr Ala Asn Leu
1               5                   10

<210> SEQ ID NO 60
<211> LENGTH: 5
<212> TYPE: PRT
<213> ORGANISM: Oryctolagus cuniculus

<400> SEQUENCE: 60

Ser Tyr Trp Met Ser
1               5

<210> SEQ ID NO 61
<211> LENGTH: 16
<212> TYPE: PRT
<213> ORGANISM: Oryctolagus cuniculus

<400> SEQUENCE: 61

Ala Ile Tyr Gly Ser Gly Asn Thr Tyr Tyr Ala Ser Trp Ala Lys Gly
1               5                   10                  15

<210> SEQ ID NO 62
<211> LENGTH: 9
<212> TYPE: PRT
<213> ORGANISM: Oryctolagus cuniculus

<400> SEQUENCE: 62

Asp Val His Ser Thr Ala Thr Asp Leu
1               5

<210> SEQ ID NO 63
<211> LENGTH: 5
<212> TYPE: PRT
<213> ORGANISM: Oryctolagus cuniculus

<400> SEQUENCE: 63

Asp Tyr Tyr Met Ser
1               5

<210> SEQ ID NO 64
<211> LENGTH: 17
<212> TYPE: PRT
<213> ORGANISM: Oryctolagus cuniculus

<400> SEQUENCE: 64

Thr Ile Tyr Gly Gly Ser Gly Asn Thr Trp Tyr Ala Thr Trp Ala Lys
1               5                   10                  15

Gly

<210> SEQ ID NO 65
<211> LENGTH: 9
<212> TYPE: PRT
<213> ORGANISM: Oryctolagus cuniculus

<400> SEQUENCE: 65

Asp Phe Gly Leu Ser Thr Gly Gly Leu
1               5

<210> SEQ ID NO 66
<211> LENGTH: 11
<212> TYPE: PRT
<213> ORGANISM: Oryctolagus cuniculus

<400> SEQUENCE: 66

Glu Gly Asn Asn Ile Gly Ser Lys Ala Val His
1               5                   10

<210> SEQ ID NO 67
<211> LENGTH: 7
<212> TYPE: PRT
<213> ORGANISM: Oryctolagus cuniculus

```
<400> SEQUENCE: 67

Asp Asp Asp Glu Arg Pro Ser
1               5

<210> SEQ ID NO 68
<211> LENGTH: 9
<212> TYPE: PRT
<213> ORGANISM: Oryctolagus cuniculus

<400> SEQUENCE: 68

Gln Val Trp Asp Ser Ser Ala Tyr Val
1               5

<210> SEQ ID NO 69
<211> LENGTH: 11
<212> TYPE: PRT
<213> ORGANISM: Oryctolagus cuniculus

<400> SEQUENCE: 69

Gly Gly Asn Ser Ile Gly Ser Lys Ala Val Asn
1               5                   10

<210> SEQ ID NO 70
<211> LENGTH: 7
<212> TYPE: PRT
<213> ORGANISM: Oryctolagus cuniculus

<400> SEQUENCE: 70

Asp Asp Asp Glu Arg Pro Ser
1               5

<210> SEQ ID NO 71
<211> LENGTH: 11
<212> TYPE: PRT
<213> ORGANISM: Oryctolagus cuniculus

<400> SEQUENCE: 71

Gln Leu Trp Asp Ser Ser Ala Val Ala Tyr Val
1               5                   10

<210> SEQ ID NO 72
<211> LENGTH: 12
<212> TYPE: PRT
<213> ORGANISM: Oryctolagus cuniculus

<400> SEQUENCE: 72

Thr Leu Ser Ser Ala His Lys Thr Tyr Thr Ile Asp
1               5                   10

<210> SEQ ID NO 73
<211> LENGTH: 11
<212> TYPE: PRT
<213> ORGANISM: Oryctolagus cuniculus

<400> SEQUENCE: 73

Leu Lys Ser Asp Gly Ser Tyr Thr Lys Gly Thr
1               5                   10

<210> SEQ ID NO 74
<211> LENGTH: 9
<212> TYPE: PRT
<213> ORGANISM: Oryctolagus cuniculus

<400> SEQUENCE: 74
```

```
Gly Thr Asp Tyr Ser Gly Gly Tyr Val
1               5
```

```
<210> SEQ ID NO 75
<211> LENGTH: 11
<212> TYPE: PRT
<213> ORGANISM: Oryctolagus cuniculus

<400> SEQUENCE: 75

Gly Gly Asn Ser Ile Gly Ser Lys Ala Val Asn
1               5                   10
```

```
<210> SEQ ID NO 76
<211> LENGTH: 7
<212> TYPE: PRT
<213> ORGANISM: Oryctolagus cuniculus

<400> SEQUENCE: 76

Asp Asp Asp Glu Arg Pro Ser
1               5
```

```
<210> SEQ ID NO 77
<211> LENGTH: 11
<212> TYPE: PRT
<213> ORGANISM: Oryctolagus cuniculus

<400> SEQUENCE: 77

Gln Leu Trp Asp Ser Ser Thr Gly Ala Tyr Ala
1               5                   10
```

```
<210> SEQ ID NO 78
<211> LENGTH: 13
<212> TYPE: PRT
<213> ORGANISM: Oryctolagus cuniculus

<400> SEQUENCE: 78

Gln Ala Ser Gln Ser Val Tyr Gly Asn Asn Glu Leu Ala
1               5                   10
```

```
<210> SEQ ID NO 79
<211> LENGTH: 7
<212> TYPE: PRT
<213> ORGANISM: Oryctolagus cuniculus

<400> SEQUENCE: 79

Arg Ala Ser Ile Leu Thr Ser
1               5
```

```
<210> SEQ ID NO 80
<211> LENGTH: 12
<212> TYPE: PRT
<213> ORGANISM: Oryctolagus cuniculus

<400> SEQUENCE: 80

Leu Gly Gly Tyr Val Ser Gln Ser Tyr Arg Ala Ala
1               5                   10
```

```
<210> SEQ ID NO 81
<211> LENGTH: 11
<212> TYPE: PRT
<213> ORGANISM: Oryctolagus cuniculus

<400> SEQUENCE: 81

Gly Gly Asn Ser Ile Gly Ser Lys Ala Val Asn
```

```
1               5               10

<210> SEQ ID NO 82
<211> LENGTH: 7
<212> TYPE: PRT
<213> ORGANISM: Oryctolagus cuniculus

<400> SEQUENCE: 82

Asp Asp Asp Glu Arg Pro Ser
1               5

<210> SEQ ID NO 83
<211> LENGTH: 11
<212> TYPE: PRT
<213> ORGANISM: Oryctolagus cuniculus

<400> SEQUENCE: 83

Gln Leu Trp Asp Ser Ser Ala Gly Ala Tyr Val
1               5                   10

<210> SEQ ID NO 84
<211> LENGTH: 13
<212> TYPE: PRT
<213> ORGANISM: Oryctolagus cuniculus

<400> SEQUENCE: 84

Asn Arg Asp Ser Gly Asn Ile Glu Asp Tyr Tyr Val His
1               5                   10

<210> SEQ ID NO 85
<211> LENGTH: 7
<212> TYPE: PRT
<213> ORGANISM: Oryctolagus cuniculus

<400> SEQUENCE: 85

Asn Asp Asp Gln Arg Pro Ser
1               5

<210> SEQ ID NO 86
<211> LENGTH: 9
<212> TYPE: PRT
<213> ORGANISM: Oryctolagus cuniculus

<400> SEQUENCE: 86

Leu Ser Ser Asp Ser Ser Ala Tyr Val
1               5

<210> SEQ ID NO 87
<211> LENGTH: 11
<212> TYPE: PRT
<213> ORGANISM: Oryctolagus cuniculus

<400> SEQUENCE: 87

Gly Gly Asp Ser Ile Glu Ser Lys Ala Val His
1               5                   10

<210> SEQ ID NO 88
<211> LENGTH: 7
<212> TYPE: PRT
<213> ORGANISM: Oryctolagus cuniculus

<400> SEQUENCE: 88

Asn Asp Asp Glu Arg Pro Ser
1               5
```

```
<210> SEQ ID NO 89
<211> LENGTH: 9
<212> TYPE: PRT
<213> ORGANISM: Oryctolagus cuniculus

<400> SEQUENCE: 89

Gln Leu Trp Asp Gly Ser Ala Tyr Val
1               5

<210> SEQ ID NO 90
<211> LENGTH: 11
<212> TYPE: PRT
<213> ORGANISM: Oryctolagus cuniculus

<400> SEQUENCE: 90

Gly Gly Asn Ser Ile Gly Ser Lys Ala Val His
1               5                   10

<210> SEQ ID NO 91
<211> LENGTH: 7
<212> TYPE: PRT
<213> ORGANISM: Oryctolagus cuniculus

<400> SEQUENCE: 91

Asp Asp Asp Glu Arg Pro Ser
1               5

<210> SEQ ID NO 92
<211> LENGTH: 11
<212> TYPE: PRT
<213> ORGANISM: Oryctolagus cuniculus

<400> SEQUENCE: 92

Gln Leu Trp Asp Ser Ser Ala Gly Ala Tyr Val
1               5                   10

<210> SEQ ID NO 93
<211> LENGTH: 11
<212> TYPE: PRT
<213> ORGANISM: Oryctolagus cuniculus

<400> SEQUENCE: 93

Gly Gly Asn Ser Ile Gly Ser Lys Ala Val His
1               5                   10

<210> SEQ ID NO 94
<211> LENGTH: 7
<212> TYPE: PRT
<213> ORGANISM: Oryctolagus cuniculus

<400> SEQUENCE: 94

Asn Asp Asp Glu Arg Pro Ser
1               5

<210> SEQ ID NO 95
<211> LENGTH: 9
<212> TYPE: PRT
<213> ORGANISM: Oryctolagus cuniculus

<400> SEQUENCE: 95

Gln Leu Trp Asp Asn Asn Ala Ala Val
1               5

<210> SEQ ID NO 96
```

```
<211> LENGTH: 11
<212> TYPE: PRT
<213> ORGANISM: Oryctolagus cuniculus

<400> SEQUENCE: 96

Gln Ala Ser Gln Ser Ile Asp Ser Tyr Leu Ala
1               5                   10

<210> SEQ ID NO 97
<211> LENGTH: 7
<212> TYPE: PRT
<213> ORGANISM: Oryctolagus cuniculus

<400> SEQUENCE: 97

Gly Ala Ser Asn Leu Ala Ser
1               5

<210> SEQ ID NO 98
<211> LENGTH: 12
<212> TYPE: PRT
<213> ORGANISM: Oryctolagus cuniculus

<400> SEQUENCE: 98

Leu Gly Gly Tyr Pro Asn Tyr Phe His Arg Thr Ala
1               5                   10

<210> SEQ ID NO 99
<211> LENGTH: 11
<212> TYPE: PRT
<213> ORGANISM: Oryctolagus cuniculus

<400> SEQUENCE: 99

Gly Gly Asn Asn Ile Gly Ser Lys Ala Val Asn
1               5                   10

<210> SEQ ID NO 100
<211> LENGTH: 7
<212> TYPE: PRT
<213> ORGANISM: Oryctolagus cuniculus

<400> SEQUENCE: 100

Asn Asp Asp Glu Arg Pro Ser
1               5

<210> SEQ ID NO 101
<211> LENGTH: 11
<212> TYPE: PRT
<213> ORGANISM: Oryctolagus cuniculus

<400> SEQUENCE: 101

Gln Leu Trp Asp Ser Ser Ala Gly Ala Tyr Val
1               5                   10

<210> SEQ ID NO 102
<211> LENGTH: 11
<212> TYPE: PRT
<213> ORGANISM: Oryctolagus cuniculus

<400> SEQUENCE: 102

Gly Gly Asn Ser Ile Gly Ser Lys Ala Val Asn
1               5                   10

<210> SEQ ID NO 103
<211> LENGTH: 7
<212> TYPE: PRT
```

<213> ORGANISM: Oryctolagus cuniculus

<400> SEQUENCE: 103

Asp Asp Asp Glu Arg Pro Ser
1               5

<210> SEQ ID NO 104
<211> LENGTH: 11
<212> TYPE: PRT
<213> ORGANISM: Oryctolagus cuniculus

<400> SEQUENCE: 104

Gln Leu Trp Asp Ser Ser Ala Arg Ala Phe Val
1               5                   10

<210> SEQ ID NO 105
<211> LENGTH: 60
<212> TYPE: DNA
<213> ORGANISM: Artificial sequence
<220> FEATURE:
<223> OTHER INFORMATION: Synthetic sequence

<400> SEQUENCE: 105
atcctgtttc tcgtagctgc tgcaactgga gcacactccg cccggggcgc cgccgcccag      60

<210> SEQ ID NO 106
<211> LENGTH: 60
<212> TYPE: DNA
<213> ORGANISM: Artificial sequence
<220> FEATURE:
<223> OTHER INFORMATION: Synthetic sequence

<400> SEQUENCE: 106
ccactcgatc ttctgggcct cgaagatgtc gttcaggccc tccatcttgt tcttctcctt      60

<210> SEQ ID NO 107
<211> LENGTH: 60
<212> TYPE: DNA
<213> ORGANISM: Artificial sequence
<220> FEATURE:
<223> OTHER INFORMATION: Synthetic sequence

<400> SEQUENCE: 107
gctgggtacc ggcgcgccac catggactgg acttggagaa tcctgtttct cgtagctgct      60

<210> SEQ ID NO 108
<211> LENGTH: 60
<212> TYPE: DNA
<213> ORGANISM: Artificial sequence
<220> FEATURE:
<223> OTHER INFORMATION: Synthetic sequence

<400> SEQUENCE: 108
gccggcctcg agtcagtgat ggtgatggtg gtgctcgtgc cactcgatct tctgggcctc      60

<210> SEQ ID NO 109
<211> LENGTH: 99
<212> TYPE: DNA
<213> ORGANISM: Artificial sequence
<220> FEATURE:
<223> OTHER INFORMATION: Synthetic sequence

<400> SEQUENCE: 109
gctgggtacc ggcgcgccac catggactgg acttggagaa tcctgtttct cgtagctgct      60
gcaactggag cacactccgc ccggggcgcc gccgcccag                             99

<210> SEQ ID NO 110
<211> LENGTH: 52
<212> TYPE: DNA
<213> ORGANISM: Artificial sequence
<220> FEATURE:
<223> OTHER INFORMATION: Synthetic sequence

<400> SEQUENCE: 110
cggcctcgag tcagtgatgg tgatggtggt gctccatctt gttcttctcc tt        52

<210> SEQ ID NO 111
<211> LENGTH: 99
<212> TYPE: DNA
<213> ORGANISM: Artificial sequence
<220> FEATURE:
<223> OTHER INFORMATION: Synthetic sequence

<400> SEQUENCE: 111
gctgggtacc ggcgcgccac catggactgg acttggagaa tcctgtttct cgtagctgct        60
gcaactggag cacactccga agtggaggtt ctggatccg                              99

<210> SEQ ID NO 112
<211> LENGTH: 52
<212> TYPE: DNA
<213> ORGANISM: Artificial sequence
<220> FEATURE:
<223> OTHER INFORMATION: Synthetic sequence

<400> SEQUENCE: 112
cggcctcgag tcagtgatgg tgatggtggt gccccatctt gctgctgtct cg        52

<210> SEQ ID NO 113
<211> LENGTH: 41
<212> TYPE: DNA
<213> ORGANISM: Artificial sequence
<220> FEATURE:
<223> OTHER INFORMATION: Synthetic sequence

<400> SEQUENCE: 113
gaggaggagc tcactctcag gagcagcaga aggagtccgg g        41

<210> SEQ ID NO 114
<211> LENGTH: 60
<212> TYPE: DNA
<213> ORGANISM: Artificial sequence
<220> FEATURE:
<223> OTHER INFORMATION: Synthetic sequence

<400> SEQUENCE: 114
cgatgggccc ttggtggagg ctgaagagac ggtgacgagg gtccctggcc cccagaggtc        60

<210> SEQ ID NO 115
<211> LENGTH: 60
<212> TYPE: DNA
<213> ORGANISM: Artificial sequence
<220> FEATURE:
<223> OTHER INFORMATION: Synthetic sequence

<400> SEQUENCE: 115
gagaagcttg ttgctctgga tctctggtgc ctacgggtcc tatgagctga cacagctgcc        60

<210> SEQ ID NO 116
<211> LENGTH: 21
<212> TYPE: DNA

```
<213> ORGANISM: Artificial sequence
<220> FEATURE:
<223> OTHER INFORMATION: Synthetic sequence

<400> SEQUENCE: 116
ggccatggct ggttgggcag c                                        21

<210> SEQ ID NO 117
<211> LENGTH: 60
<212> TYPE: DNA
<213> ORGANISM: Artificial sequence
<220> FEATURE:
<223> OTHER INFORMATION: Synthetic sequence

<400> SEQUENCE: 117
ggtaccggcg cgccaccatg gactggactt ggagaatcct gtttctcgta gctgctgcaa    60

<210> SEQ ID NO 118
<211> LENGTH: 20
<212> TYPE: DNA
<213> ORGANISM: Artificial sequence
<220> FEATURE:
<223> OTHER INFORMATION: Synthetic sequence

<400> SEQUENCE: 118
gccgctggtc agggctcctg                                          20

<210> SEQ ID NO 119
<211> LENGTH: 20
<212> TYPE: DNA
<213> ORGANISM: Artificial sequence
<220> FEATURE:
<223> OTHER INFORMATION: Synthetic sequence

<400> SEQUENCE: 119
caggagccct gaccagcggc                                          20

<210> SEQ ID NO 120
<211> LENGTH: 30
<212> TYPE: DNA
<213> ORGANISM: Artificial sequence
<220> FEATURE:
<223> OTHER INFORMATION: Synthetic sequence

<400> SEQUENCE: 120
ggcctcgagt catttacccg gagacaggga                               30

<210> SEQ ID NO 121
<211> LENGTH: 54
<212> TYPE: DNA
<213> ORGANISM: Artificial sequence
<220> FEATURE:
<223> OTHER INFORMATION: Synthetic sequence

<400> SEQUENCE: 121
tttctcgtag ctgctgcaac tgagcacac tcccagtcgc tggaggagtc cggg      54

<210> SEQ ID NO 122
<211> LENGTH: 54
<212> TYPE: PRT
<213> ORGANISM: Artificial sequence
<220> FEATURE:
<223> OTHER INFORMATION: Synthetic sequence

<400> SEQUENCE: 122

Thr Thr Thr Cys Thr Cys Gly Thr Ala Gly Cys Thr Gly Cys Thr Gly
```

```
  1               5                  10                 15
Cys Ala Ala Cys Thr Gly Gly Ala Gly Cys Ala Cys Ala Cys Thr Cys
                 20                 25                 30
Cys Cys Ala Gly Thr Cys Gly Thr Thr Gly Gly Ala Gly Gly Ala Gly
        35                 40                 45
Thr Cys Cys Gly Gly Gly
        50
```

<210> SEQ ID NO 123
<211> LENGTH: 54
<212> TYPE: DNA
<213> ORGANISM: Artificial sequence
<220> FEATURE:
<223> OTHER INFORMATION: Synthetic sequence

<400> SEQUENCE: 123
tttctcgtag ctgctgcaac tggagcacac tcccagtcgt tggaggagtc cggg          54

<210> SEQ ID NO 124
<211> LENGTH: 36
<212> TYPE: PRT
<213> ORGANISM: Artificial sequence
<220> FEATURE:
<223> OTHER INFORMATION: Synthetic sequence

<400> SEQUENCE: 124

```
Gly Gly Ala Gly Gly Gly Cys Gly Cys Cys Ala Gly Gly Gly Gly
1               5                  10                 15
Ala Ala Gly Ala Cys Cys Gly Ala Thr Gly Gly Gly Cys Cys Cys Thr
                20                 25                 30
Thr Gly Gly Thr
        35
```

<210> SEQ ID NO 125
<211> LENGTH: 54
<212> TYPE: DNA
<213> ORGANISM: Artificial sequence
<220> FEATURE:
<223> OTHER INFORMATION: Synthetic sequence

<400> SEQUENCE: 125
tttctcgtag ctgctgcaac tggagcacac tcctcctatg agctgacaca gctg          54

<210> SEQ ID NO 126
<211> LENGTH: 54
<212> TYPE: DNA
<213> ORGANISM: Artificial sequencee
<220> FEATURE:
<223> OTHER INFORMATION: Synthetic sequence

<400> SEQUENCE: 126
tttctcgtag ctgctgcaac tggagcacac tcctcctatg agctgacaca gctg          54

<210> SEQ ID NO 127
<211> LENGTH: 54
<212> TYPE: DNA
<213> ORGANISM: Artificial sequence
<220> FEATURE:
<223> OTHER INFORMATION: Synthetic sequence

<400> SEQUENCE: 127
tttctcgtag ctgctgcaac tggagcacac tccgagctcg tgctgaccca gact          54

```
<210> SEQ ID NO 128
<211> LENGTH: 30
<212> TYPE: DNA
<213> ORGANISM: Artificial sequence
<220> FEATURE:
<223> OTHER INFORMATION: Synthetic sequence

<400> SEQUENCE: 128
ggcctcgagt tatgaacatt ctgtaggggc                                     30

<210> SEQ ID NO 129
<211> LENGTH: 30
<212> TYPE: DNA
<213> ORGANISM: Artificial sequence
<220> FEATURE:
<223> OTHER INFORMATION: Synthetic sequence

<400> SEQUENCE: 129
ggcctcgagt taacactctc ccctgttgaa                                     30

<210> SEQ ID NO 130
<211> LENGTH: 117
<212> TYPE: PRT
<213> ORGANISM: Artificial sequence
<220> FEATURE:
<223> OTHER INFORMATION: Synthetic sequence

<400> SEQUENCE: 130

Gln Val Gln Leu Arg Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
        35                  40                  45

Gly Ala Ile Gly Ile Ser Gly Asn Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 131
<211> LENGTH: 117
<212> TYPE: PRT
<213> ORGANISM: Artificial sequence
<220> FEATURE:
<223> OTHER INFORMATION: Synthetic sequence

<400> SEQUENCE: 131

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
        35                  40                  45

Gly Ala Ile Gly Ile Ser Gly Asn Ala Tyr Tyr Ala Ser Trp Ala Lys
    50                  55                  60
```

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 132
<211> LENGTH: 117
<212> TYPE: PRT
<213> ORGANISM: Artificial sequence
<220> FEATURE:
<223> OTHER INFORMATION: Synthetic sequence

<400> SEQUENCE: 132

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
            35                  40                  45

Gly Ala Ile Gly Ile Ser Gly Asn Ala Tyr Tyr Ala Ser Trp Ala Lys
        50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 133
<211> LENGTH: 117
<212> TYPE: PRT
<213> ORGANISM: Artificial sequence
<220> FEATURE:
<223> OTHER INFORMATION: Synthetic sequence

<400> SEQUENCE: 133

Gln Val Gln Leu Arg Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Lys Gly Leu Glu Trp Ile
            35                  40                  45

Gly Ala Ile Gly Ile Ser Gly Asn Ala Tyr Tyr Ala Ser Trp Ala Lys
        50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 134
<211> LENGTH: 117
<212> TYPE: PRT
<213> ORGANISM: Artificial sequence
<220> FEATURE:
<223> OTHER INFORMATION: Synthetic sequence

<400> SEQUENCE: 134

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Asn Gly Leu Glu Trp Ile
        35                  40                  45

Gly Ala Ile Gly Ile Ser Gly Asn Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 135
<211> LENGTH: 117
<212> TYPE: PRT
<213> ORGANISM: Artificial sequence
<220> FEATURE:
<223> OTHER INFORMATION: Synthetic sequence

<400> SEQUENCE: 135

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Asp Ile Ser Ser Tyr
            20                  25                  30

Tyr Met Ser Trp Val Arg Gln Pro Pro Gly Asn Gly Leu Glu Trp Ile
        35                  40                  45

Gly Ala Ile Gly Ile Ser Gly Asn Ala Tyr Tyr Ala Ser Trp Ala Lys
    50                  55                  60

Ser Arg Val Thr Ile Ser Arg Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp His Pro Thr Tyr Gly Met Asp Leu Trp Gly Pro Gly Thr Leu
            100                 105                 110

Val Thr Val Ser Ser
        115

<210> SEQ ID NO 136
<211> LENGTH: 107
<212> TYPE: PRT
<213> ORGANISM: Artificial sequence
<220> FEATURE:
<223> OTHER INFORMATION: Synthetic sequence

<400> SEQUENCE: 136

Ser Tyr Glu Leu Thr Gln Pro Leu Ser Val Ser Val Ala Leu Gly Gln
1               5                   10                  15

Thr Ala Arg Ile Thr Cys Glu Gly Asn Asn Ile Gly Ser Lys Ala Val
            20                  25                  30

His Trp Tyr Gln Gln Lys Pro Gly Gln Ala Pro Val Leu Val Ile Tyr
            35                  40                  45

Asp Asp Asp Glu Arg Pro Ser Gly Ile Pro Glu Arg Phe Ser Gly Ser
        50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Lys Leu Thr Val Leu Gly
            100                 105

<210> SEQ ID NO 137
<211> LENGTH: 107
<212> TYPE: PRT
<213> ORGANISM: Artificial sequence
<220> FEATURE:
<223> OTHER INFORMATION: Synthetic sequence

<400> SEQUENCE: 137

Ser Tyr Glu Leu Thr Gln Pro Pro Ser Val Ser Val Ser Pro Gly Gln
1               5                   10                  15

Thr Ala Ile Ile Thr Cys Glu Gly Asn Asn Ile Gly Ser Lys Ala Val
            20                  25                  30

His Trp Tyr Gln Gln Lys Pro Gly Leu Ser Pro Val Leu Val Ile Tyr
            35                  40                  45

Asp Asp Asp Glu Arg Pro Ser Gly Ile Pro Glu Arg Phe Ser Gly Ser
        50                  55                  60

Asn Ser Gly Asn Thr Ala Thr Leu Thr Val Ser Gly Thr Gln Asp Met
65                  70                  75                  80

Asp Glu Ala Asp Tyr Tyr Cys Gln Val Trp Asp Ser Ser Ala Tyr Val
                85                  90                  95

Phe Gly Gly Gly Thr Lys Leu Thr Val Leu Gly
            100                 105

<210> SEQ ID NO 138
<211> LENGTH: 107
<212> TYPE: PRT
<213> ORGANISM: Artificial sequence
<220> FEATURE:
<223> OTHER INFORMATION: Synthetic sequence

<400> SEQUENCE: 138

Ser Tyr Glu Leu Thr Gln Pro Pro Ser Val Ser Val Ala Pro Gly Lys
1               5                   10                  15

Thr Ala Arg Ile Thr Cys Glu Gly Asn Asn Ile Gly Ser Lys Ala Val
            20                  25                  30

His Trp Tyr Gln Gln Lys Pro Gly Gln Ala Pro Val Leu Val Ile Tyr
            35                  40                  45

Asp Asp Asp Glu Arg Pro Ser Gly Ile Pro Glu Arg Phe Ser Gly Ser
        50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ala Tyr Val
                85                  90                  95

```
Phe Gly Gly Gly Thr Lys Leu Thr Val Leu Gly
            100                 105
```

<210> SEQ ID NO 139
<211> LENGTH: 107
<212> TYPE: PRT
<213> ORGANISM: Artificial sequence
<220> FEATURE:
<223> OTHER INFORMATION: Synthetic sequence

<400> SEQUENCE: 139

```
Ser Tyr Glu Leu Thr Gln Pro Pro Ser Val Ser Val Ala Pro Gly Lys
1               5                   10                  15

Thr Ala Arg Ile Thr Cys Glu Gly Asn Asn Ile Gly Ser Lys Ala Val
            20                  25                  30

His Trp Tyr Gln Gln Lys Pro Gly Gln Ala Pro Val Leu Val Ile Tyr
        35                  40                  45

Asp Asp Asp Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Lys Leu Thr Val Leu Gly
            100                 105
```

<210> SEQ ID NO 140
<211> LENGTH: 107
<212> TYPE: PRT
<213> ORGANISM: Artificial sequence
<220> FEATURE:
<223> OTHER INFORMATION: Synthetic sequence

<400> SEQUENCE: 140

```
Ser Tyr Glu Leu Thr Gln Pro Pro Ser Val Ser Val Ala Pro Gly Lys
1               5                   10                  15

Thr Ala Arg Ile Thr Cys Glu Gly Asn Asn Ile Gly Ser Lys Ala Val
            20                  25                  30

His Trp Tyr Gln Gln Lys Pro Gly Gln Ala Pro Val Leu Val Ile Tyr
        35                  40                  45

Asp Asp Asp Glu Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Lys Leu Thr Val Leu Gly
            100                 105
```

<210> SEQ ID NO 141
<211> LENGTH: 107
<212> TYPE: PRT
<213> ORGANISM: Artificial sequence
<220> FEATURE:
<223> OTHER INFORMATION: Synthetic sequence

<400> SEQUENCE: 141

```
Ser Tyr Glu Leu Thr Gln Pro Leu Ser Val Ser Val Ala Leu Gly Gln
1               5                   10                  15
```

```
Thr Ala Arg Ile Thr Cys Glu Gly Asn Asn Ile Gly Ser Lys Ala Val
            20                  25                  30

His Trp Tyr Gln Gln Lys Pro Gly Leu Ala Pro Val Leu Val Ile Tyr
        35                  40                  45

Asp Asp Asp Glu Arg Pro Ser Gly Ile Pro Glu Arg Phe Ser Gly Ser
    50                  55                  60

Asn Ser Gly Asn Thr Ala Thr Leu Thr Ile Ser Arg Ala Gln Ala Gly
65                  70                  75                  80

Asp Glu Ala Asp Tyr Tyr Cys Gln Val Trp Asp Ser Ser Ala Tyr Val
                85                  90                  95

Phe Gly Gly Gly Thr Gln Leu Thr Val Leu Gly
            100                 105

<210> SEQ ID NO 142
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 142

Leu Pro Xaa Ser Gly
1               5

<210> SEQ ID NO 143
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 143

Leu Pro Xaa Ala Gly
1               5

<210> SEQ ID NO 144
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 144

Leu Pro Xaa Thr Gly
1               5

<210> SEQ ID NO 145
<211> LENGTH: 5
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
```

```
<223> OTHER INFORMATION: X is any amino acid residue

<400> SEQUENCE: 145

Leu Ala Xaa Thr Gly
1               5

<210> SEQ ID NO 146
<211> LENGTH: 5
<212> TYPE: PRT
<213> ORGANISM: Artificial sequence
<220> FEATURE:
<223> OTHER INFORMATION: Synthetic sequence

<400> SEQUENCE: 146

Asn Pro Gln Thr Gly
1               5

<210> SEQ ID NO 147
<211> LENGTH: 4
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (3)..(3)
<223> OTHER INFORMATION: X is any amino acid residue

<400> SEQUENCE: 147

Leu Pro Xaa Thr
1

<210> SEQ ID NO 148
<211> LENGTH: 460
<212> TYPE: PRT
<213> ORGANISM: Artificial sequence
<220> FEATURE:
<223> OTHER INFORMATION: Synthetic sequence

<400> SEQUENCE: 148

Glu Ile Gln Leu Gln Gln Ser Gly Pro Val Leu Val Lys Pro Gly Ala
1               5                   10                  15

Ser Val Lys Val Ser Cys Lys Ala Ser Gly Tyr Ala Phe Thr Ala Tyr
            20                  25                  30

Asn Ile His Trp Val Arg Gln Ser His Gly Lys Arg Leu Glu Trp Ile
        35                  40                  45

Gly Ser Phe Asp Pro Tyr Asp Gly Gly Ser Ser Tyr Asn Gln Lys Phe
    50                  55                  60

Lys Asp Lys Ala Thr Leu Thr Val Asp Lys Ser Ser Thr Thr Ala Tyr
65                  70                  75                  80

Met His Leu Asn Ser Leu Thr Ser Glu Asp Ser Ala Val Tyr Tyr Cys
                85                  90                  95

Ala Arg Gly Trp Tyr Tyr Phe Asp Tyr Trp Gly His Gly Thr Thr Leu
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

Gly Leu Tyr Ser Leu Ser Ser Val Val Thr Val Pro Ser Ser Ser Leu
                180                 185                 190

Gly Thr Gln Thr Tyr Ile Cys Asn Val Asn His Lys Pro Ser Asn Thr
            195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys Leu Pro
        435                 440                 445

Glu Thr Gly Gly Trp Ser His Pro Gln Phe Glu Lys
    450                 455                 460

<210> SEQ ID NO 149
<211> LENGTH: 233
<212> TYPE: PRT
<213> ORGANISM: Artificial sequence
<220> FEATURE:
<223> OTHER INFORMATION: Synthetic sequence

<400> SEQUENCE: 149

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Ile Pro Ser Arg Phe Arg Gly
    50                  55                  60

Ser Gly Ser Gly Thr Asp Phe Thr Leu Thr Ile Ser Ser Leu Glu Pro
65                  70                  75                  80

```
Glu Asp Phe Ala Met Tyr Tyr Cys Gln Gln His Asp Glu Ser Pro Tyr
                85                  90                  95

Thr Phe Gly Glu Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Leu Pro Glu Thr Gly
    210                 215                 220

Gly Trp Ser His Pro Gln Phe Glu Lys
225                 230
```

<210> SEQ ID NO 150
<211> LENGTH: 462
<212> TYPE: PRT
<213> ORGANISM: Artificial sequence
<220> FEATURE:
<223> OTHER INFORMATION: Synthetic sequence

<400> SEQUENCE: 150

```
Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ser Asp Tyr
            20                  25                  30

Glu Met His Trp Val Ile Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Gly Tyr Tyr Asp Tyr Asp Ser Phe Thr Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205
```

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

Leu Pro Glu Thr Gly Gly Trp Ser His Pro Gln Phe Glu Lys
450                 455                 460

<210> SEQ ID NO 151
<211> LENGTH: 233
<212> TYPE: PRT
<213> ORGANISM: Artificial sequence
<220> FEATURE:
<223> OTHER INFORMATION: Synthetic sequence

<400> SEQUENCE: 151

Asp Ile Val Met Thr Gln Ser Gln Lys Ile Met Ser Thr Thr Val Gly
1               5                   10                  15

Asp Arg Val Ser Ile Thr Cys Lys Ala Ser Gln Asn Val Asp Ala Ala
            20                  25                  30

Val Ala Trp Tyr Gln Gln Lys Pro Gly Gln Ser Pro Lys Leu Leu Ile
        35                  40                  45

Tyr Ser Ala Ser Asn Arg Tyr Thr Gly Val Pro Asp Arg Phe Thr Gly
    50                  55                  60

Ser Gly Ser Gly Thr Asp Phe Thr Leu Thr Ile Ser Asn Met Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Leu Pro Glu Thr Gly Gly
    210                 215                 220

Gly Trp Ser His Pro Gln Phe Glu Lys
225                 230

<210> SEQ ID NO 152
<211> LENGTH: 462
<212> TYPE: PRT
<213> ORGANISM: Artificial sequence
<220> FEATURE:
<223> OTHER INFORMATION: Synthetic sequence

<400> SEQUENCE: 152

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
                20                  25                  30

Glu Met His Trp Val Arg Gln Ala Pro Gly Gln Gly Leu Glu Trp Leu
            35                  40                  45

Gly Ala Ile Asp Pro Glu Thr Gly Gly Thr Ala Tyr Asn Gln Lys Phe
        50                  55                  60

Lys Gly Arg Val Thr Met Thr Gly Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Thr Gly Tyr Tyr Asp Tyr Asp Ser Phe Thr Tyr Trp Gly Gln Gly Thr
                100                 105                 110

Leu Val Ser Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240
```

```
Val Phe Leu Phe Pro Pro Lys Pro Lys Asp Thr Leu Met Ile Ser Arg
            245                 250                 255

Thr Pro Glu Val Thr Cys Val Val Asp Val Ser His Glu Asp Pro
        260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

Leu Pro Glu Thr Gly Gly Trp Ser His Pro Gln Phe Glu Lys
    450                 455                 460

<210> SEQ ID NO 153
<211> LENGTH: 233
<212> TYPE: PRT
<213> ORGANISM: Artificial sequence
<220> FEATURE:
<223> OTHER INFORMATION: Synthetic sequence

<400> SEQUENCE: 153

Asp Ile Gln Met Thr Gln Ser Pro Ser Ser Leu Ser Thr Ser Val Gly
1               5                   10                  15

Asp Arg Val Thr Ile Thr Cys Lys Ala Ser Gln Asn Val Asp Ala Ala
            20                  25                  30

Val Ala Trp Tyr Gln Gln Lys Pro Gly Lys Ala Pro Lys Leu Leu Ile
        35                  40                  45

Tyr Ser Ala Ser Asn Arg Tyr Thr Gly Val Ala Ser Arg Phe Ser Gly
    50                  55                  60

Ser Gly Ser Gly Thr Asp Phe Thr Phe Thr Ile Ser Ser Leu Gln Ser
65                  70                  75                  80

Glu Asp Leu Ala Asp Tyr Phe Cys Gln Gln Tyr Asp Ile Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Leu Pro Glu Thr Gly
    210                 215                 220

Gly Trp Ser His Pro Gln Phe Glu Lys
225                 230

<210> SEQ ID NO 154
<211> LENGTH: 460
<212> TYPE: PRT
<213> ORGANISM: Artificial sequence
<220> FEATURE:
<223> OTHER INFORMATION: Synthetic sequence

<400> SEQUENCE: 154

Gln Ser Val Lys Glu Ser Gly Asp Leu Val Thr Pro Ala Gly Asn
1               5                   10                  15

Leu Thr Leu Thr Cys Thr Ala Ser Gly Ser Asp Ile Asn Asp Tyr Pro
            20                  25                  30

Ile Ser Trp Val Arg Gln Ala Pro Gly Lys Gly Leu Glu Trp Ile Gly
        35                  40                  45

Phe Ile Asn Ser Gly Gly Ser Thr Trp Tyr Ala Ser Trp Val Lys Gly
    50                  55                  60

Arg Phe Thr Ile Ser Arg Thr Ser Thr Val Asp Leu Lys Met Thr
65                  70                  75                  80

Ser Leu Thr Thr Asp Asp Thr Ala Thr Tyr Phe Cys Ala Arg Gly Tyr
            85                  90                  95

Ser Thr Tyr Tyr Gly Asp Phe Asn Ile Trp Gly Pro Gly Thr Leu Val
            100                 105                 110

Thr Ile Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
            165                 170                 175

Gly Leu Tyr Ser Leu Ser Ser Val Val Thr Val Pro Ser Ser Ser Leu
        180                 185                 190

Gly Thr Gln Thr Tyr Ile Cys Asn Val Asn His Lys Pro Ser Asn Thr
    195                 200                 205

Lys Val Asp Lys Lys Val Glu Pro Lys Ser Cys Asp Lys Thr His Thr
210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
                275                 280                 285

Lys Pro Arg Glu Gln Tyr Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys Leu Pro
                435                 440                 445

Glu Thr Gly Gly Trp Ser His Pro Gln Phe Glu Lys
                450                 455                 460

<210> SEQ ID NO 155
<211> LENGTH: 236
<212> TYPE: PRT
<213> ORGANISM: Artificial sequence
<220> FEATURE:
<223> OTHER INFORMATION: Synthetic sequence

<400> SEQUENCE: 155

Glu Leu Val Met Thr Gln Thr Pro Ser Ser Ser Gly Ala Val Gly
1               5                   10                  15

Gly Thr Val Thr Ile Asn Cys Gln Ala Ser Gln Ser Ile Asp Ser Asn
                20                  25                  30

Leu Ala Trp Phe Gln Gln Lys Pro Gly Gln Pro Pro Thr Leu Leu Ile
            35                  40                  45

Tyr Arg Ala Ser Asn Leu Ala Ser Gly Val Pro Ser Arg Phe Ser Gly
        50                  55                  60

Ser Arg Ser Gly Thr Glu Tyr Thr Leu Thr Ile Ser Gly Val Gln Arg
65                  70                  75                  80

Glu Asp Ala Ala Thr Tyr Tyr Cys Leu Gly Gly Val Gly Asn Val Ser
                85                  90                  95

Tyr Arg Thr Ser Phe Gly Gly Gly Thr Glu Val Val Lys Arg Thr
            100                 105                 110

Val Ala Ala Pro Ser Val Phe Ile Phe Pro Pro Ser Asp Glu Gln Leu
            115                 120                 125

Lys Ser Gly Thr Ala Ser Val Val Cys Leu Leu Asn Asn Phe Tyr Pro
        130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175
```

```
Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
            195                 200                 205

Thr Lys Ser Phe Asn Arg Gly Glu Cys Gly Gly Gly Ser Leu Pro
        210                 215                 220

Glu Thr Gly Gly Trp Ser His Pro Gln Phe Glu Lys
225                 230                 235

<210> SEQ ID NO 156
<211> LENGTH: 465
<212> TYPE: PRT
<213> ORGANISM: Artificial sequence
<220> FEATURE:
<223> OTHER INFORMATION: Synthetic sequence

<400> SEQUENCE: 156

Gln Glu Gln Leu Val Glu Ser Gly Gly Arg Leu Val Thr Pro Gly Gly
1               5                   10                  15

Ser Leu Thr Leu Ser Cys Lys Ala Ser Gly Phe Asp Phe Ser Ala Tyr
            20                  25                  30

Tyr Met Ser Trp Val Arg Gln Ala Pro Gly Lys Gly Leu Glu Trp Ile
        35                  40                  45

Ala Thr Ile Tyr Pro Ser Ser Gly Lys Thr Tyr Tyr Ala Thr Trp Val
    50                  55                  60

Asn Gly Arg Phe Thr Ile Ser Ser Asp Asn Ala Gln Asn Thr Val Asp
65                  70                  75                  80

Leu Gln Met Asn Ser Leu Thr Ala Ala Asp Arg Ala Thr Tyr Phe Cys
                85                  90                  95

Ala Arg Asp Ser Tyr Ala Asp Asp Gly Ala Leu Phe Asn Ile Trp Gly
            100                 105                 110

Pro Gly Thr Leu Val Thr Ile Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300
```

```
Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys Leu Pro Glu Thr Gly Gly Trp Ser His Pro Gln Phe Glu
    450                 455                 460

Lys
465

<210> SEQ ID NO 157
<211> LENGTH: 236
<212> TYPE: PRT
<213> ORGANISM: Artificial sequence
<220> FEATURE:
<223> OTHER INFORMATION: Synthetic sequence

<400> SEQUENCE: 157

Glu Leu Val Leu Thr Gln Ser Pro Ser Val Ser Ala Ala Leu Gly Ser
1               5                   10                  15

Pro Ala Lys Ile Thr Cys Thr Leu Ser Ser Ala His Lys Thr Asp Thr
            20                  25                  30

Ile Asp Trp Tyr Gln Gln Leu Gln Gly Glu Ala Pro Arg Tyr Leu Met
        35                  40                  45

Gln Val Gln Ser Asp Gly Ser Tyr Thr Lys Arg Pro Gly Val Pro Asp
    50                  55                  60

Arg Phe Ser Gly Ser Ser Ser Gly Ala Asp Arg Tyr Leu Ile Ile Pro
65                  70                  75                  80

Ser Val Gln Ala Asp Asp Glu Ala Asp Tyr Tyr Cys Gly Ala Asp Tyr
                85                  90                  95

Ile Gly Gly Tyr Val Phe Gly Gly Gly Thr Gln Leu Thr Val Thr Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190
```

```
His Lys Ser Tyr Ser Cys Gln Val Thr His Glu Gly Ser Thr Val Glu
        195                 200                 205

Lys Thr Val Ala Pro Thr Glu Cys Ser Gly Gly Gly Ser Leu Pro
210                 215                 220

Glu Thr Gly Gly Trp Ser His Pro Gln Phe Glu Lys
225                 230                 235

<210> SEQ ID NO 158
<211> LENGTH: 450
<212> TYPE: PRT
<213> ORGANISM: Artificial sequence
<220> FEATURE:
<223> OTHER INFORMATION: Synthetic sequence

<400> SEQUENCE: 158

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320
```

```
Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 159
<211> LENGTH: 214
<212> TYPE: PRT
<213> ORGANISM: Artificial sequence
<220> FEATURE:
<223> OTHER INFORMATION: Synthetic sequence

<400> SEQUENCE: 159

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 160
<211> LENGTH: 461
<212> TYPE: PRT
<213> ORGANISM: Artificial sequence
<220> FEATURE:
<223> OTHER INFORMATION: Synthetic sequence

<400> SEQUENCE: 160

| | | | | | | | | | | | | | | | |
|---|---|---|---|---|---|---|---|---|---|---|---|---|---|---|---|
| Gln | Ile | Gln | Leu | Gln | Gln | Ser | Gly | Pro | Glu | Val | Val | Lys | Pro | Gly | Ala |
| 1 | | | | 5 | | | | | 10 | | | | | 15 | |
| Ser | Val | Lys | Ile | Ser | Cys | Lys | Ala | Ser | Gly | Tyr | Thr | Phe | Thr | Asp | Tyr |
| | | | 20 | | | | | 25 | | | | | 30 | | |
| Tyr | Ile | Thr | Trp | Val | Lys | Gln | Lys | Pro | Gly | Gln | Gly | Leu | Glu | Trp | Ile |
| | | | | 35 | | | | | 40 | | | | 45 | | |
| Gly | Trp | Ile | Tyr | Pro | Gly | Ser | Gly | Asn | Thr | Lys | Tyr | Asn | Glu | Lys | Phe |
| 50 | | | | | 55 | | | | | 60 | | | | | |
| Lys | Gly | Lys | Ala | Thr | Leu | Thr | Val | Asp | Thr | Ser | Ser | Thr | Ala | Phe | |
| 65 | | | | 70 | | | | | 75 | | | | | 80 | |
| Met | Gln | Leu | Ser | Ser | Leu | Thr | Ser | Glu | Asp | Thr | Ala | Val | Tyr | Phe | Cys |
| | | | | 85 | | | | | 90 | | | | | 95 | |
| Ala | Asn | Tyr | Gly | Asn | Tyr | Trp | Phe | Ala | Tyr | Trp | Gly | Gln | Gly | Thr | Gln |
| | | | 100 | | | | | 105 | | | | | 110 | | |
| Val | Thr | Val | Ser | Ala | Ala | Ser | Thr | Lys | Gly | Pro | Ser | Val | Phe | Pro | Leu |
| | | | 115 | | | | | 120 | | | | | 125 | | |
| Ala | Pro | Ser | Ser | Lys | Ser | Thr | Ser | Gly | Gly | Thr | Ala | Ala | Leu | Gly | Cys |
| | | 130 | | | | | 135 | | | | | 140 | | | |
| Leu | Val | Lys | Asp | Tyr | Phe | Pro | Glu | Pro | Val | Thr | Val | Ser | Trp | Asn | Ser |
| 145 | | | | | 150 | | | | | 155 | | | | | 160 |
| Gly | Ala | Leu | Thr | Ser | Gly | Val | His | Thr | Phe | Pro | Ala | Val | Leu | Gln | Ser |
| | | | | 165 | | | | | 170 | | | | | 175 | |
| Ser | Gly | Leu | Tyr | Ser | Leu | Ser | Ser | Val | Val | Thr | Val | Pro | Ser | Ser | Ser |
| | | | 180 | | | | | 185 | | | | | 190 | | |
| Leu | Gly | Thr | Gln | Thr | Tyr | Ile | Cys | Asn | Val | Asn | His | Lys | Pro | Ser | Asn |
| | | | 195 | | | | | 200 | | | | | 205 | | |
| Thr | Lys | Val | Asp | Lys | Lys | Val | Glu | Pro | Lys | Ser | Cys | Asp | Lys | Thr | His |
| | | 210 | | | | | 215 | | | | | 220 | | | |
| Thr | Cys | Pro | Pro | Cys | Pro | Ala | Pro | Glu | Leu | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | His | Glu | Asp | Pro | Glu |
| | | | 260 | | | | | 265 | | | | | 270 | | |
| Val | Lys | Phe | Asn | Trp | Tyr | Val | Asp | Gly | Val | Glu | Val | His | Asn | Ala | Lys |
| | | | | 275 | | | | | 280 | | | | | 285 | |
| Thr | Lys | Pro | Arg | Glu | Glu | Gln | Tyr | Asn | Ser | Thr | Tyr | Arg | Val | Val | Ser |
| | | | 290 | | | | | 295 | | | | | 300 | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Ala | Leu | Pro | Ala | Pro | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Arg | Asp | Glu | Leu | Thr | Lys | Asn | Gln | Val | Ser | Leu | Thr | Cys | Leu |
| | | | 355 | | | | | 360 | | | | | 365 | | |

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly Lys Leu
            435                 440                 445

Pro Glu Thr Gly Gly Trp Ser His Pro Gln Phe Glu Lys
            450                 455                 460

<210> SEQ ID NO 161
<211> LENGTH: 237
<212> TYPE: PRT
<213> ORGANISM: Artificial sequence
<220> FEATURE:
<223> OTHER INFORMATION: Synthetic sequence

<400> SEQUENCE: 161

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys Gly Gly Gly Gly Ser Leu
    210                 215                 220

Pro Glu Thr Gly Gly Trp Ser His Pro Gln Phe Glu Lys
225                 230                 235

<210> SEQ ID NO 162
<211> LENGTH: 19
<212> TYPE: PRT
<213> ORGANISM: Artificial sequence

```
<220> FEATURE:
<223> OTHER INFORMATION: Synthetic sequence

<400> SEQUENCE: 162

Met Asn Phe Gly Leu Arg Leu Ile Phe Leu Val Leu Thr Leu Lys Gly
1               5                   10                  15

Val Gln Cys

<210> SEQ ID NO 163
<211> LENGTH: 9
<212> TYPE: PRT
<213> ORGANISM: Artificial sequence
<220> FEATURE:
<223> OTHER INFORMATION: Synthetic sequence

<400> SEQUENCE: 163

Gly Trp Ser His Pro Gln Phe Glu Lys
1               5
```

ROR1 ANTIBODY COMPOSITIONS AND RELATED METHODS

CROSS-REFERENCE TO RELATED APPLICATIONS

The subject patent application is a continuation of U.S. patent application Ser. No. 16/040,244 (filed Jul. 19, 2018), which is a continuation of PCT Patent Application No. 2017/014311 (filed Jan. 20, 2017), which claims the benefit of priority to U.S. Provisional Patent Application No. 62/280,843 (filed Jan. 20, 2016). The full disclosures of the priority applications are incorporated herein by reference in their entirety and for all purposes.

BACKGROUND OF THE INVENTION

Cancer is one of the leading causes of death. It is a class of diseases which is caused by malignant transformation of healthy cells, caused by genetic alterations, like chromosomal translocations, mutations in tumor suppressor genes, transcription factors or growth-factor receptors, leading to the immortalization of the cells. If the immortalization is combined with excessive proliferation the immortalized cells generate tumors with or without metastasis (in case of solid tumors) or leukemias and lymphomas (cancers of the blood). Defective apoptosis, or programmed cell death, can further contribute to malignant transformation of cells leading to cancer.

A family of membrane associated receptor tyrosine kinases, consisting of the receptor tyrosine kinase orphan receptors-1 and -2 (ROR1 and ROR2) have been described as being specifically associated with particular cancers (Rebagay et al. (2012) *Front Oncol.* 2(34)), while being largely absent in expression on healthy tissue with few exceptions (Balakrishnan et al. (2016) *Clin Cancer Res.* doi: 10.1158/1078-0432). Whether or not ROR expression is functionally associated with tumorigenesis remains unclear. However, due to the very tumor-selective expression of the ROR family members, they represent relevant targets for targeted cancer therapies. Receptor tyrosine kinase orphan receptors-1 (ROR1) is of particular interest as a cancer target, due to its nearly 100% association with chronic lymphocytic leukemia (CLL) (Cui et al. (2016) *Blood* 128(25), p. 2931) and the observation that is also expressed in certain solid tumors, like that of lung and breast (Balakrishnan et al. (2016) *Clin Cancer Res.* doi: 10.1158/1078-0432). Members of the ROR family are type-I transmembrane proteins containing three distinct extracellular domains, an Ig, a Kringle and a Frizzled domain, followed a transmembrane spanning region, and an intracellular portion. Within the intracellular portion, ROR1 possesses a tyrosine kinase domain, two serine/threonine-rich domains and a proline-rich domain. RORs have been studied in the context of embryonic patterning and neurogenesis through a variety of homologs. These physiologic functions are dichotomous based on the requirement of the kinase domain. A growing literature has established ROR1 as a marker for cancer, such as in chronic lymphocytic leukemia (CLL) for which ROR1 expression is nearly 100% correlated, some acute lymphoblastic leukemias (ALL), mantle cell lymphomas, and some other blood malignancies. In addition, ROR1 is critically involved in progression of a number of solid tumors, such as in neuroblastoma, sarcoma, renal cell carcinoma, breast cancer, lung cancer, colon cancer, head and neck cancer, melanoma, and other cancers. ROR1 has been shown to inhibit apoptosis, potentiate EGFR signaling, induce epithelial-mesenchymal transition (EMT), and contribute to caveolae formation. Importantly, ROR1 is mainly detectable in embryonic tissue and generally absent in adult tissue, making the protein an ideal drug target for cancer therapy. As such, ROR1 has previously been recognized as a target for the development of ROR1 specific antibodies. However, due to the high homology of ROR1 between different mammalian species, which is 100% conserved on the amino acid level between humans and cynomolgus monkeys, 96.7% homologous between human and mouse, and 96.3% homologous between human and rabbit, it has been difficult to raise high affinity antibodies against this target by standard technologies, like animal immunizations.

A few murine and rabbit antibodies have been discussed in the literature. For example, WO 2007/051077 discussed monoclonal antibodies, including humanized antibodies, directed against native ROR1 found on lymphomas including CLL, small lymphocytic lymphoma, marginal B-cell lymphoma and Burkett's lymphoma. Methods for inhibiting growth of a tumor cell using agents, which may be ROR1-binding antibodies that inhibit ROR1 kinase activity, are the subject of WO 2007/146957. WO 2011/054007 discussed a method of treatment or prophylaxis of cancer in which the extracellular domain of ROR1 is expressed by administration of specific ROR1-targeting antibodies.

Additionally, WO 2010/124188 discussed anti-human ROR1 antibodies, and in particular to monoclonal murine antibody referred to under the name 2A2, while WO 2012/075158 refers to monoclonal rabbit antibodies named R11 and R12. Particular ROR1-targeting antibodies are also mentioned in WO 2016/094873. Both WO 2011/079902 and WO 2012/076066 discussed biological inhibitors of ROR1 capable of inducing cell death that bind to selected extracellular ROR1 domain sequences. WO 2014/031174 refers to anti-ROR1 antibodies having the same binding specificity as an antibody named 99961. Binding epitopes of anti-ROR1 antibodies are further referred to in WO 2016/187220. WO 2011/159847 discussed particular scFv antibody fragment conjugates that bind ROR1. WO 2014/167022, WO 2016/055592 and WO 2016/055593 discussed bispecific ROR1-targeting antibodies and their uses, while WO 2015/184203 discussed tri-specific binding molecules. Especially newer documents disclosing humanized anti-ROR1 monoclonal antibodies are based on the originally disclosed mouse or rabbit antibodies, like 2A2, R11, R12 or D10.

Due to the low number of available ROR1 specific monoclonal antibodies, there is a need in the art for better anti-ROR1 antibodies that have higher affinity or other functional properties not possessed by the known antibody clones. There is also a need for additional diagnostic tools for detecting ROR1 expressions in ROR1-related disease conditions by, e.g., Western blotting and/or immunohistochemistry (IHC). The instant invention is directed to addressing these and other needs.

SUMMARY OF THE INVENTION

In one aspect, the invention provides novel, high-affinity binding domains of rabbit antibodies that specifically bind to the extracellular domain of human receptor tyrosine kinase-like orphan receptor 1 (hROR1) and that have been selected from highly diverse phage-display libraries of non-immunized rabbits using human ROR1 (hROR1) extracellular domains expressed in mammalian cells as a bait. The variable regions of rabbit antibodies have been selected by screening for the binding against the ECD of hROR1 both as recombinant proteins and also based on the binding of hROR1 over-expressed on the surface of mammalian host cells. By this strategy novel antibodies for hROR1 of unprecedented quality and favorable functional properties have been identified. Furthermore, the invention provides chimeric full-length antibodies of the rabbit variable domains fused to the constant region domains of human IgG$_1$ antibodies. Furthermore the invention provides novel, high-affinity humanized antibodies that were generated by CDR grafting of the rabbit anti-ROR1 antibodies disclosed herein into the framework of variable immunoglobulin heavy and light chains. Such humanized antibodies can be used for the therapy of human diseases due to the high homology of said humanized antibodies to endogenous, fully human antibodies. In a second aspect of the invention site-specifically conjugated antibody drug conjugates (ADCs) based on the chimeric rabbit-human and humanized anti-human ROR1 (hROR1) antibodies with an ultra-potent anthracycline toxin are provided by the invention. The site-specific conjugation is achieved by enzymatic conjugation using sortase enzyme, essentially as disclosed in WO2014140317, which is incorporated as reference herein. The ultra-potent anthracycline toxin resulting in anti-hROR1 ADCs with unprecedented potency in various in vitro and in vivo tumor models has been disclosed in WO2016102679, which is incorporated as reference herein.

Lastly, the invention provides chimeric antigen receptors (CARs) and T cells engineered with these CARs, i.e. so-called CAR-T cells, employing said anti-hROR1 binding domains showing high efficacy in vitro.

Therefore the invention relates to anti-hROR1 antibodies, antibody-based binding proteins, antibody fragments thereof, antibody drug conjugates (ADCs), or CARs having the same binding specificity for hROR1 as that of hROR1 specific antibodies containing an immunoglobulin heavy chain variable region sequence and an immunoglobulin light chain variable region sequence, respectively, shown in (1) SEQ ID NO:1 and SEQ ID NO:14; (2) SEQ ID NO:2 and SEQ ID NO:15; (3) SEQ ID NO:3 and SEQ ID NO:16; (4) SEQ ID NO:4 and SEQ ID NO:17; (5) SEQ ID NO:5 and SEQ ID NO:18; (6) SEQ ID NO:6 and SEQ ID NO:19; (7) SEQ ID NO:7 and SEQ ID NO:20; (8) SEQ ID NO:8 and SEQ ID NO:21; (9) SEQ ID NO:9 and SEQ ID NO:22; (10) SEQ ID NO:10 and SEQ ID NO:23; (11) SEQ ID NO:11 and SEQ ID NO:24; (12) SEQ ID NO:12 and SEQ ID NO:25; (13) SEQ ID NO:13 and SEQ ID NO:26; (14) SEQ ID NO:130 and SEQ ID NO:136; (15) SEQ ID NO:131 and SEQ ID NO:137; (16) SEQ ID NO:132 and SEQ ID NO:138; (17) SEQ ID NO:133 and SEQ ID NO:139; (18) SEQ ID NO:134 and SEQ ID NO:140; or (19) SEQ ID NO:135 and SEQ ID NO:141.

The invention further relates to anti-hROR1 antibodies, antibody-based binding proteins, antibody fragments thereof, antibody drug conjugates (ADCs), or CARs comprising immunoglobulin heavy chain CDR sequences and immunoglobulin light chain CDR sequences that are at least 90%, or at least 95% or greater than 95%, but less than 100% identical, respectively, to (1) SEQ ID NOs:27-29 and SEQ ID NOs:66-68, (2) SEQ ID NOs:30-32 and SEQ ID NOs:69-71, (3) SEQ ID NOs:33-35 and SEQ ID NOs:72-74, (4) SEQ ID NOs:36-38 and SEQ ID NOs:75-77, (5) SEQ ID NOs:39-41 and SEQ ID NOs:78-80, (6) SEQ ID NOs:42-44 and SEQ ID NOs:81-83, (7) SEQ ID NOs:45-47 and SEQ ID NOs:84-86, (8) SEQ ID NOs:48-50 and SEQ ID NOs:87-89, (9) SEQ ID NOs:51-53 and SEQ ID NOs:90-92, (10) SEQ ID NOs:54-56 and SEQ ID NOs:93-95, (11) SEQ ID NOs:57-59 and SEQ ID NOs:96-98, (12) SEQ ID NOs:60-62 and SEQ ID NOs:99-101, or (13) SEQ ID NOs:63-65 and SEQ ID NOs:102-104.

The invention further relates to anti-hROR1 antibodies, antibody-based binding proteins, antibody fragments thereof, antibody drug conjugates (ADCs), or CARs comprising immunoglobulin heavy chain CDR sequences and immunoglobulin light chain CDR sequences that are identical, respectively, to (1) SEQ ID NOs:27-29 and SEQ ID NOs:66-68, (2) SEQ ID NOs:30-32 and SEQ ID NOs:69-71, (3) SEQ ID NOs:33-35 and SEQ ID NOs:72-74, (4) SEQ ID NOs:36-38 and SEQ ID NOs:75-77, (5) SEQ ID NOs:39-41 and SEQ ID NOs:78-80, (6) SEQ ID NOs:42-44 and SEQ ID NOs:81-83, (7) SEQ ID NOs:45-47 and SEQ ID NOs:84-86, (8) SEQ ID NOs:48-50 and SEQ ID NOs:87-89, (9) SEQ ID NOs:51-53 and SEQ ID NOs:90-92, (10) SEQ ID NOs:54-56 and SEQ ID NOs:93-95, (11) SEQ ID NOs:57-59 and SEQ ID NOs:96-98, (12) SEQ ID NOs:60-62 and SEQ ID NOs:99-101, or (13) SEQ ID NOs:63-65 and SEQ ID NOs:102-104.

The invention further relates to anti-hROR1 antibodies, antibody-based binding proteins, antibody fragments thereof, antibody drug conjugates (ADCs), or CARs comprising either an immunoglobulin heavy chain variable region sequence or an immunoglobulin light chain variable region sequence with at least 90%, or at least 95%, or greater than 95% but less than 100% identity at amino acid level relative to an immunoglobulin heavy chain variable region sequence and an immunoglobulin light chain variable region sequence, respectively, shown in (1) SEQ ID NO:1 and SEQ ID NO:14; (2) SEQ ID NO:2 and SEQ ID NO:15; (3) SEQ ID NO:3 and SEQ ID NO:16; (4) SEQ ID NO:4 and SEQ ID NO:17; (5) SEQ ID NO:5 and SEQ ID NO:18; (6) SEQ ID NO:6 and SEQ ID NO:19; (7) SEQ ID NO:7 and SEQ ID NO:20; (8) SEQ ID NO:8 and SEQ ID NO:21; (9) SEQ ID NO:9 and SEQ ID NO:22; (10) SEQ ID NO:10 and SEQ ID NO:23; (11) SEQ ID NO:11 and SEQ ID NO:24; (12) SEQ ID NO:12 and SEQ ID NO:25; or (13) SEQ ID NO:13 and SEQ ID NO:26.

The invention further relates to anti-hROR1 antibodies, antibody-based binding proteins, antibody fragments thereof, antibody drug conjugates (ADCs), or CARs comprising an immunoglobulin heavy chain CDR sequence selected from the group consisting of SEQ ID NOs:27-65. The invention further relates to relates to anti-hROR1 antibodies, antibody fragments thereof, antibody drug conjugates (ADCs), or CARs comprising an immunoglobulin light chain CDR sequence selected from the group consisting of SEQ ID NOs:66-104. In some embodiments, the hROR1-specific antibodies, antibody-based binding proteins, or antibody fragments thereof, antibody drug conjugates (ADCs), or CARs contain heavy chain CDR1, CDR2, and CDR3 sequences that are respectively identical to SEQ ID NOs:27-29, SEQ ID NOs:30-32, SEQ ID NOs:33-35, SEQ ID NO:36-38, SEQ ID NOs:39-41, SEQ ID NOs:42-44, SEQ ID NOs:45-47, SEQ ID NOs:48-50, SEQ ID NOs:51-53, SEQ ID NOs:54-56, SEQ ID NOs:57-59, SEQ ID NOs:60-62, or SEQ ID NOs:63-65.

The invention further relates to anti-hROR1 antibodies, antibody-based binding proteins, antibody fragments thereof, antibody drug conjugates (ADCs), or CARs comprising either an immunoglobulin heavy chain variable region sequence or an immunoglobulin light chain variable region sequence identical to (1) SEQ ID NO:1 and SEQ ID NO:14; (2) SEQ ID NO:2 and SEQ ID NO:15; (3) SEQ ID NO:3 and SEQ ID NO:16; (4) SEQ ID NO:4 and SEQ ID NO:17; (5) SEQ ID NO:5 and SEQ ID NO:18; (6) SEQ ID NO:6 and SEQ ID NO:19; (7) SEQ ID NO:7 and SEQ ID NO:20; (8) SEQ ID NO:8 and SEQ ID NO:21; (9) SEQ ID NO:9 and SEQ ID NO:22; (10) SEQ ID NO:10 and SEQ ID NO:23; (11) SEQ ID NO:11 and SEQ ID NO:24; (12) SEQ ID NO:12 and SEQ ID NO:25; (13) SEQ ID NO:13 and SEQ ID NO:26; (14) SEQ ID NO:130 and SEQ ID NO:136; (15) SEQ ID NO:131 and SEQ ID NO:137; (16) SEQ ID NO:132 and SEQ ID NO:138; (17) SEQ ID NO:133 and SEQ ID NO:139; (18) SEQ ID NO:134 and SEQ ID NO:140; or (19) SEQ ID NO:135 and SEQ ID NO:141

The invention further relates to anti-hROR1 antibodies, antibody-based binding proteins, antibody fragments thereof, antibody drug conjugates (ADCs), or CARs comprising anti-hROR1 specific antibodies, antibody-based-binding proteins or antibody fragments thereof that comprise an immunoglobulin heavy chain variable region sequence and an immunoglobulin light chain variable region sequence, respectively, identical to (1) SEQ ID NO:1 and SEQ ID NO:14; (2) SEQ ID NO:2 and SEQ ID NO:15; (3) SEQ ID NO:3 and SEQ ID NO:16; (4) SEQ ID NO:4 and SEQ ID NO:17; (5) SEQ ID NO:5 and SEQ ID NO:18; (6) SEQ ID NO:6 and SEQ ID NO:19; (7) SEQ ID NO:7 and SEQ ID NO:20; (8) SEQ ID NO:8 and SEQ ID NO:21; (9) SEQ ID NO:9 and SEQ ID NO:22; (10) SEQ ID NO:10 and SEQ ID NO:23; (11) SEQ ID NO:11 and SEQ ID NO:24; (12) SEQ ID NO:12 and SEQ ID NO:25; (13) SEQ ID NO:13 and SEQ ID NO:26; (14) SEQ ID NO:130 and SEQ ID NO:136; (15) SEQ ID NO:131 and SEQ ID NO:137; (16) SEQ ID NO:132 and SEQ ID NO:138; (17) SEQ ID NO:133 and SEQ ID NO:139; (18) SEQ ID NO:134 and SEQ ID NO:140; or (19) SEQ ID NO:135 and SEQ ID NO:141.

In some embodiments, anti-hROR1 antibodies, antibody-based binding proteins, antibody fragments thereof, antibody drug conjugates (ADCs), or CARs comprise an immunoglobulin light chain CDR sequence selected from the group consisting of SEQ ID NOs:66-104. Some of these molecules further harbor an immunoglobulin heavy chain CDR sequence selected from the group consisting of SEQ ID NOs:27-65. Some of these molecules harbor immunoglobulin light chain CDR1, CDR2, and CDR3 sequences that are, respectively, identical to SEQ ID NOs:66-68, SEQ ID NOs:69-71, SEQ ID NOs:72-74, SEQ ID NO:75-77, SEQ ID NOs:78-80, SEQ ID NOs:81-83, SEQ ID NOs:84-86, SEQ ID NOs:87-89, SEQ ID NOs:90-92, SEQ ID NOs:93-95, SEQ ID NOs:96-98, SEQ ID NOs:99-101, or SEQ ID NOs:102-104. In some embodiments, the anti-hROR1 antibodies, antibody-based binding proteins, antibody fragments thereof, antibody drug conjugates (ADCs), or CARs comprise immunoglobulin heavy chain CDR1, CDR2 and CDR3 sequences and immunoglobulin light chain CDR1, CDR2 and CDR3 sequences, respectively, shown in (1) SEQ ID NOs:27-29 and SEQ ID NOs:66-68, (2) SEQ ID NOs:30-32 and SEQ ID NOs:69-71, (3) SEQ ID NOs:33-35 and SEQ ID NOs:72-74, (4) SEQ ID NOs:36-38 and SEQ ID NOs:75-77, (5) SEQ ID NOs:39-41 and SEQ ID NOs:78-80, (6) SEQ ID NOs:42-44 and SEQ ID NOs:81-83, (7) SEQ ID NOs:45-47 and SEQ ID NOs:84-86, (8) SEQ ID NOs:48-50 and SEQ ID NOs:87-89, (9) SEQ ID NOs:51-53 and SEQ ID NOs:90-92, (10) SEQ ID NOs:54-56 and SEQ ID NOs:93-95, (11) SEQ ID NOs:57-59 and SEQ ID NOs:96-98, (12) SEQ ID NOs:60-62 and SEQ ID NOs:99-101, or (13) SEQ ID NOs:63-65 and SEQ ID NOs:102-104.

The invention further relates to hROR1-specific humanized antibodies, antibody-based binding proteins, antibody fragments thereof, antibody drug conjugates (ADCs), or CARs with at least 90%, or at least 95%, or at least 95% but less than 100% homology at amino acid level to immunoglobulin heavy or immunoglobulin light chain provided of: (14) SEQ ID NO:130 and SEQ ID NO:136; (15) SEQ ID NO:131 and SEQ ID NO:137; (16) SEQ ID NO:132 and SEQ ID NO:138; (17) SEQ ID NO:133 and SEQ ID NO:139; (18) SEQ ID NO:134 and SEQ ID NO:140; or (19) SEQ ID NO:135 and SEQ ID NO:141.

In yet additional embodiments, the hROR1-specific antibodies, antibody-based binding proteins or antibody fragments thereof are either of IgA$_1$, IgA$_2$, IgD, IgE, IgG$_1$, IgG$_2$, IgG$_3$ IgG$_4$, or IgM isotypes, or F(ab)$_2$, Fv, scFv, IgGACH$_2$, F(ab')$_2$, scFv$_2$CH$_3$, Fab, V$_L$, V$_H$, scFv$_4$, scFv$_3$, scFv$_2$, dsFv, Fv, scFv-Fc, (scFv)$_2$ fragments thereof, or non-depleting IgG, diabodies or bivalent antibodies. Some of the molecules are IgGs selected from the group consisting of naturally occurring IgG$_1$, IgG$_2$, IgG$_3$, IgG$_4$ isotypes, or synthetic IgGs. Some of the molecules are Fab, scFv, or dsFv. In some embodiments, the hROR1-specific antibodies, antibody-based binding proteins or antibody fragments thereof of the invention are conjugated to a synthetic molecule. The synthetic molecule can be, e.g., a label, a cytotoxic agent, a radioisotope, or a liposome. The cytotoxic agent can be, e.g., a small molecule weight toxin, a peptide toxin, or a protein toxin. In some embodiments, the hROR1-specific antibodies, antibody-based binding proteins or antibody fragments thereof are conjugated to a transmembrane region and an intracellular T-cell receptor (TCR) signaling domain to form a chimeric antigen receptor (CAR).

The invention further relates to antibody drug conjugates (ADCs) comprising a hROR1-specific humanized or chimeric antibody, antibody-based binding protein or antibody fragment with a toxin payload that effects efficient killing of hROR1 specific cells. In said ADCs the toxin payload can be conjugated non-site-specifically to the antibody, antibody-based binding protein or antibody fragment via lysine or cysteine amino acid side chains employing classical chemical linkers with maleimide functionality, or other chemical known in the art that can mediate conjugation to lysine or cysteine amino acid side chains. In said ADCs the small molecular weight payload can also be conjugated site-specifically either by chemical, chemo-enzymatic, or enzymatic conjugations known in the art, like e.g. with bifunctional linkers, linkers allowing Pictet-Spengler chemistry on formyl-glycine forming enzyme modified antibodies, by glycan-remodeled antibodies, or by bacterial transglutaminase or sortase enzymes.

In some related aspects, the invention provides pharmaceutical compositions or kits that contain a therapeutically effective amount of an anti-hROR1 antibody, antibody-based binding protein, antibody fragment thereof, antibody drug conjugate (ADC) described herein and a pharmaceutically acceptable carrier. Some kits of the invention can additionally contain one or more immunoassay buffers. Also provided in the invention are polynucleotides encoding the variable region of the immunoglobulin heavy chain or immunoglobulin light chain of the anti-hROR1 antibodies, antibody-based binding proteins, antibody fragments thereof, antibody drug conjugates (ADCs), or CARs disclosed herein, as well as expression vectors harboring such a polynucleotide sequence.

In another aspect, the invention provides methods for killing or inhibiting the growth of a cell expressing hROR1. The methods involve administering a therapeutically effective amount of anti-hROR1 antibodies, antibody-based binding protein, antibody fragment thereof, antibody drug conjugate (ADC), or CAR of the invention to a subject in need thereof, which enables killing or inhibition of the growth of the cell expressing hROR1 in the subject. Some of these methods are specifically directed to killing or inhibiting tumor cells. In another aspect, the invention provides methods of treating a disease or condition associated with elevated expression of hROR1 in a subject. These methods entail administering a therapeutically effective amount of anti-hROR1 antibodies, antibody-based binding proteins, antibody fragments thereof, ADCs, or CARs of the invention to a subject afflicted with a disease or condition associated with elevated expression of hROR1, which allows treatment of the disease or condition associated with elevated expression of hROR1 in the subject. Some of these therapeutic methods are specifically directed to treating cancer. For example, the methods can be employed to treat subjects suffering from various types of cancer, including, e.g., CLL, ALL, mantle cell lymphoma, neuroblastoma, sarcoma, renal cell carcinoma, breast cancer, lung cancer, colon cancer, head and neck cancer, and melanoma.

In still another aspect, the invention provides methods of detecting an altered ROR1 level in a subject. Such methods involve (a) obtaining a biological sample from the subject; (b) contacting the sample with anti-hROR1 antibodies, antibody-based binding proteins or antibody fragments thereof of the invention; (c) determining the level of ROR1 in the biological sample; and (d) comparing the level of ROR1 in the biological sample to a control level of ROR1 to thereby determine whether the ROR1 level in the biological sample is altered relative to the control level of ROR1. In some of these methods, an increased ROR1 level in the subject relative to the control level is indicative of a disease or condition associated with elevated expression of ROR1 in the subject. Examples of specific diseases or conditions suitable for the methods include, e.g., CLL, ALL, mantle cell lymphoma, neuroblastoma, sarcoma, renal cell carcinoma, breast cancer, lung cancer, colon cancer, head and neck cancer, or melanoma.

In another related aspect, the invention provides methods for detecting a ROR1-expressing tumor in a subject. The methods involve (a) administering an hROR1 antibody, antibody-based binding protein or antibody fragment thereof of the invention to a subject that has, is suspected to have, or is at risk of developing a ROR1-expressing tumor; and (b) imaging the subject for a region of altered conjugated label density or concentration, wherein the density or concentration is relative to (i) background in proximal tissue or (ii) the density or concentration previously detected in the same region of the subject, such that the existence of a region of altered conjugated label density or concentration is an indication of the presence of an ROR1-expressing tumor in the subject.

A further understanding of the nature and advantages of the present invention may be realized by reference to the remaining portions of the specification and claims.

DESCRIPTION OF THE DRAWINGS

FIG. 1 shows the amino acid sequences of variable immunoglobulin heavy and light chains of novel rabbit anti-hROR1 mAbs, as indicated. The amino acid sequence alignment of the rabbit variable domains ($V_\kappa$, $V_\lambda$, and $V_H$) is shown with framework regions (FR) and complementarity determining regions (CDR) using Kabat numbering. Shown in the figure are the heavy chain variable domain sequences (SEQ ID NOs:1-13, respectively) and the light chain variable domain sequences (SEQ ID NOs:14-26, respectively) of 13 antibodies designated XBR1-402, ERR1-301, ERR1-306, ERR1-316, ERR1-324, ERR1-403, ERR1-409, ERR1-TOP4, ERR1-TOP15, ERR1-TOP22, ERR1-TOP40, ERR1-TOP43, and ERR1-TOP54. As indicated in the figure clones XBR1-402, ERR1-301, ERR1-306, ERR1-316, ERR1-403, ERR1-409, ERR1-TOP4, ERR1-TOP15, ERR1-TOP22, ERR1-TOP43, and ERR1-TOP54 are variable domains of immunoglobulin λ light chains, while antibodies ERR1-324 and ERR1-TOP40 are variable domains of immunoglobulin κ light chains.

FIG. 23 shows VH and VL amino acid sequences of humanized antibody clones derived from novel anti-ROR1 antibody XBR1-402. The amino acid sequence alignment of the humanized variable domains ($V_\lambda$ and $V_H$) is shown with framework regions (FR) and complementarity determining regions (CDR) using Kabat numbering. Shown in the figure are the heavy chain variable domain sequences (SEQ ID NOs:130-135, respectively) and the light chain variable domain sequences (SEQ ID NOs:136-141, respectively) of 6 antibodies designated HuXBR1-402(3), HuXBR1-402(8), HuXBR1-402(15), HuXBR1-402(17), HuXBR1-402(19), and HuXBR1-402(26).

FIG. 24 provides data of the affinity measurements with novel humanized clones of parental mAb XBR1-402, including $k_{on}$ and $k_{off}$ data as indicated.

DETAILED DESCRIPTION

I. Overview

The invention is predicated in part on the generation by the present inventors of a large naïve chimeric rabbit/human Fab library and selection for binders to human ROR1 via phage display. Receptor tyrosine kinase orphan receptors-1 and -2, ROR1 and ROR2, are the only two family members defining a new receptor tyrosine kinase family, based on the overall structural design and some functional similarities. Both ROR1 and ROR2 proteins are type I-single pass trans-membrane receptors with an extracellular domain (ECD) consisting of an immunoglobulin domain, a cysteine rich frizzled domain and a Kringle domain. These three extracellular domains are followed by a trans-membrane domain connecting the ECD to an intracellular portion of the protein comprising kinase domains (Rabagay et al. (2012) Frontiers Oncol. 2: 1-8). The human ROR1 and ROR2 proteins are 58% homologous between each other, but each of the ROR proteins is highly conserved between species. The most conserved is actually the ROR1 protein, a 937 aa long protein, that is over 98.5% identical between humans and all sequenced non-human primate species, and even 96.7 and 96.3% homologous between human and mouse and rabbit ROR1, respectively (Borcherding et al. (2014) Protein Cell 5: 496-502). Therefore, it has been a challenge to generate high-quality anti-ROR1 antibodies by mouse or rabbit immunizations, and there are only very few known antibodies with acceptable affinity. See, e.g., WO 2010/124188 (murine monoclonal antibody 2A2), WO 2012/075158 (rabbit antibodies R11 and R12), WO 2012/097313 (mouse monoclonal antibody D10) and WO2014/031174 (humanized versions of mouse mAb 99961, which binds the same epitope as that by mAb D10).

In order to not repeat generation of anti-ROR1 antibodies by conventional immunization/screening of mice/rabbits that would direct antibodies against epitopes of greatest divergence between mouse/rabbit ROR1 and human ROR1 (as was the case in the identification of mAbs 2A2, R11, R12, D10 and 99961), the present inventors have generated a very high-complexity naïve rabbit antibody Fab library displayed by phage and screened this library for binding to native mammalian recombinant ECD of ROR1 and to cell-surface expressed human ROR1, in order to select most functional and diverse antibody clones reactive with native human ROR1 protein. This strategy was chosen because the antibody repertoire to be mined is still derived from natural rabbit B lymphocytes and thus selected for immune-system pre-selected antibody heavy and light chains. However, due to the applied screening strategy involving native recombinant and cell-expressed human ROR1, it was the hope that hROR1 specific antibodies would be identified with good developability and functional qualities and that are particularly useful for the therapy of human diseases associated with ROR1 expression, like in particular ROR1-positive cancer.

Figure 1:
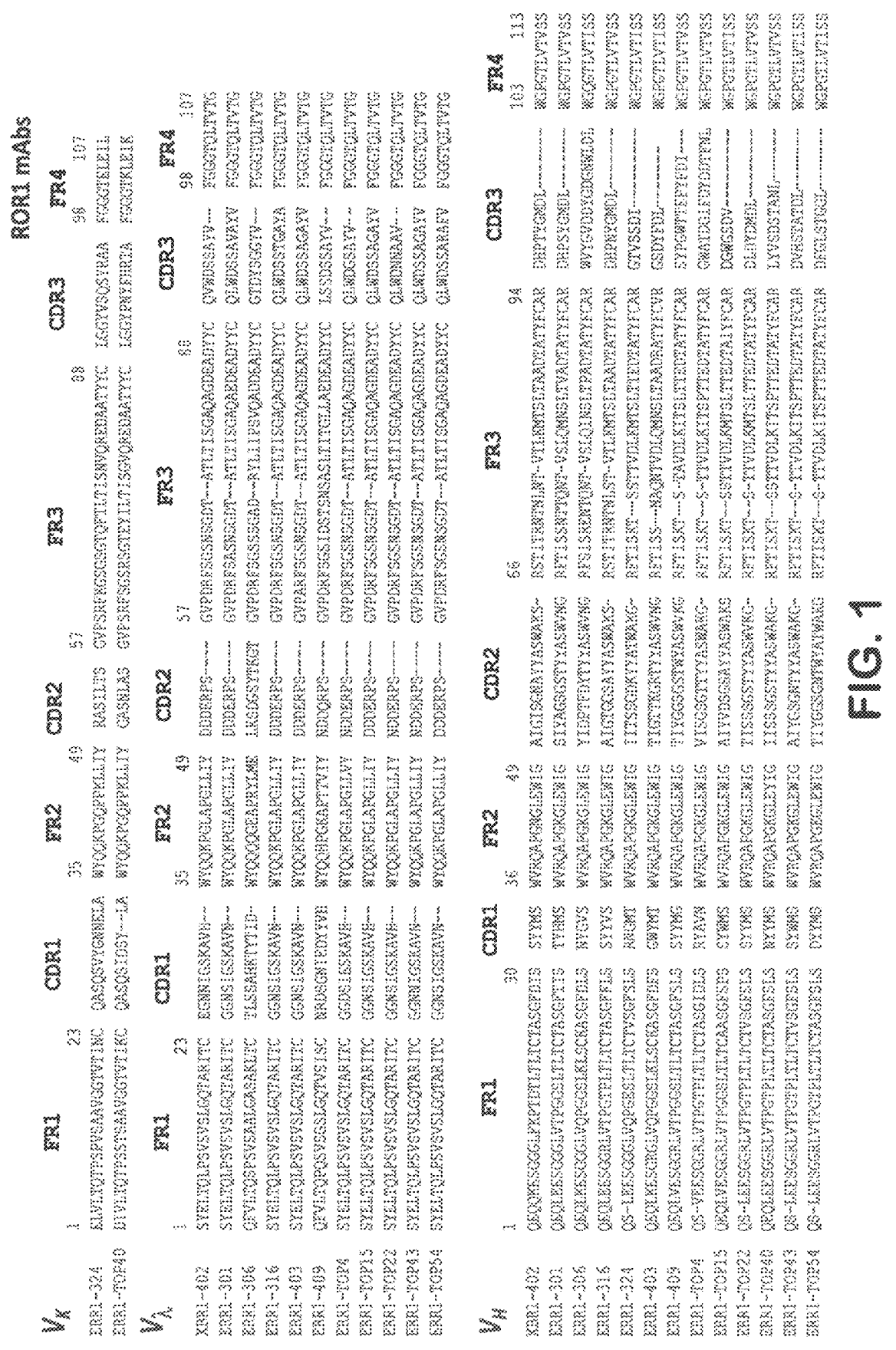
Figure 2:
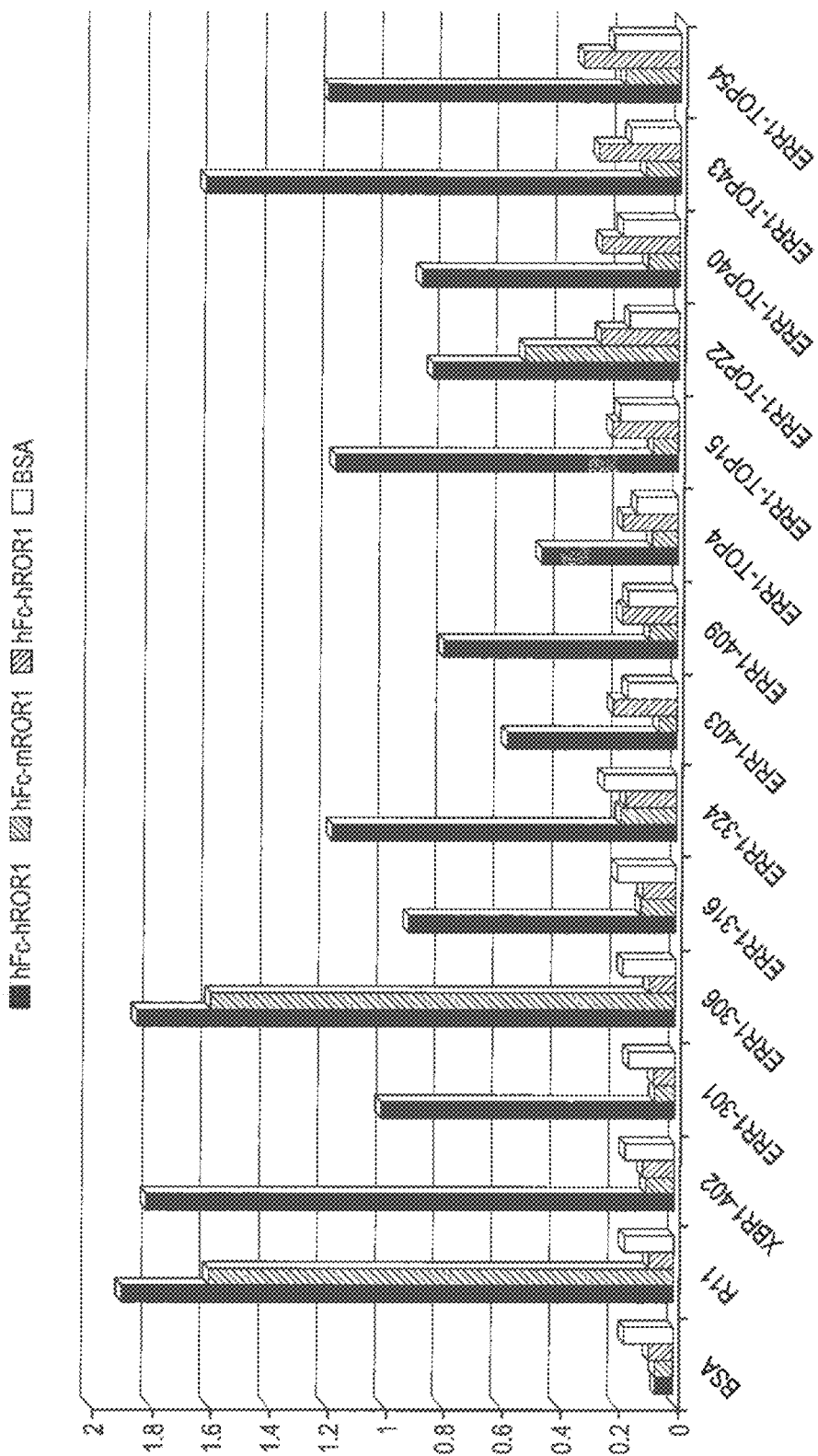
FIG. 2 shows the binding activity of chimeric rabbit/human Fabs to human ROR1 (hROR1) and mouse ROR1 (mROR1) expressed as fusion proteins of the extracellular domain (ECD) of hROR1 and mROR1 to the human Fc domain of a human IgG1 antibody. The binding of each chimeric rabbit/human Fab to hROR1 and mROR1 fused with human IgG1 Fc (hFc-hROR1 and hFc-mROR1) was analyzed by ELISA. hFc-ROR1 or hFc-mROR1 were captured by anti-human IgG1 Fc antibody immobilized on plate and then incubated with hROR1 specific Fabs comprising a His-tag via detection with mouse anti-His tag. Specificity of the Fabs was confirmed by using fusion proteins of the extracellular domain (ECD) of hROR2 with the human Fc domain of a human IgG1 antibody (hFc-hROR2) as control.
Figure 3:
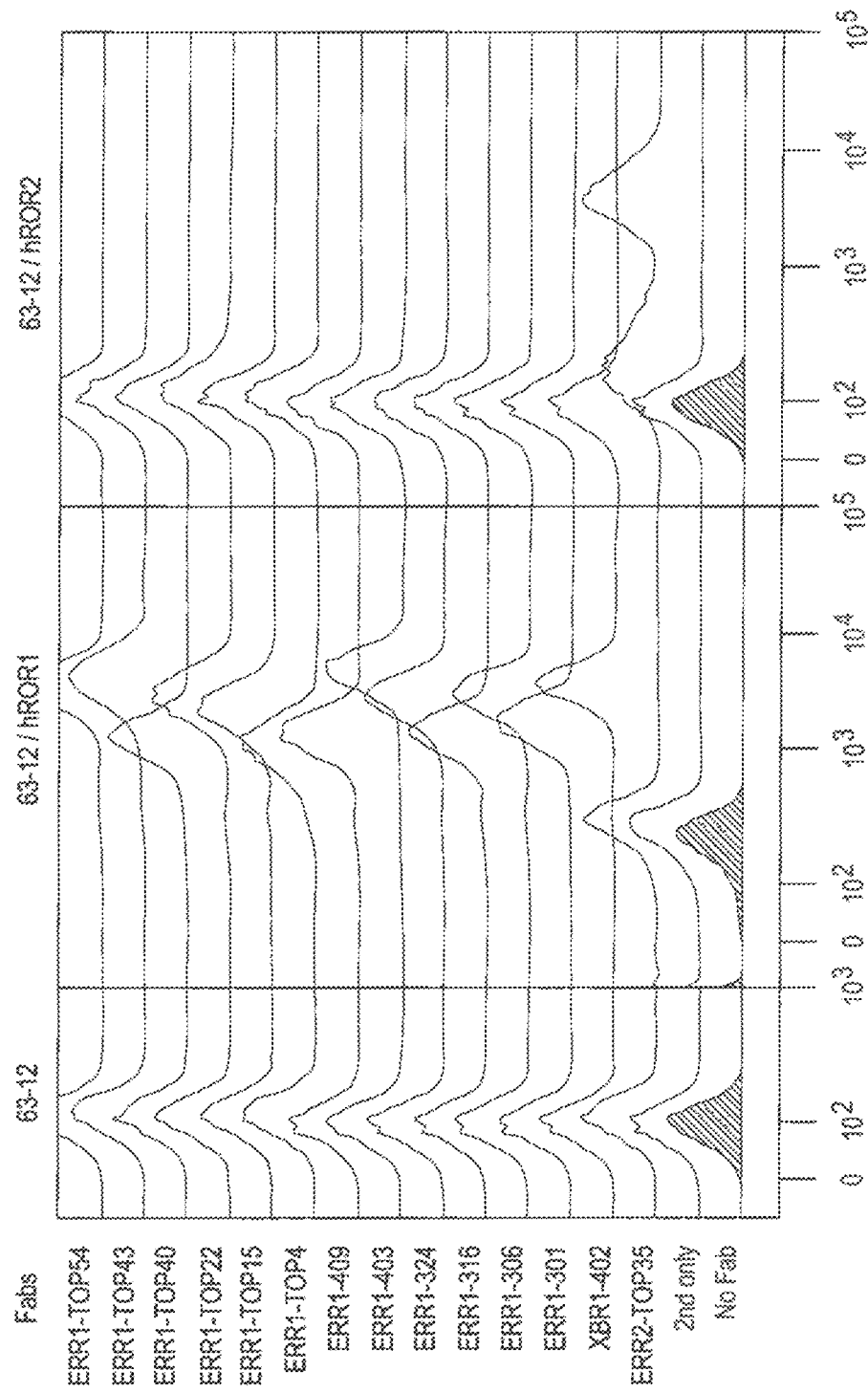
FIG. 3 shows binding activity of chimeric rabbit/human Fabs to native human ROR1 protein expressed on the cell surface of murine preB cell line 63-12 (see Example 1). The binding of each chimeric rabbit/human Fab to the ectopically expressed human ROR1 on mouse pre-B cell (63-12) surface was analyzed by flow cytometry. ERR2-TOP35 is a mAb against hROR2 that served as an isotype-matched control.
Figure 6:
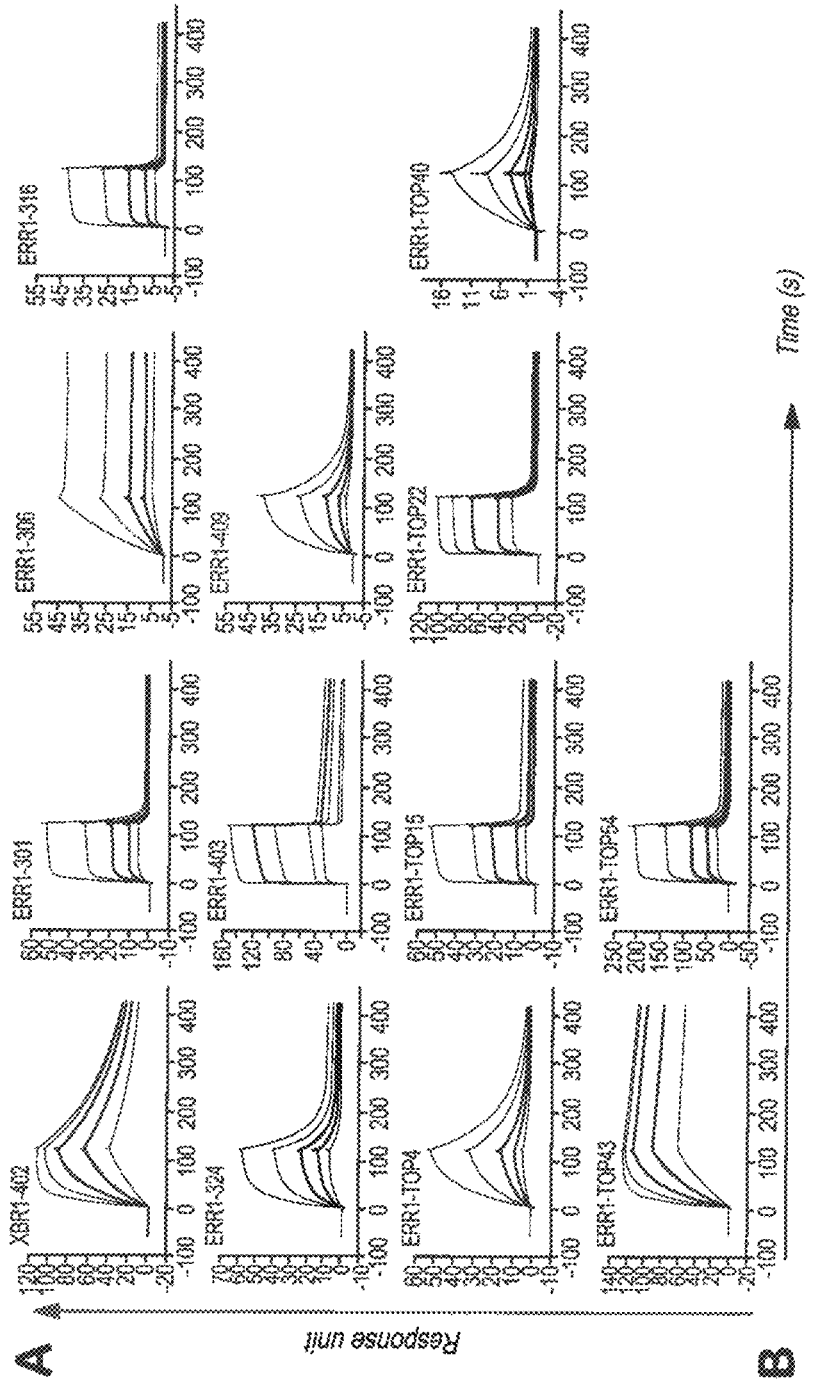
FIG. 6 shows affinity measurements of anti-hROR1 specific Fabs to hROR1 ECD by surface plasmon resonance (SPR). (A) Shown are Biacore ×100 sensorgrams obtained for the binding of each Fab to hFc-hROR1 captured by anti-human Fcγ antibody immobilized on CM5 chip after instantaneous background depletion. Fabs were injected at five different concentrations with the highest concentration indicated in table (B), one of the five concentrations was tested in duplicates. (B) Monovalent affinities of each Fab are shown in the table. The equilibrium dissociation constant ($K_d$) was calculated from $k_{off}/k_{on}$ ($k_{on}$, association rate constant; $k_{off}$, dissociation rate constant).
Figure 10:
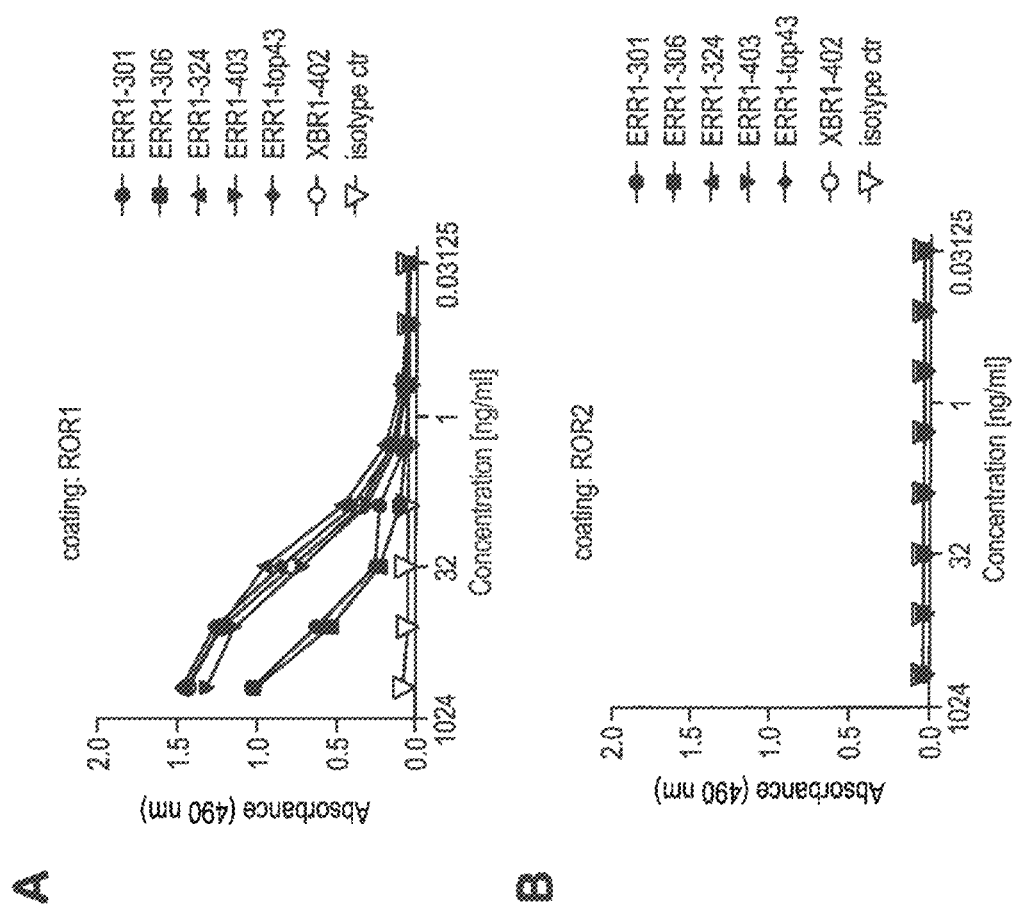
FIG. 10 shows the binding analyzed by ELISA of selected hROR1 specific rabbit-human-Fc chimeric antibodies of selected clones ERR1-301, XBR1-402, ERR1-306, ERR1-324, ERR1-403 and ERR1-Top43 to recombinant, purified hROR1 (panel A) and to recombinant, purified hROR2 as a negative control (panel B).

As a result of the chosen strategy, a number of novel rabbit high-affinity anti-human ROR1 antibodies have been identified with diverse CDR1, 2 and 3 clonotypes (FIG. 1) and with high binding selectivity for human ROR1, but not for its most related "sister molecule", human ROR2 (FIGS. 2, 3 and 10). Some of the hROR1-specific antibodies showed high affinity (single-digit nM affinities) for the hROR1 target (FIG. 6). As detailed herein, thirteen monoclonal antibodies (mAbs) in chimeric rabbit/human Fab format with different heavy and light chain sequences were obtained. These mAbs were tentatively named "XBR1-402", "ERR1-301", "ERR1-306", "ERR1-316", "ERR1-324", "ERR1-403", "ERR1-409", "ERR1-TOP4", "ERR1-TOP15", "ERR1-TOP22", "ERR1-TOP40", "ERR1-TOP43", and "ERR1-TOP54". All thirteen antibodies bind to purified human ROR1 as analyzed by ELISA and to cell surface human ROR1 as analyzed by flow cytometry. Neither binds to ROR2, which is the closest relative of ROR1 and shares 58% amino acid sequence identity with ROR1. Two mAbs ("ERR1-306" and "ERR1-TOP22") bind to both human and mouse ROR1 whereas the remaining eleven mAbs only bind to human ROR1.

Figure 8:
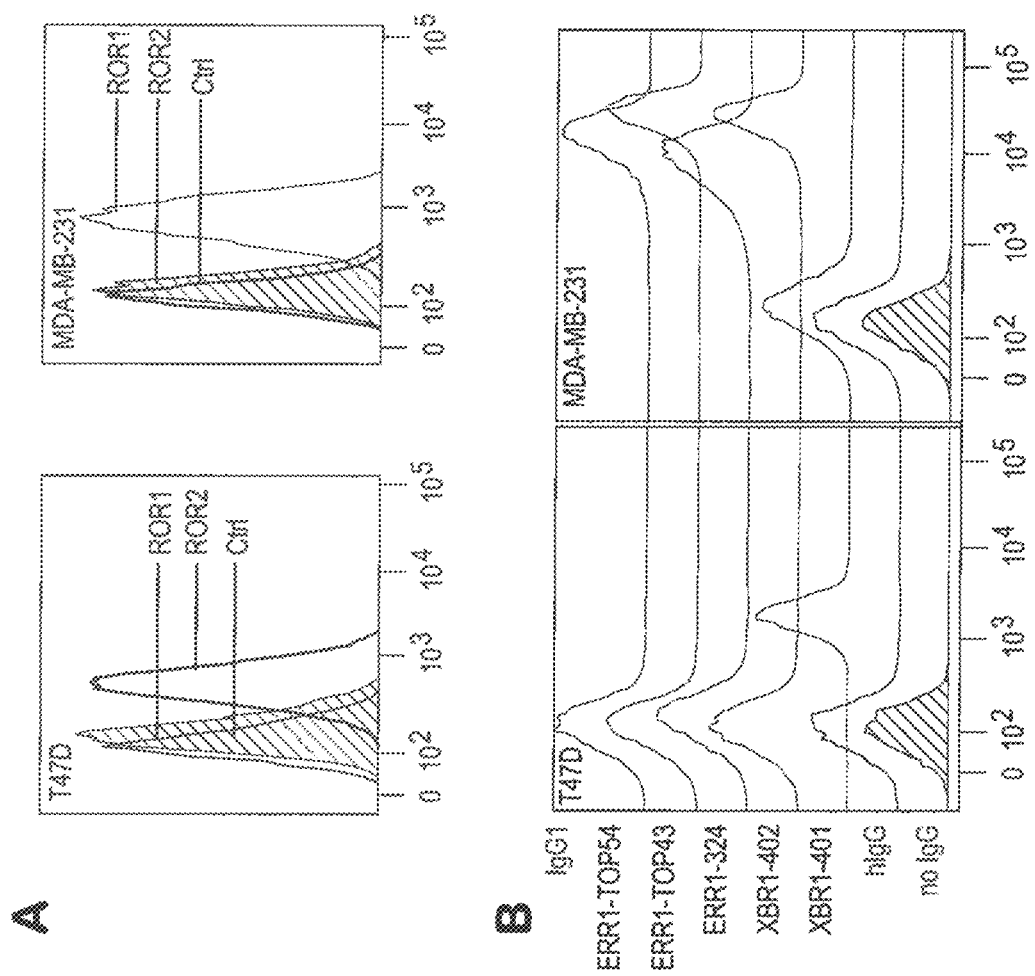
FIG. 8 shows the binding activity of selected chimeric rabbit/human IgG1 to endogenous hROR1 expressed on breast cancer cells measured by fluorescence activated cell sorting (FACS). Human breast cancer cell line MDA-MB-231 is known to express hROR1, human breast cancer cell line T47D is known to be negative for hROR1. In contrast, T47D is known to be ROR2 positive, whereas MDA-MB-231 is known to be negative for ROR-2 expression. ERR1-Top54, ERR1-Top43, ERR1-324, XBR1-402 were selected anti-hROR1 specific mAbs, XBR2-401 was a hROR2 specific mAb used as a specificity control (A) The expression of endogenous hROR1 and hROR2 on breast cancer cells was detected by flow cytometry using commercially available goat anti-human ROR1 and goat anti-human ROR2 polyclonal antibodies (R&D Systems), respectively, followed by Alexa Fluor 647-conjugated AffiniPure F(ab')2 donkey anti-goat IgG (H+L) polyclonal antibodies (Jackson ImmunoResearch Laboratories). Control stainings were done with the Alexa Fluor 647-conjugated AffiniPure F(ab')2 donkey anti-goat IgG (H+L) polyclonal antibodies alone. (B) The binding of chimeric rabbit/human IgG1 of selected clones ERR1-Top54, ERR1-Top43, ERR1-324, XBR1-402 (all hROR1 specific) and XBR2-401 (hROR2 specific) to ROR1 expressing human breast cancer cell line MDA-MB-231 and to ROR2 expressing human breast cancer cell line T47D was analyzed by flow cytometry using the chimeric rabbit/human IgG1 as primary antibodies and APC-labeled goat anti-human Fc-specific polyclonal antibodies as secondary antibody.

The affinity of all thirteen mAbs was determined by biolayer inferometry and surface plasmon resonance. In addition, several mAbs ("ERR-301", ("ERR-306", "ERR-403", "XBR1-402", "ERR1-324", "ERR1-TOP43", and "ERR1-TOP54") were converted to the chimeric rabbit/human IgG1 format, expressed in mammalian cells, and purified by Protein A affinity chromatography. Particularly, the highest affinity clones XBR1-402 and ERR1-TOP43 in further evaluation showed highest staining activities by FACS with human ROR1 overexpressing (FIG. 3) and naturally hROR1 expressing mammalian cells (FIG. 8). The two top-binding clones XBR1-402 and ERR1-TOP43 were also able to detect denatured ROR1 protein by Western-Blotting (FIG. 9), allowing the use of these clones for the development of a companion diagnostic for ROR1 expressing cancers.

In addition, several mAbs were expressed as chimeric rabbit/human IgG1 with C-terminal sortase-recognition tags, allowing site-specific conjugation of payloads to the antibody C-termini by sortase-enzyme mediated antibody conjugation technology (SMAC-Technology™) essentially as described in WO2014140317. These anti-hROR1 antibodies have then been site-specifically conjugated to a highly potent anthracycline-based PNU-159682 toxin derivative, $Gly_5$-EDA-PNU (FIG. 11B) in order to generate highly potent antibody drug conjugates (ADCs), essentially as disclosed in WO2016102679 (which is incorporated by reference herein and the text of which is included as an Appendix to this application). These ADCs have functionally been evaluated in various in vitro and in vivo tumor models against ADCs generated based on known anti-hROR1 antibodies. It was observed that one particular lead clone, called XBR1-402, displayed the highest potency and efficacy in comparison to various known antibodies (e.g. 2A2 (from WO 2010/124188), R11, R12 (both from WO 2012/075158), or ms961 (from WO 2014/031174), which forms the basis of humanized anti-hROR1 mAb cirmtuzumab, currently in clinical trials in CLL as a naked IgG1 mAb.

Based on the best-in-class properties in terms of functionality on tumor cell killing as an ADC, the lead clone XBR1-402 has then been humanized, which generated several humanized clones with further increased affinity against hROR1, called "huXBR1-402-3", "huXBR1-402-8", "huXBR1-402-15", "huXBR1-402-17", "huXBR1-402-19" and "huXBR1-402-26". These humanized versions of lead clone XBR1-402 have also been evaluated as site-specifically conjugated PNU-ADCs and each of which exhibited further improved tumor cell killing in in vitro hROR1 tumor models.

Figure 26:
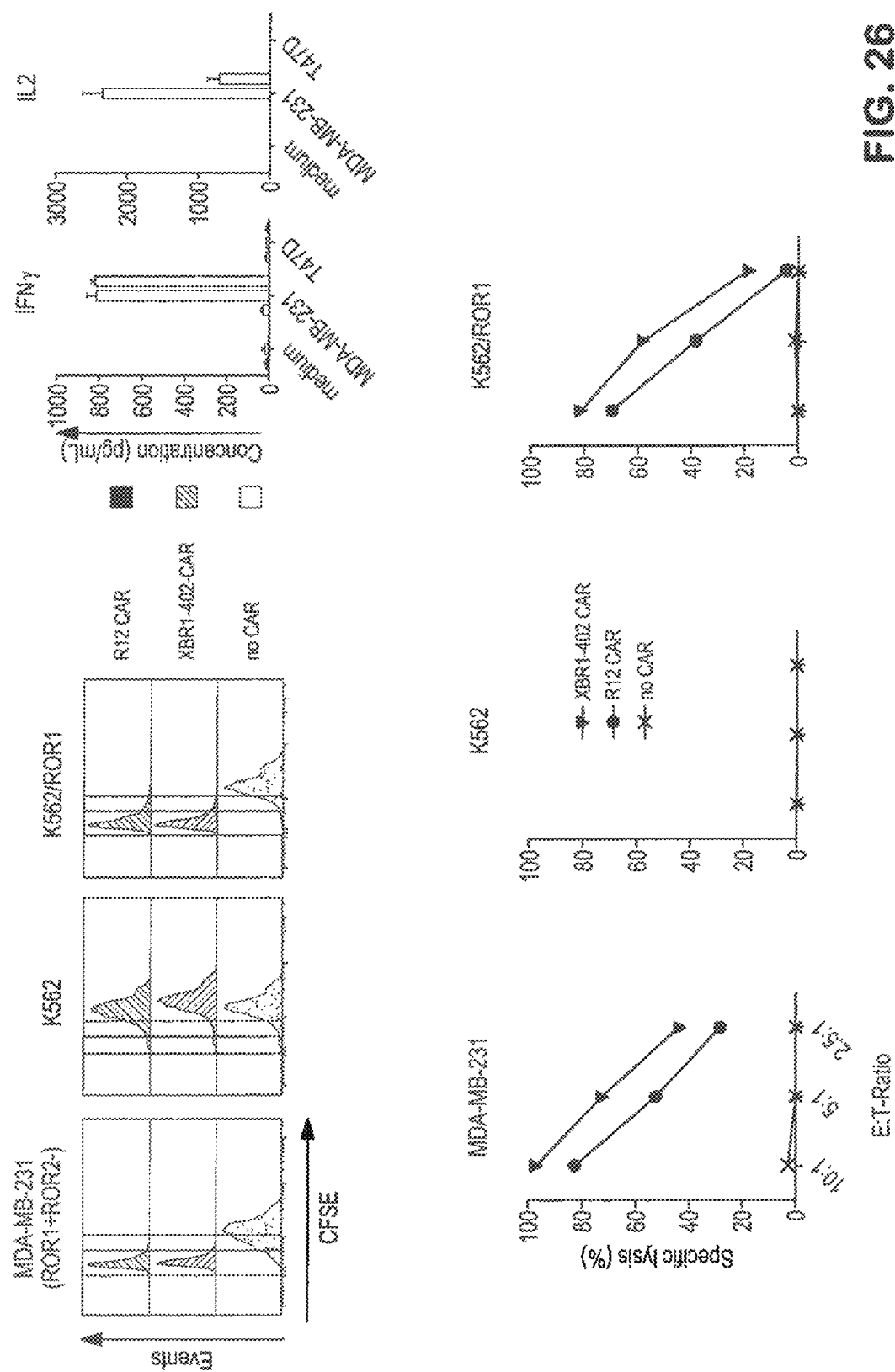
FIG. 26 shows a comparison of the in vitro activities of ROR1-targeting XBR1-402 CAR-T and R12 CAR-T.

To further investigate the therapeutic utility of the ROR1-targeting mAbs, CAR-T cells based on XBR1-402 were engineered using methods previously described for known ROR1-targeting mAbs R11 and R12 (Hudecek, M., Lupo-Stanghellini, M. T., Kosasih, P. L., Sommermeyer, D., Jensen, M. C., Rader, C., and Riddell, S. R. (2013) Receptor affinity and extracellular domain modifications affect tumor recognition by ROR1-specific chimeric antigen receptor T cells. Clin. Cancer Res. 19, 3153-3164). In brief, ex vivo expanded healthy donor CD8+CD62L+ T cells were lentivirally transduced with an EF1α promoter-driven expression cassette containing XBR1-402 in scFv format, followed by a short or long spacer, the transmembrane domain of human CD28, the signaling domain of 4-1BB, the signaling domain of CD3ζ, and a T2A-separated transmembrane EGFR fragment with truncated ligand binding and tyrosine kinase domains. FACS isolation of EGFR+ transduced T cells, revealed robust anti-ROR1 recognition in >90% of CAR-T cells. The activity of the ROR1-targeting XBR1-402 CAR-T with a short spacer was tested against breast cancer cell lines MDA-MB-231 (ROR1+ ROR2−) and T47D (ROR1− ROR2+). In the presence of ROR1+ ROR2− but not ROR1− ROR2+ target cells, XBR1-402 CAR-T rapidly proliferated, massively secreted IFN-γ and IL-2, and potently killed the target cells in vitro (FIG. 26). Notably, in direct comparison, the XBR1-402 CAR-T was found to be equally or more potent than the clinically investigated R12 CAR-T with the same short spacer and signaling domains.

Figure 27:
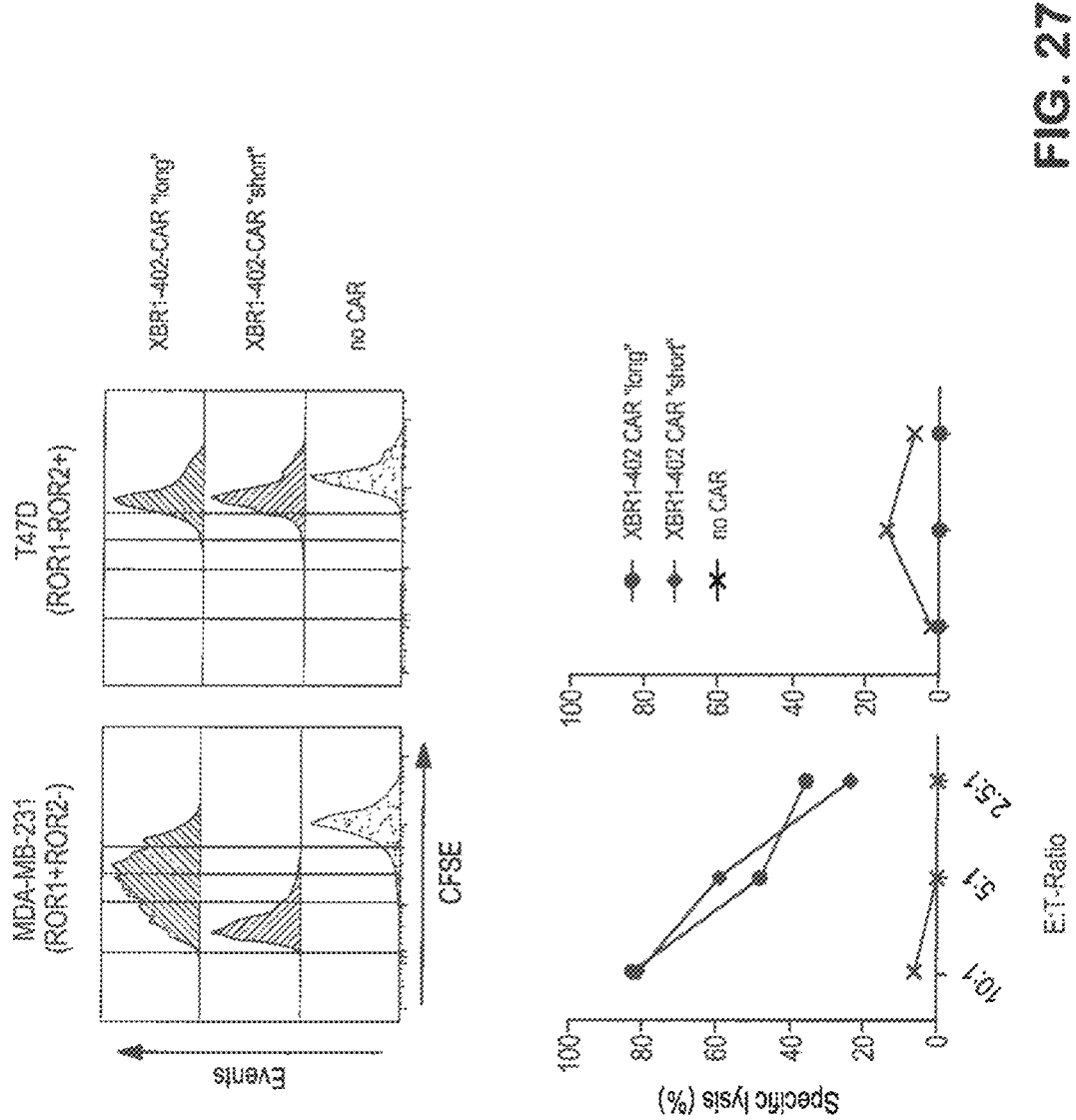
FIG. 27 shows a comparison of the in vitro activities of ROR1-targeting XBR1-402 CAR-T with short and long spacer.

Moreover, the inventors hypothesized that an optimal distance between T cell and target cell can be achieved by equipping CAR-T cells targeting membrane-distal epitopes with shorter spacers and vice versa. Based on this hypothesis, XBR1-402 CAR-T, which has an overlapping epitope with R12, is predicted to be more active when equipped with a short compared to a long spacer. Indeed, it was found that, in the presence of ROR1+ ROR2–target cells, XBR1-402 CAR-T with short linker proliferated more rapidly than XBR1-402 CAR-T with long spacer (FIG. 27) and also secreted significantly more IFN-γ and IL-2. In vitro cytotoxicity, however, was found to be equally potent (FIG. 27).

In accordance with these studies, the present invention provides novel monoclonal rabbit and humanized antibodies and related antibody-based binding proteins and antibody fragments thereof that specifically recognize ROR1, as well as antibody drug conjugates and CARs with specific anti-tumor activity in hROR1 expressing tumor models in vitro and in vivo. Also provided in the invention are methods of using these antibody agents in therapeutic and diagnostic applications for diseases and conditions associated with abnormal or elevated ROR1 expression, e.g., cancer.

Figure 13:
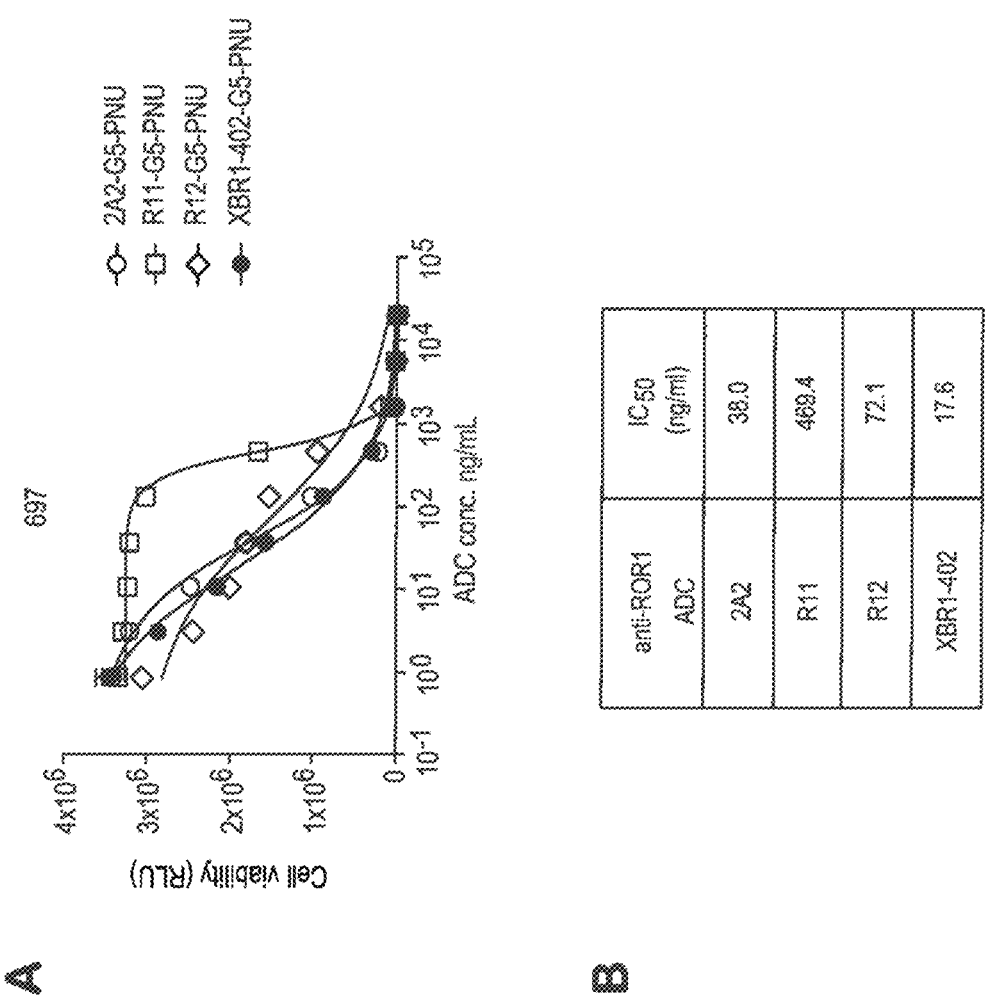
FIG. 13 shows in vitro potency for cell killing of ROR1 positive acute lymphocytic leukemia cell line 697 with four anti-ROR1-PNU ADCs, including ADCs based on antibody clones 2A2, R11 and R12, and based on anti-ROR1-antibody clone XBR1-402 disclosed herein. All antibodies were expressed as rabbit-human (R11, R12, XBR-402) or murine-human (2A2) chimeric $IgG_1$. (A) shows the cell killing over a concentration range of ADCs site-specifically conjugated to the toxin payload Gly5-EDA-PNU (abbreviated G5-PNU) with each of the ADCs. (B) shows the numeric $IC_{50}$ values for cell killing calculated from the curves in (A) for each of the anti-ROR1 ADCs.
Figure 14:
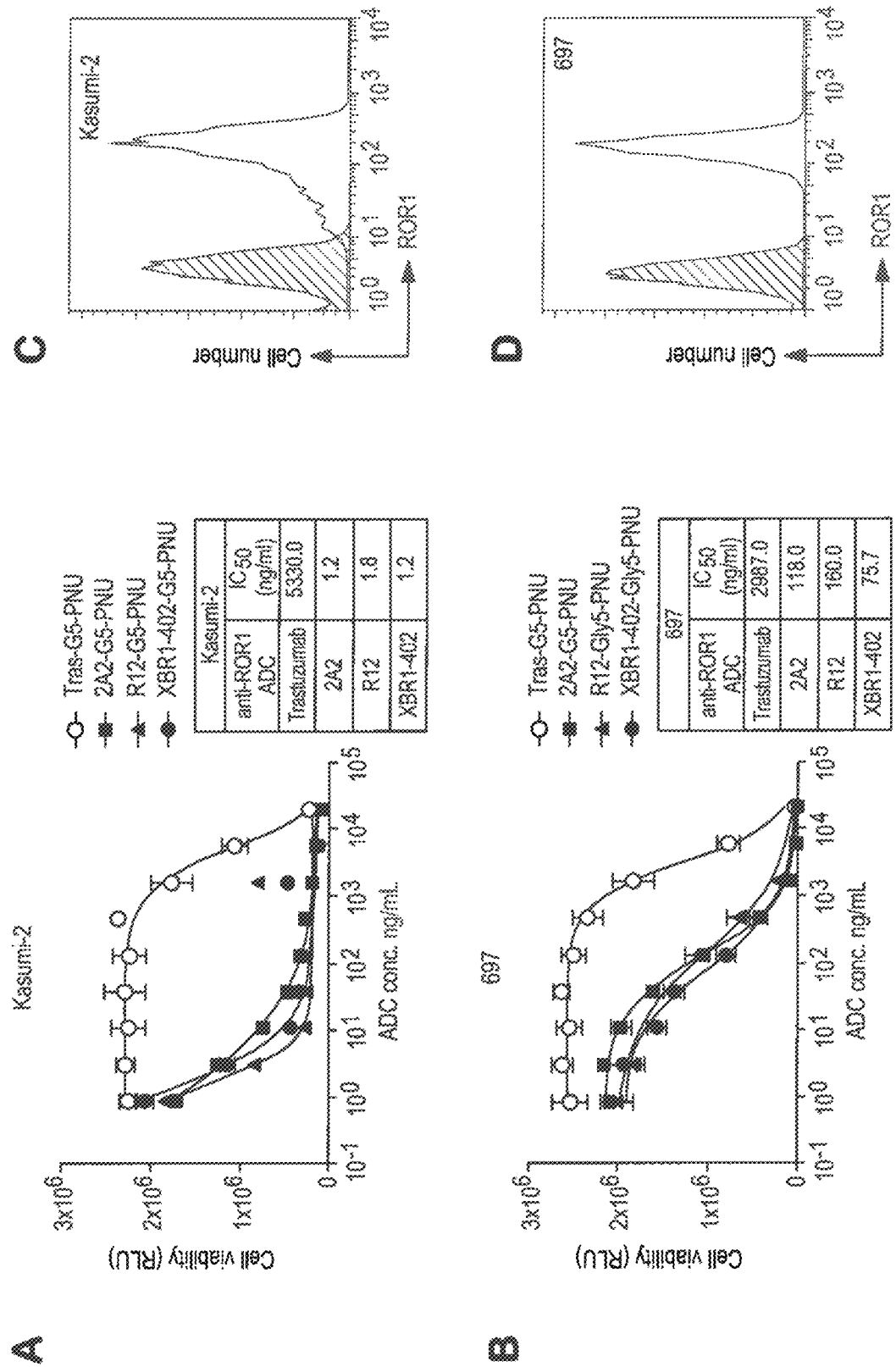
FIG. 14 shows in vitro cell killing of ROR1 positive ALL cell lines Kasumi-2 (A) and 697 (B) with selected anti-hROR1 ADCs site specifically conjugated to the Gly5-EDA-PNU toxin payload (abbreviated G5-PNU). The ADCs are based on anti-ROR1 antibody clone 2A2 and R12, and anti-ROR1 clone XBR1-402 as indicated. HER-2 specific trastuzumab, site-specifically conjugated to $Gly_5$-EDA-PNU toxin payload was used as an isotype matched control ADC. Panels C and D show the expression levels of ROR1 measured on the cell surface of Kasumi-2 and 697 as analyzed by FACS using antibody 2A2 as a primary antibody versus an isotype-matched control antibody.
Figure 15:
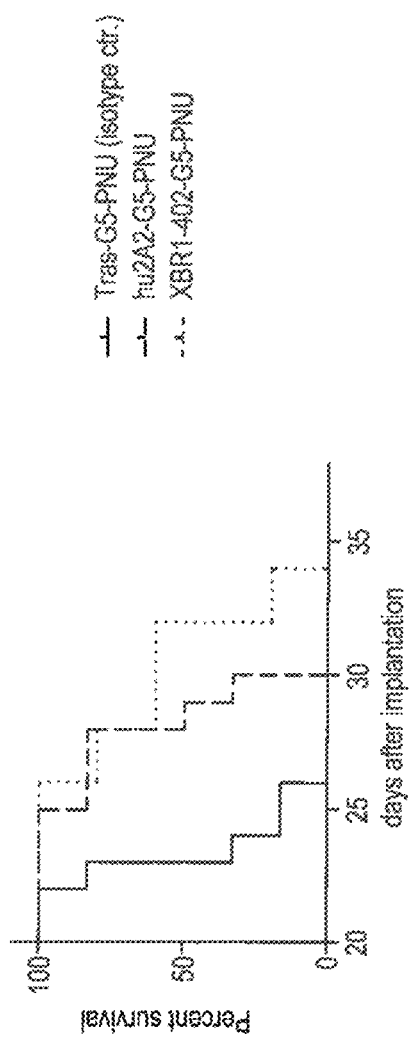
FIG. 15. (A) shows in vivo efficacy of ADCs in a disseminated mouse model of ROR1-positive 697 with EDA-$Gly_5$-PNU ADCs. Mice (groups of 8 animals) have been transplanted intravenously with $10^6$ 697 human ALL cells and treated 7 and 14 days later with each 1 mg/kg PNU-ADC based on antibody 2A2 and novel antibody XBR1-402, or as a negative control, with PNU-ADC based on HER2-specific antibody trastuzumab. Percent survival in the groups of mice was plotted over time. (B) shows the plasma concentration of the ADCs measured in the mice that received 1 mg/kg after 12 and 19 days measured by immuno-based ELISA assay using capturing with an anti-human Fcg reagent and detection with either an anti-kappa-light chain detection antibody for the antibody concentration and an anti-PNU detection antibody for the ADC concentration.
Figure 15:
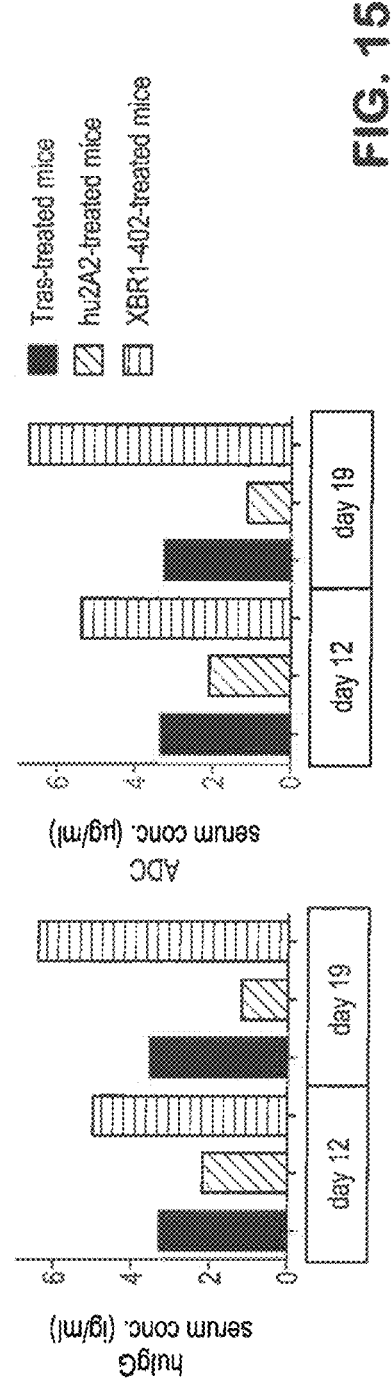

The antibodies and related compositions of the invention have demonstrated other surprisingly advantageous properties. Functional evaluation of the novel clones as site-specifically conjugated ADCs with a highly potent PNU-anthracycline payload, employing various in vitro and in vivo models, revealed that particularly novel clone XBR1-402 performed better than any of the known antibodies. For instance, R11-based ADCs had limited potency already in in vitro tumor models (FIG. 13). In comparison to antibody clones 99961 (ms961), 2A2 and R12, novel XBR1-402 described herein also consistently performed better in tumor models in vitro (FIGS. 13, 14, 17), which was even more evident in tumor models in vivo (FIGS. 15 & 18). Combined with the favorable properties of the XBR1-402 clone, in terms of its highly specific recognition of ROR1when tested against 4,336 human plasma membrane proteins (FIG. 29), and the favorable stability of the ADC in mouse plasma and other sera evaluated (FIGS. 15B, 19 & 20), XBR1-402-based ADCs appear to have the potential for best-in-class anti-ROR1 targeting products with high potential for ADC therapy.

Figure 22:
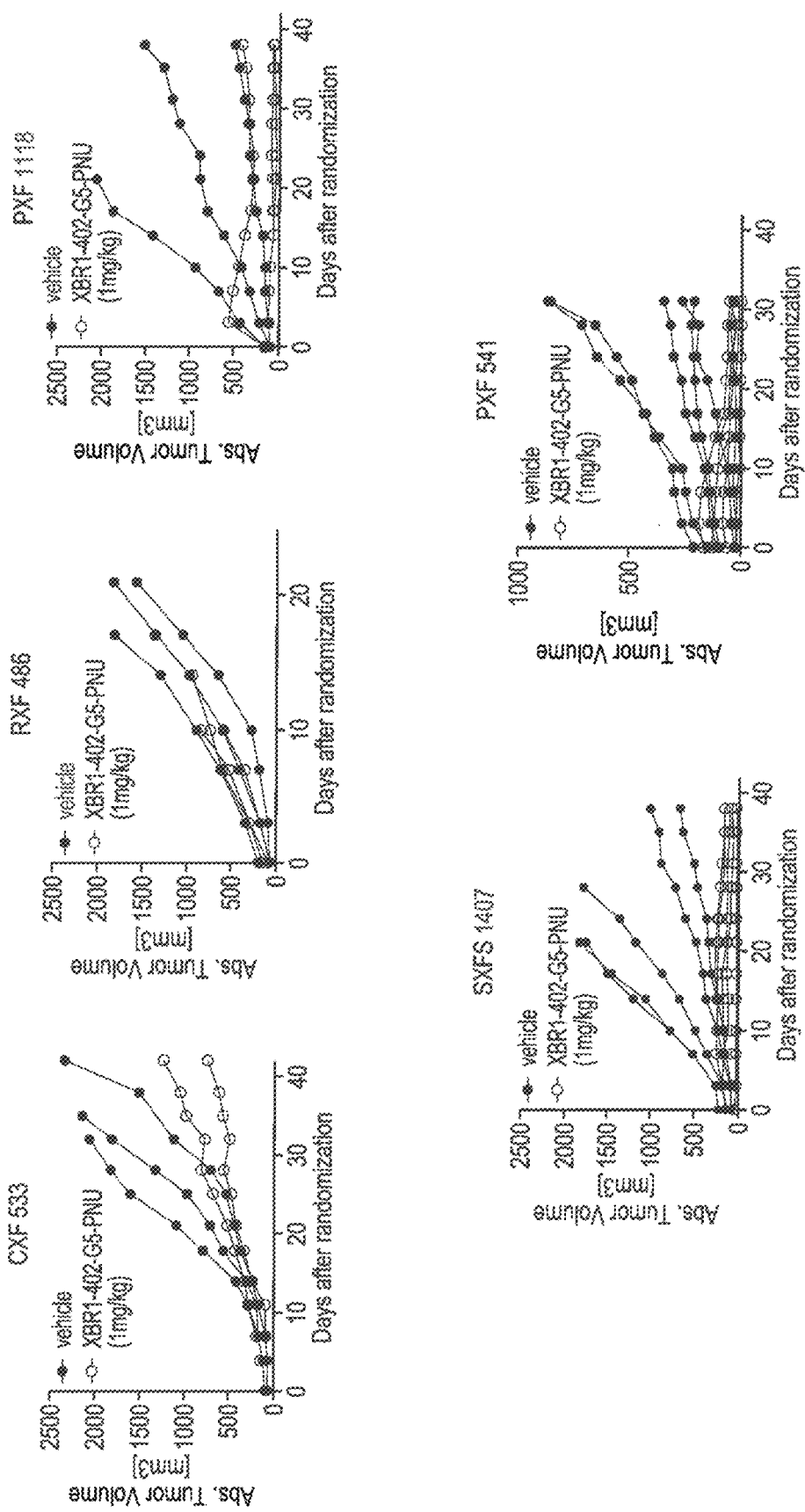
FIG. 22 shows the efficacy of the site-specifically conjugated PNU-ADC of XBR1-402 anti-ROR1 ADC in different patient derived tumor models (PDX models) established in female NMRI nude mice implanted with CXF533, RXF 486, PXF 1118, SXFS 1407 and PXF 541 patient-derived tumor material as compared to mice treated with vehicle control.
Figure 25:
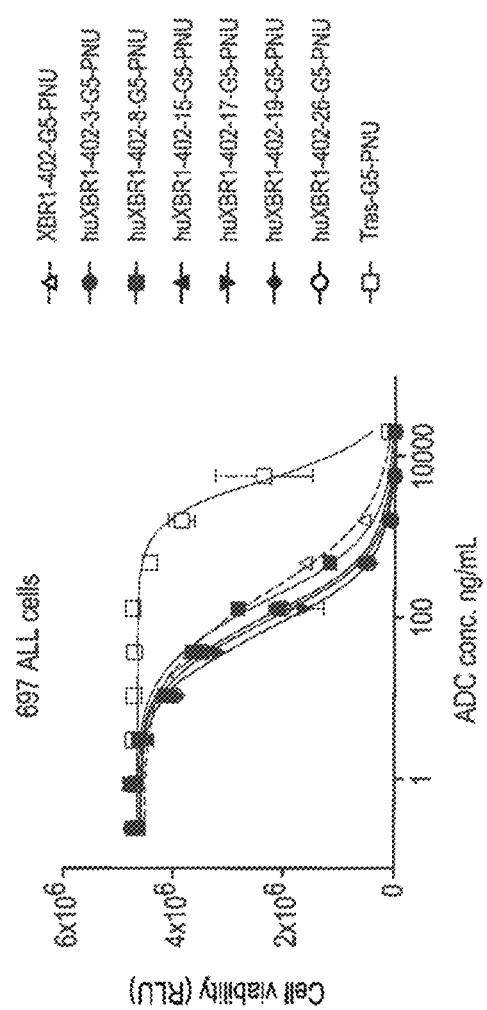
FIG. 25 shows (Panel A) the dose-response curves of in vitro cell killing assays performed on human 697 ALL cancer cells with hROR1-targeting parental XBR1-402-G5-PNU and with ADCs based on humanized antibodies: huXBR1-402-3-G5-PNU, huXBR1-402-8-G5-PNU, huXBR1-402-15-G5-PNU, huXBR1-402-17-G5-PNU, huXBR1-402-19-G5-PNU and huXBR1-402-26-G5-PNU. A PNU-ADC based on HER2-targeting antibody trastuzumab was used as an isotype control ADC (Tras-G5-PNU). Panel B shows the quantification of the in vitro cell killing efficacy ($IC_{50}$).

Furthermore, humanized versions of anti-ROR1 mAb XBR1-402 unexpectedly showed even higher affinity versus the parental rabbit clone XBR1-402 (FIG. 24) because affinities are often being reduced during the process of humanization of non-human antibodies (Margreitter et al. (2016) J. Mol. Recognit. 29: 266-275). The increased affinity also correlated with improved potency of these humanized mAbs when evaluated for anti-tumor activity as ADCs (FIG. 25). These data evidence the high potential of the evaluated anti-ROR1 ADC, based on humanized XBR1-402 antibodies for the therapy of human disease. This high potential for an effective tumor therapy of a PNU-ADC based on XBR1-402 and/or humanized XBR1-402 is supported by the high efficacy of the XBR1-402 based ADC in a variety of hROR1 expressing patient derived xenograft models (FIG. 22).

The highly functional anti-hROR1 antibodies and related compositions described herein have displayed exquisite functional properties for use as therapeutic agents in the therapy of human cancers associated with ROR1 expression. These include the various hROR1 antibodies, antibody fragments, antibody-based binding proteins, ADCs or CARs described herein, which have the same or essentially the same binding properties as demonstrated by the specific antibodies exemplified herein (e.g., XBR1-402). Thus, the favorable properties and high therapeutic potential demonstrated by the exemplified antibodies herein can be extended to homologous antibodies, antibody fragments, antibody-based binding proteins, ADCs, CARs that contain some or all of the CDR sequences of the variable heavy and/or light chains disclosed in the invention, or essentially similar CDR sequences of the variable heavy and/or light chains disclosed in the invention. The favorable properties and/or the high therapeutic potential can also be extended to antibodies, antibody fragments, antibody-based binding proteins, ADCs, CARs that only contain one of the two immunoglobulin chains of the disclosed antibodies (i.e., either heavy or light chain), or one of the two immunoglobulin chains (i.e. either heavy or light chain) that are homologous to the exemplified antibodies.

II. Definitions

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); and *A Dictionary of Biology* (*Oxford Paperback Reference*), Martin and Hine (Eds.), Oxford University Press (4$^{th}$ ed., 2000). In addition, the following definitions are provided to assist the reader in the practice of the invention.

The term "antibody" also synonymously called "immunoglobulins" (Ig), or "antigen-binding fragment" refers to polypeptide chain(s) which exhibit a strong monovalent, bivalent or polyvalent binding to a given antigen, epitope or epitopes. Unless otherwise noted, antibodies or antigen-binding fragments used in the invention can have sequences derived from any vertebrate species. They can be generated using any suitable technology, e.g., hybridoma technology, ribosome display, phage display, gene shuffling libraries, semi-synthetic or fully synthetic libraries or combinations thereof. Unless otherwise noted, the term "antibody" as used in the present invention includes intact antibodies, antigen-binding polypeptide fragments and other designer antibodies that are described below or well known in the art (see, e.g., Serafini, J Nucl. Med. 34:533-6, 1993).

An intact "antibody" typically comprises at least two heavy (H) chains (about 50-70 kD) and two light (L) chains (about 25 kD) inter-connected by disulfide bonds. The recognized immunoglobulin genes encoding antibody chains include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Each heavy chain of an antibody is comprised of a heavy chain variable region ($V_H$) and a heavy chain constant region. The heavy chain constant region of most IgG isotypes (subclasses) is comprised of three domains, $C_{H1}$, $C_{H2}$ and $C_{H3}$, some IgG isotypes, like IgM or IgE comprise a fourth constant region domain, $C_{H4}$. Each light chain is comprised of a light chain variable region ($V_L$) and a light chain constant region. The light chain constant region is comprised of one domain, $C_L$. The variable regions of the heavy and light chains contain a binding domain that interacts with an antigen. The constant regions of the antibodies may mediate the binding of the immunoglobulin to host tissues or factors, including various cells of the immune system and the first component (Clq) of the classical complement system.

The $V_H$ and $V_L$ regions of an antibody can be further subdivided into regions of hypervariability, also termed complementarity determining regions (CDRs), which are interspersed with the more conserved framework regions (FRs). Each $V_H$ and $V_L$ is composed of three CDRs and four FRs, arranged from amino-terminus to carboxyl-terminus in the following order: FR1, CDR1, FR2, CDR2, FR3, CDR3, FR4. The locations of CDR and FR regions and a numbering system have been defined by, e.g., Kabat et al., *Sequences of Proteins of Immunological Interest*, U.S. Department of Health and Human Services, U.S. Government Printing Office (1987 and 1991).

An "antibody-based binding protein", as used herein, may represent any protein that contains at least one antibody-derived $V_H$, $V_L$, or $C_H$ immunoglobulin domain in the context of other non-immunoglobulin, or non-antibody derived components. Such antibody-based proteins include, but are not limited to (i) Fe-fusion proteins of binding proteins, including receptors or receptor components with all or parts of the immunoglobulin $C_H$ domains, (ii) binding proteins, in which $V_H$ and or $V_L$ domains are coupled to alternative molecular scaffolds, or (iii) molecules, in which immunoglobulin $V_H$, and/or $V_L$, and/or $C_H$ domains are combined and/or assembled in a fashion not normally found in naturally occurring antibodies or antibody fragments.

"Binding affinity" is generally expressed in terms of equilibrium association or dissociation constants ($K_A$ or $K_D$, respectively), which are in turn reciprocal ratios of dissociation and association rate constants ($k_{off}$ and $k_{on}$, respectively). Thus, equivalent affinities may correspond to different rate constants, so long as the ratio of the rate constants remains the same. The binding affinity of an antibody is usually be expressed as the $K_D$ of a monovalent fragment (e.g. a Fab fragment) of the antibody, with $K_D$ values in the single-digit nanomolar range or below (subnanomolar or picomolar) being considered as very high and of therapeutic and diagnostic relevance.

As used herein, the term "binding specificity" refers to the selective affinity of one molecule for another such as the binding of antibodies to antigens (or an epitope or antigenic determinant thereof), receptors to ligands, and enzymes to substrates. Thus, all monoclonal antibodies that bind to a particular antigenic determinant of an entity (e.g., a specific epitope of ROR1 or ROR2) are deemed to have the same binding specificity for that entity.

The term "Antibody Drug Conjugate", or "ADC" refers to an antibody to which a therapeutically active substance or an active pharmaceutical ingredient (API) has been covalently coupled, such that the therapeutically active substance or an active pharmaceutical ingredient (API) can be targeted to the binding target of the antibody to exhibit its pharmacologic function. The therapeutically active substance or an active pharmaceutical ingredient can be a cellular toxin that is able to effect killing of the cells targeted by the ADCs, preferably malignant or cancer cells. The covalent attachment of a therapeutically active substance, an active pharmaceutical ingredient or a cellular toxin can be performed in a non-site specific manner using standard chemical linkers that couple payloads to lysine or cysteine residues, or, preferably the conjugation is performed in a site-specific manner, that allows full control of conjugation site and drug to antibody ratio (DAR) of the ADC to be generated.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" refer to a variant which has conservative amino acid substitutions, amino acid residues replaced with other amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

The term "contacting" has its normal meaning and refers to combining two or more agents (e.g., polypeptides or phage), combining agents and cells, or combining two populations of different cells. Contacting can occur in vitro, e.g., mixing an antibody and a cell or mixing a population of antibodies with a population of cells in a test tube or growth medium. Contacting can also occur in a cell or in situ, e.g., contacting two polypeptides in a cell by co-expression in the cell of recombinant polynucleotides encoding the two polypeptides, or in a cell lysate. Contacting can also occur in vivo inside a subject, e.g., by administering an agent to a subject for delivery the agent to a target cell.

A "humanized antibody" is an antibody or antibody fragment, antigen-binding fragment, or antibody-based binding protein comprising antibody $V_H$ or $V_L$ domains with a homology to human $V_H$ or $V_L$ antibody framework sequences having a T20 score of greater than 80, as defined by defined by Gao et al. (2013) BMC Biotechnol. 13, pp. 55.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length.

Methods of alignment of sequences for comparison are well known in the art. Optimal alignment of sequences for comparison can be conducted, e.g., by the local homology algorithm of Smith and Waterman, Adv. Appl. Math. 2:482c, 1970; by the homology alignment algorithm of Needleman and Wunsch, J. Mol. Biol. 48:443, 1970; by the search for similarity method of Pearson and Lipman, Proc. Nat'l. Acad. Sci. USA 85:2444, 1988; by computerized implementations of these algorithms (GAP, BESTFIT, FASTA, and TFASTA in the Wisconsin Genetics Software Package, Genetics Computer Group, Madison, Wis.); or by manual alignment and visual inspection (see, e.g., Brent et al., Current Protocols in Molecular Biology, John Wiley & Sons, Inc. (ringbou ed., 2003)). Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively.

The term "subject" refers to human and non-human animals (especially non-human mammals). The term "subject" is used herein, for example, in connection with therapeutic and diagnostic methods, to refer to human or animal subjects. Animal subjects include, but are not limited to, animal models, such as, mammalian models of conditions or disorders associated with elevated ROR1 expression such as CLL, ALL, mantle cell lymphoma, neuroblastoma, sarcoma, renal cell carcinoma, breast cancer, lung cancer, colon cancer, head and neck cancer, melanoma, and other cancers. Other specific examples of non-human subjects include, e.g., cows, horses, sheep, pigs, cats, dogs, mice, rats, rabbits, guinea pigs, monkeys.

Artificial T cell receptors (also known as chimeric T cell receptors, chimeric immunoreceptors, chimeric antigen receptors (CARs) or T-bodies) are engineered receptors, which graft an arbitrary specificity onto an immune effector cell. Typically, these receptors are used to graft the specificity of a monoclonal antibody onto a T cell; with transfer of their coding sequence facilitated by retroviral or lentiviral vectors or by transposons. CAR-engineered T cells (also abbreviated CAR-T cells) are genetically engineered T cells armed with chimeric receptors whose extracellular recognition unit is comprised of an antibody-derived recognition domain and whose intracellular region is derived from one or more lymphocyte stimulating moieties. The structure of the prototypic CAR is modular, designed to accommodate various functional domains and thereby to enable choice of specificity and controlled activation of T cells. The preferred antibody-derived recognition unit is a single chain variable fragment (scFv) that combines the specificity and binding residues of both the heavy and light chain variable regions of a monoclonal antibody. The most common lymphocyte activation moieties include a T-cell costimulatory (e.g. CD28) domain in tandem with a T-cell triggering (e.g. CD3zeta) moiety. By arming effector lymphocytes (such as T cells and natural killer cells) with such chimeric receptors, the engineered cell is re-directed with a pre-defined specificity to any desired target antigen, in a non-HLA restricted manner. CAR constructs are introduced ex vivo into T cells from peripheral lymphocytes of a given patient using retroviral or lentiviral vectors or transposons. Following infusion of the resulting CAR-engineered T cells back into the patient, they traffic, reach their target site, and upon interaction with their target cell or tissue, they undergo activation and perform their predefined effector function. Therapeutic targets for the CAR approach include cancer and HIV-infected cells, or autoimmune effector cells.

The terms "treat," "treating," "treatment," and "therapeutically effective" used herein do not necessarily imply 100% or complete treatment. Rather, there are varying degrees of treatment recognized by one of ordinary skill in the art as having a potential benefit or therapeutic effect. In this respect, the inventive method can provide any amount of any level of treatment. Furthermore, the treatment provided by the inventive method can include the treatment of one or more conditions or symptoms of the disease being treated.

A "vector" is a replicon, such as plasmid, phage or cosmid, to which another polynucleotide segment may be attached so as to bring about the replication of the attached segment. Vectors capable of directing the expression of genes encoding for one or more polypeptides are referred to as "expression vectors".

Figure 23:
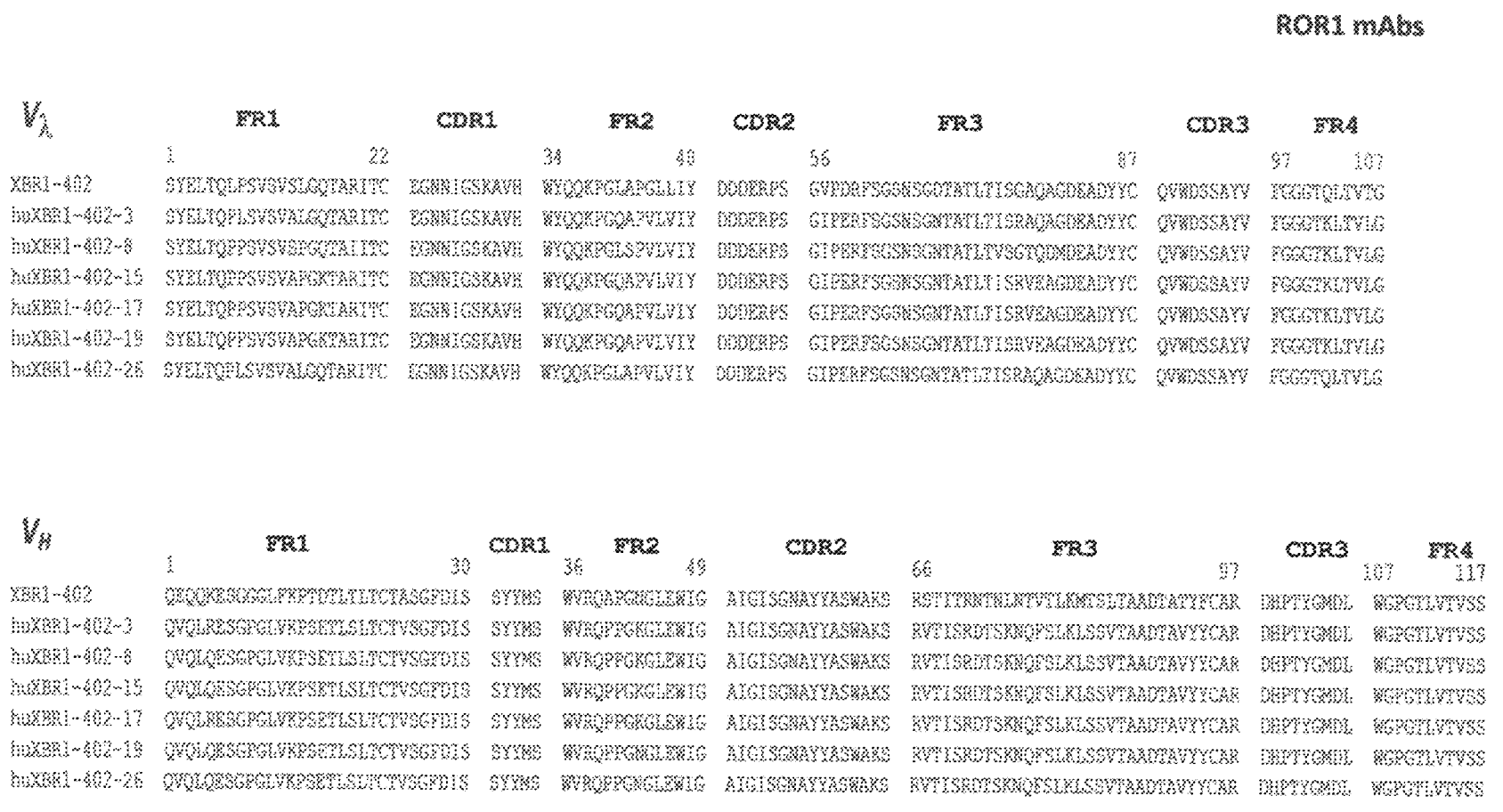

III. Antibodies, Antibody-Based Binding Proteins, Antibody Fragments Thereof, Antibody Drug Conjugates (ADCs), or CARs Specifically Binding to ROR1 and Related Derivative Compounds In one aspect, the invention provides novel antibodies, antibody-based binding proteins, antibody fragments thereof, ADCs or CARs that specifically bind to human ROR1 with the same binding specificity as that of anti-ROR1 antibody exemplified herein (FIGS. 1 and 23). Antibodies of the invention include intact antibodies (e.g., IgG1 antibodies exemplified herein), antibody fragments or antigen-binding fragments (e.g., Fab fragments exemplified herein), antibody-based binding proteins, ADCs and CARs which contain the antigen-binding portions of an intact antibody that retain capacity to bind the cognate antigen, ROR1. Examples of such antibody fragments include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an intact antibody; (v) disulfide stabilized Fvs (dsFvs) which have an interchain disulfide bond engineered between structurally conserved framework regions; (vi) a single domain antibody (dAb) which consists of a $V_H$ or $V_L$ domain (see, e.g., Ward et al., Nature 341:544-546, 1989); and (vii) an isolated complementarity determining region (CDR) as a linear or cyclic peptide. Examples of antibody-based binding proteins are polypeptides in which the binding domains of the antibodies are combined with other polypeptides or polypeptide domains, e.g. alternative molecular scaffolds, Fc-regions, other functional or binding domains of other polypeptides or antibodies resulting in molecules with addition binding properties, e.g. bi- or multispecific proteins or antibodies. Such polypeptides can create an arrangement of binding or functional domains normally not found in naturally occurring antibodies or antibody fragments.

Antibodies of the invention also encompass antibody fragments (or "antigen-binding fragments"), like single chain antibodies. The term "single chain antibody" refers to a polypeptide comprising a $V_H$ domain and a $V_L$ domain in polypeptide linkage, generally linked via a spacer peptide, and which may comprise additional domains or amino acid sequences at the amino- and/or carboxyl-termini. For example, a single-chain antibody may comprise a tether segment for linking to the encoding polynucleotide. As an example, a single chain variable region fragment (scFv) is a single-chain antibody. Compared to the $V_L$ and $V_H$ domains of the Fv fragment which are coded for by separate genes, a scFv has the two domains joined (e.g., via recombinant methods) by a synthetic linker. This enables them to be made as a single protein chain in which the $V_L$ and $V_H$ regions pair to form monovalent molecules.

Antibodies of the present invention also encompass single domain antigen-binding units, which have a camelid scaffold. Animals in the camelid family include camels, llamas, and alpacas. Camelids produce functional antibodies devoid of light chains. The heavy chain variable ($V_H$) domain folds autonomously and functions independently as an antigen-binding unit. Its binding surface involves only three CDRs as compared to the six CDRs in classical antigen-binding molecules (Fabs) or single chain variable fragments (scFvs). Camelid antibodies are capable of attaining binding affinities comparable to those of conventional antibodies.

The various antibodies, antibody-based binding proteins, and antibody fragments thereof described herein can be produced by enzymatic or chemical modification of the intact antibodies, or synthesized de novo using recombinant DNA methodologies, or identified using phage display libraries. Methods for generating these antibodies, antibody-based binding proteins, and antibody fragments thereof are all well known in the art. For example, single chain antibodies can be identified using phage display libraries or ribosome display libraries, gene shuffled libraries (see, e.g., McCafferty et al., Nature 348:552-554, 1990; and U.S. Pat. No. 4,946,778). In particular, scFv antibodies can be obtained using methods described in, e.g., Bird et al., Science 242:423-426, 1988; and Huston et al., Proc. Natl. Acad. Sci. USA 85:5879-5883, 1988. Fv antibody fragments can be generated as described in Skerra and Plückthun, Science 240:1038-41, 1988. Disulfide-stabilized Fv fragments (dsFvs) can be made using methods described in, e.g., Reiter et al., Int. J. Cancer 67:113-23, 1996. Similarly, single domain antibodies (dAbs) can be produced by a variety of methods described in, e.g., Ward et al., Nature 341:544-546, 1989; and Cai and Garen, Proc. Natl. Acad. Sci. USA 93:6280-85, 1996. Camelid single domain antibodies can be produced using methods well known in the art, e.g., Dumoulin et al., Nat. Struct. Biol. 11:500-515, 2002; Ghahroudi et al., FEBS Letters 414:521-526, 1997; and Bond et al., J. Mol. Biol. 332:643-55, 2003. Other types of antigen-binding fragments (e.g., Fab, F(ab)$_2$ or Fd fragments) can also be readily produced with routinely practiced immunology methods. See, e.g., Harlow & Lane, *Using Antibodies, A Laboratory Manual*, Cold Spring Harbor Laboratory Press, Cold Spring Harbor, N.Y., 1998.

Antibodies of the invention further include humanized antibodies with higher homology at amino acid level of the humanized antibody $V_H$ or $V_L$ domains to human antibody $V_H$ or $V_L$ domains than rodent $V_H$ or $V_L$ domains, preferably with a T20 score of greater than 80 as defined by Gao et al. (2013) BMC Biotechnol. 13, pp. 55.

In some embodiments, the antibodies, antibody fragments, antibody-based binding proteins, ADCs or CARs of the invention have heavy chain CDR1, CDR2 and CDR3 sequences and light chain CDR1, CDR2 and CDR3 sequences that are substantially identical to that of the antibodies shown in FIG. 1 or FIG. 23. The light chain and heavy chain CDR sequences of the exemplified antibodies are all indicated in the figure. In some of these embodiments, the antibodies, antibody fragments, antibody-based binding proteins, ADCs or CARs have (1) heavy chain CDR1-3 sequences that are substantially identical to SEQ ID NOs: 27-29, respectively; and light chain CDR1-3 sequences that are substantially identical to SEQ ID NOs:66-68, respectively; (2) heavy chain CDR1-3 sequences that are substantially identical to SEQ ID NOs:30-32, respectively; and light chain CDR1-3 sequences that are substantially identical to SEQ ID NOs:69-71, respectively; (3) heavy chain CDR1-3 sequences that are substantially identical to SEQ ID NOs: 33-35, respectively; and light chain CDR1-3 sequences that are substantially identical to SEQ ID NOs:72-74, respectively; (4) heavy chain CDR1-3 sequences that are substantially identical to SEQ ID NOs:36-38, respectively; and light chain CDR1-3 sequences that are substantially identical to SEQ ID NOs:75-77, respectively; (5) heavy chain CDR1-3 sequences that are substantially identical to SEQ ID NOs: 39-41, respectively; and light chain CDR1-3 sequences that are substantially identical to SEQ ID NOs:78-80, respectively; (6) heavy chain CDR1-3 sequences that are substantially identical to SEQ ID NOs:42-44, respectively; and light chain CDR1-3 sequences that are substantially identical to SEQ ID NOs:81-83, respectively; (7) heavy chain CDR1-3 sequences that are substantially identical to SEQ ID NOs: 45-47, respectively; and light chain CDR1-3 sequences that are substantially identical to SEQ ID NOs:84-86, respectively; (8) heavy chain CDR1-3 sequences that are substantially identical to SEQ ID NOs:48-50, respectively; and light chain CDR1-3 sequences that are substantially identical to SEQ ID NOs:87-89, respectively; (9) heavy chain CDR1-3 sequences that are substantially identical to SEQ ID NOs: 51-53, respectively; and light chain CDR1-3 sequences that are substantially identical to SEQ ID NOs:90-92, respectively; (10) heavy chain CDR1-3 sequences that are substantially identical to SEQ ID NOs:54-56, respectively; and light chain CDR1-3 sequences that are substantially identical to SEQ ID NOs:93-95, respectively; (11) heavy chain CDR1-3 sequences that are substantially identical to SEQ ID NOs:57-59, respectively; and light chain CDR1-3 sequences that are substantially identical to SEQ ID NOs:96-98, respectively; (12) heavy chain CDR1-3 sequences that are substantially identical to SEQ ID NOs:60-62, respectively; and light chain CDR1-3 sequences that are substantially identical to SEQ ID NOs:99-101, respectively; or (13) heavy chain CDR1-3 sequences that are substantially identical to SEQ ID NOs:63-65, respectively; and light chain CDR1-3 sequences that are substantially identical to SEQ ID NOs: 102-104, respectively.

In some embodiments the antibodies, antibody fragments, antibody-based binding proteins, ADCs or CARs of the invention comprise the heavy chain CDR1-CDR3 and light chain CDR1-CDR3 sequences are identical to the sequences shown in (1) SEQ ID NOs:27-29 and SEQ ID NOs:66-68 (antibody XBR1-402), (2) SEQ ID NOs:30-32 and SEQ ID NOs:69-71 (antibody ERR1-301), (3) SEQ ID NOs:33-35 and SEQ ID NOs:72-74 (antibody ERR1-306), (4) SEQ ID NOs:36-38 and SEQ ID NOs:75-77 (antibody ERR1-316), (5) SEQ ID NOs:39-41 and SEQ ID NOs:78-80 (antibody ERR1-324), (6) SEQ ID NOs:42-44 and SEQ ID NOs:81-83 (antibody ERR1-403), (7) SEQ ID NOs:45-47 and SEQ ID NOs:84-86 (antibody ERR1-409), (8) SEQ ID NOs:48-50 and SEQ ID NOs:87-89 (antibody ERR1-TOP4), (9) SEQ ID NOs:51-53 and SEQ ID NOs:90-92 (antibody ERR1-TOP15), (10) SEQ ID NOs:54-56 and SEQ ID NOs:93-95 (antibody ERR1-TOP22), (11) SEQ ID NOs:57-59 and SEQ ID NOs:96-98 (antibody ERR1-TOP40), (12) SEQ ID NOs: 60-62 and SEQ ID NOs:99-101 (antibody ERR1-TOP43), or (13) SEQ ID NOs:63-65 and SEQ ID NOs:102-104 (antibody ERR1-TOP54).

In other embodiments, the antibodies, antibody fragments, antibody-based binding proteins, ADCs or CARs of the invention that specifically bind to human ROR1 contain (a) a light chain variable domain having a sequence that is substantially identical to any one of SEQ ID NOs:14-26 or 136-141, (b) a heavy chain variable domain having a sequence that is substantially identical to any one of SEQ ID NOs:1-13 or 130-135, or (c) both a light chain of (a) and a heavy chain of (b). In some embodiments, the antibody comprises both a light chain of (a) and a heavy chain of (b). In some embodiments, the antibodies, antibody fragments, antibody-based binding proteins, ADCs or CARs of the invention contains (a) a light chain variable domain having at least 90% identity to any one of SEQ ID NOs:14-26 or 136-141, (b) a heavy chain variable domain having at least 90% sequence identity to any one of SEQ ID NOs:1-13 or 130-135, or (c) both a light chain of (a) and a heavy chain of (b). In some embodiments, the percentage identity can be at least 91%, at least 92%, at least 93%, at least 94%, at least 95%, at least 96%, at least 97%, at least 98%, or at least 99%, or even 100%. In some embodiments, the light chain variable domain has at least 95% identity to any one of SEQ ID NOs:14-26 or 136-141. In some embodiments, the light chain variable domain has 100% identity to any one of SEQ ID NOs:14-26 or 136-141. In some embodiments, the antibody, antibody fragments, antibody-based binding proteins, ADCs or CARs contains a heavy chain variable domain having at least 90% identity to any one of SEQ ID NOs:1-13 or 130-135. In other embodiments, the percentage identity can be at least 91%, at least 92%, at least 93%, at least 94%, at least 95%, at least 96%, at least 97%, at least 98%, or at least 99%, or even 100%. In some embodiments, the heavy chain variable domain has at least 95% identity to any one of SEQ ID NOs:1-13 or 130-135. In some embodiments, the heavy chain variable domain has 100% identity to any one of SEQ ID NOs:1-13 or 130-135.

In some embodiments, the antibodies, antibody fragments, antibody-based binding proteins, ADCs or CARs of the invention can comprise any heavy chain as described herein (e.g., heavy chains shown in FIGS. 1 and 23) in combination with any suitable light chain, such as those exemplified herein. Likewise, the antibody can comprise any of the light chains as described above (e.g., light chains shown in FIGS. 1 and 23) in combination with any suitable heavy chain, such as those exemplified herein. For example, in preferred embodiments, the antibody comprises a light chain having at least 90% identity to SEQ ID NO:14 and a heavy chain having at least 90% identity to SEQ ID NO:1 (antibody XBR1-402), a light chain having at least 90% identity to SEQ ID NO:18 and a heavy chain having at least 90% identity to SEQ ID NO:5 (antibody ERR1-324), a light chain having at least 90% identity to SEQ ID NO:25 and a heavy chain having at least 90% identity to SEQ ID NO:12 (antibody ERR1-TOP43), or a light chain having at least 90% identity to SEQ ID NO:26 and a heavy chain having at least 90% identity to SEQ ID NO:13 (antibody ERR1-TOP54). In some embodiments, the antibody can comprise the light chain and heavy chain sequences respectively shown in (1) SEQ ID NO:14 and SEQ ID NO:1, (2) SEQ ID NO:18 and SEQ ID NO:5, (3) SEQ ID NO:25 and SEQ ID NO:12, or (4) SEQ ID NO:26 and SEQ ID NO:13. In the various embodiments, percent (%) identity of peptide sequences can be calculated, for example, as 100×[(identical positions)/min(TGA, TGB)], where TGA and TGB are the sum of the number of residues and internal gap positions in peptide sequences A and B in the alignment that minimizes TGA and TGB. See, e.g., Russell et al, J. Mol. Biol., 244: 332-350 (1994).

The antibody of the invention can be any antibody including a full length antibody, an antibody fragment, an antibody-based binding protein that specifically recognizes or binds to the extracellular domain of human ROR1. For example, the antibody, antibody fragment or antibody-based binding protein can be polyclonal, monoclonal, recombinant, chimeric, or humanized. Furthermore, the antibody can be of any isotype including without limitation IgA, IgD, IgE, IgG, or IgM. Thus, for example, the antibody can be any IgA such as IgA1 or IgA2, or any IgG such as IgG1, IgG2, IgG3, IgG4, or synthetic IgG. The antibody can also be any antibody fragment or antibody-based binding protein having specificity for the extracellular domain of human ROR1, such as F(ab)2, Fv, scFv, IgGACH2, F(ab')2, scFv2CH3, Fab, VL, VH, scFv4, scFv3, scFv2, dsFv, Fv, scFv-Fc, (scFv)2, a diabody, a bivalent, a bispecific, or a multispecific antibody. The antibody can be any modified or synthetic antibody, including, but not limited to, non-depleting IgG antibodies, CARs, or other Fc or Fab variants of antibodies.

In addition to a heavy chain as described above, the antibody, antibody-based binding proteins or antibody fragments thereof of the invention can further comprise a light chain selected from a Fab library using sequential naive chain shuffling. Likewise, in addition to a light chain as described above, the antibody of the invention can further comprise a heavy chain selected from a Fab library using sequential naive chain shuffling. In some embodiments, the invention provides antibodies, antibody-based binding proteins or antibody fragments thereof that are conservatively modified variants of the anti-ROR1 antibodies exemplified herein. Typically, the variable regions of these variants have an amino acid sequence that is identical to one of these exemplified sequences except for conservative substitutions at one or more amino acid residues. In some embodiments, the antibody, antibody fragments, antibody-based binding proteins, ADCs or CARs of the invention specifically binds to human ROR1 and contains at least one CDR having a sequence selected from the group consisting of SEQ ID NOs:27-104. The invention also provides an isolated antibody with specificity for ROR1 containing one or more variants of the foregoing CDR sequences or substantially identically CDR sequences. The variant CDR sequences in these antibodies can include 1, 2, or 3 substitutions, insertions, deletions, or combinations thereof in a sequence selected from the group consisting of SEQ ID NOs:27-104. For example, a recombinant chimeric or humanized antibody (or fragment thereof) can include one, two, three, four, five, or six of the foregoing CDR sequences. In some embodiments, however, the recombinant chimeric or humanized antibody (or fragment thereof) includes three CDR sequences of the same light or heavy chain, e.g., light chain CDRS shown in SEQ ID NOs:66-68, SEQ ID NOs: 78-80, SEQ ID NOs:99-101, or SEQ ID NOs:102-104; and heavy chain CDRs shown in SEQ ID NOs:27-29, SEQ ID NOs:39-41, SEQ ID NOs:60-62, or SEQ ID NOs:63-65. In some embodiments, the recombinant chimeric or humanized antibody (or fragment thereof) includes six CDR sequences of the same antibody, e.g., (a) SEQ ID NOs:66-68 and SEQ ID NOs:27-29 (antibody XBR1-402); (b) SEQ ID NOs:78-80 and SEQ ID NOs:39-41(antibody ERR1-324); (c) SEQ ID NOs:99-101 and SEQ ID NOs:60-62 (antibody ERR1-TOP43), or (d) SEQ ID NOs:102-104 and SEQ ID NOs: 63-65 (antibody ERR1-TOP54).

In some embodiments, the invention provides antibodies, antibody-based binding proteins or antibody fragments thereof with avidity for ROR1 of about 10 μM or less, 5 μM or less, 2 μM or less, 1 μM or less, 500 nM or less, 400 nM or less, 300 nM or less, or 200 nM or less. In some embodiments, the antibodies, antibody fragments, antibody-based binding proteins, ADCs or CARs bind to ROR1 with an avidity of about 100 nM or less, about 75 nM or less, about 50 nM or less, about 25 nM or less, about 10 nM or less, or about 5 nM or less. In some embodiments, the antibodies, antibody fragments, antibody-based binding proteins, ADCs or CARs bind to ROR1 with an avidity of about 1 nM or less, about 800 pM or less, about 700 pM or less, about 600 pM or less, about 500 pM or less, about 400 pM or less, about 300 pM or less, about 200 pM or less, or about 100 pM or less. Avidity can be measured using art-known techniques, such as ELISA, biolayer inferometry, or surface plasmon resonance.

The antibody, antibody-based binding protein or antibody fragment thereof of the invention can be produced by any suitable technique, for example, using any suitable eukaryotic or non-eukaryotic expression system. In certain embodiments, the antibody is produced using a mammalian expression system. Some specific techniques for generating the antibodies antibody-based binding proteins or antibody fragments thereof of the invention are exemplified herein. In some embodiments, the antibodies, antibody-based binding proteins or antibody fragments thereof of the invention can be produced using a suitable non-eukaryotic expression system such as a bacterial expression system. Bacterial expression systems can be used to produce fragments such as a F(ab)2, Fv, scFv, IgGACH2, F(ab')2, scFv2CH3, Fab, VL, VH, scFv4, scFv3, scFv2, dsFv, Fv, scFv-Fc, (scFv)2, and diabodies. Techniques for altering DNA coding sequences to produce such fragments are known in the art.

The antibodies, antibody-based binding proteins or antibody fragments thereof of the invention can be conjugated to a synthetic molecule using any type of suitable conjugation. Recombinant engineering and incorporated selenocysteine (e.g., as described in U.S. Pat. No. 8,916,159 issued on Dec. 23, 2014) can be used to conjugate a synthetic molecule. Other methods of conjugation can include covalent coupling to native or engineered lysine side-chain amines or cysteine side-chain thiols. See, e.g., Wu et al., Nat. Biotechnol, 23: 1 137-1 146 (2005).

In a preferred embodiment, the antibodies, antibody-based binding proteins or antibody fragments thereof of the invention conjugated to a synthetic molecule (called "ADC" for antibody drug conjugate with the synthetic molecule being a toxin) are obtained by means of site-specific sortase-enzyme mediated antibody conjugation. As disclosed in WO2014140317, sortases (also called sortase transpeptidases) form a group of prokaryotic enzymes that modify surface proteins by recognizing and cleaving a specific peptide motif called "sortase recognition tag" or "sortase tag". Usually, a given sortase enzyme recognizes one or more sortase recognition tags. Sortase enzymes can be naturally occurring, or may have undergone genetic engineering (Dorr et al., PNAS 2014; 111, 13343-8).

In a preferred embodiment, the conjugate is obtained by means of site-specific sortase-enzyme mediated conjugation of (a) an antibody, antibody-based binding protein or antibody fragment thereof as described herein carrying one or more sortase recognition tags, and (b) one or more synthetic molecules carrying a glycine or oligoglycine tag, Gly(n).

Preferably, the sortase recognition tag is fused or conjugated to the C-terminus of at least one subdomain of the antibody. Said sortase recognition tag is preferably selected from the group consisting of LPXSG (SEQ ID NO:142), LPXAG (SEQ ID NO:143), LPXTG (SEQ ID NO:144), LAXTG (SEQ ID NO:145), and NPQTG (SEQ ID NO:146).

Preferably, the oligoglycine tag, $Gly_{(n)}$, has a length of 1 to 21 glycine residues with n being any number from 1 to 21), preferably with a length of 3 to 5 amino acids (n from 3 to 5, i.e. $Gly_{(3)}$, $Gly_{(4)}$, or $Gly_{(5)}$).

The synthetic molecule can be any molecule such as one targeting a tumor. In some embodiments, the synthetic molecule for conjugation to the antibody is a protein (e.g., an antibody) or an RNA or DNA aptamer.

In one embodiment, the antibodies, antibody-based binding proteins or antibody fragments thereof of the invention conjugated to a synthetic molecule have the general formula $A-(L-P)_n$, in which: A is an antibody, antibody-based binding protein or antibody fragment thereof as described herein, L is one or more linkers, P is one or more payloads selected from the group consisting of a label and a cytotoxic or cytostatic agent, and in which n is an integer between ≥1 and ≤10.

In this embodiment, the linker preferably comprises, or consists of, at least one selected from the group consisting of: an oligopeptide linker (including cleavable and non-cleavable oligopeptide linkers), a hydrazine linker, a thiourea linker, a self-immolative linker, a succinimidyl trans-4-(maleimidylmethyl)cyclohexane-1-carboxylate (SMCC) linker, a maleimide linker, a disulfide linker, a thioether linker, and/or a maleimide linker.

The skilled person understands that further linkers may be suitable. Such linkers may be non-cleavable or may be cleaved by changes in pH, redox potential or specific intracellular enzymes. Cleavable oligopeptide linkers include protease- or matrix metalloprotease-cleavable linkers. It is understood that the linker may comprise combinations of the above. For example, the linker may be a valine-citruline PAB linker.

In a preferred embodiment, the linker comprises an oligopeptide with a sequence that contains the penta-peptide motif LPXSG (SEQ ID NO:142), LPXAG (SEQ ID NO:143), LPXTG (SEQ ID NO:144), LAXTG (SEQ ID NO:145), or NPQTG (SEQ ID NO:146) with X being any amino acid, followed by an oligo-glycine stretch, $Gly_{(n)}$, with n being an integer between ≥1 and ≤21. In a preferred embodiment, the linker is conjugated to the C-terminus of at least one subdomain of the antibody, antibody-based binding proteins or antibody fragments thereof.

In various embodiments, suitable synthetic molecules ("payloads") for conjugation to the antibody include, e.g., therapeutic agents such as cytotoxic, cytostatic, or antiangiogenic agents, radioisotopes, and liposomes. A cytotoxic agent can be a plant, fungal, or bacterial molecule. In some embodiments, the cytotoxic agent for conjugation to the antibody of the invention is a small molecular weight toxin (MW<2'000 Dalton, preferably MW<1'000 Dalton), a peptide toxin, or a protein toxin. Many specific examples of these toxins are well known in the art. See, e.g., Dyba et al., Curr. Pharm. Des. 10:2311-34, 2004; Kuyucak et al., Future Med. Chem. 6:1645-58, 2014; Beraud et al., Inflamm. Allergy Drug Targets. 10:322-42, 2011; and Middlebrook et al., Microbiol. Rev. 48:199-221, 1984. In some embodiments, a therapeutic agent is conjugated to the antibody. For example, the therapeutic agent can be a maytansinoid (e.g., maytansinol or DM1 maytansinoid), a taxane, a calicheamicin, a cemadotin, a monomethylauristatin (e.g., monomethylauristatin E or monomethylauristatin F), a pyrrolobenzodiazepine (PBD) or, preferably an anthracycline, more preferably a derivative of the highly potent anthracycline PNU-159682. Particularly preferred derivatives of the highly potent anthracycline PNU-159682 are disclosed in WO2016102679 (which is incorporated by reference herein). Therapeutic agents also include vincristine and prednisone. In various embodiments, the therapeutic agent that may be employed in the invention can be an antimetabolite (e.g., an antifolate such as methotrexate, a fluoropyrimidine such as 5-fluorouracil, cytosine arabinoside, or an analogue of purine or adenosine); an intercalating agent (for example, an anthracycline such as doxorubicin, nemorubicine, or preferably a derivative of PNU-159682), daunomycin, epirabicin, idarubicin, mitomycin-C, dactinomycin, or mithramycin, or other intercalating agents such as pyrrolobenzodiazepine; a DNA-reactive agent such as calicheamicins, tiancimycins, and other enediynes; a platinum derivative (e.g., cisplatin or carboplatin); an alkylating agent (e.g., nitrogen mustard, melphalan, chlorambucil, busulphan, cyclophosphamide, ifosfamide nitrosoureas or thiotepa); an RNA polymerase inhibitor such as α-amanitin; an antimitotic agent (e.g., a *vinca* alkaloid such as vincristine, or a taxoid such as paclitaxel or docetaxel); a topoisomerase inhibitor (for example, etoposide, teniposide, amsacrine, topotecan); a cell cycle inhibitor (for example, a flavopyridol); or a microbtubule agent (e.g., an epothilone, a tubulysine, a pre-tubulysine, discodermolide analog, or eleutherobin analog). A therapeutic agent can be a proteasome inhibitor or a topoisomerase inhibitor such as bortezomib, amsacrine, etoposide, etoposide phosphate, teniposide, or doxorubicin. Therapeutic radioisotopes include iodine ($^{134}$I), yttrium ($^{90}$Y) lutetium ($^{177}$Lu), actinium ($^{225}$Ac), praseodymium, astatine (At), rhenium (Re), bismuth (Bi or Bi), and rhodium (Rh). Antiangiogenic agents include linomide, bevacuzimab, angiostatin, and razoxane.

In a preferred embodiment, the synthetic toxin molecule is selected from PNU-159682 as described in Quintieri et al. (2005) and derivatives thereof (see formula (i) below), maytansine, monomethyl auristatin MMAE, and monomethyl auristatin MMAF. In a preferred embodiment, the toxin, joined to the linker at its wavy line, is of formula (i), as described in WO 2016102679 (which is incorporated by reference herein):

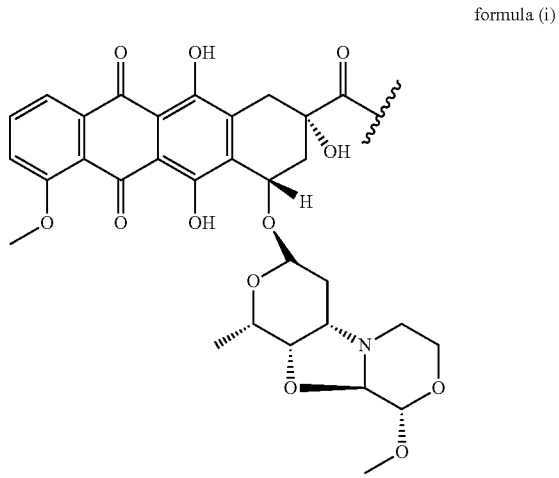

formula (i)

Figure 11:
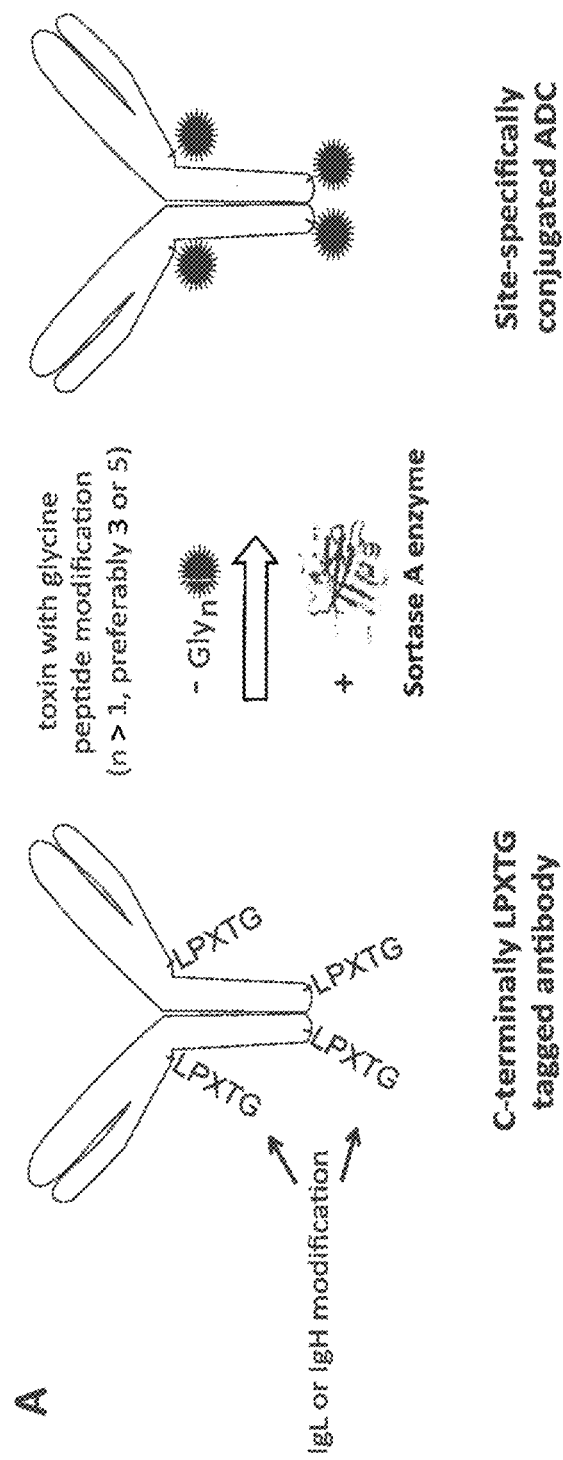
FIG. 11 shows schematically how site-specifically conjugated ADCs disclosed in this invention have been generated. (A) schematically shows the mechanism of sortase-enzyme mediated antibody conjugation (SMAC-technology) as disclosed in WO2014140317. In order to generate site-specifically conjugated ADCs, recombinant antibodies need to be expressed with the C-terminal pentapeptide motif LPXTG (SEQ ID NO:144), which serve as recognition sites for the sortase enzyme A from *Staphylococcus aureus* (SrtA). When a glycine modified toxin substrate is incubated with pentapeptide motif LPXTG containing antibody and sortase A enzyme, the sortase A enzyme catalyzes a transpeptidation reaction by which the glycine-modified toxin replaces the C-terminal glycine of the LPXTG motif and is covalently coupled to the threonine of the remaining LPXT (SEQ ID NO:147) sequence. This way C-terminally toxin-conjugated ADCs can be generated with high efficiency. (B) shows the structure of the preferred toxin, a PNU-159682 derivative comprising an ethylene-diamino (EDA) linker connecting a 5× glycine stretch to the carbonyl group at C13 of the anthracycline structure, as disclosed in WO2016102697.
Figure 11:
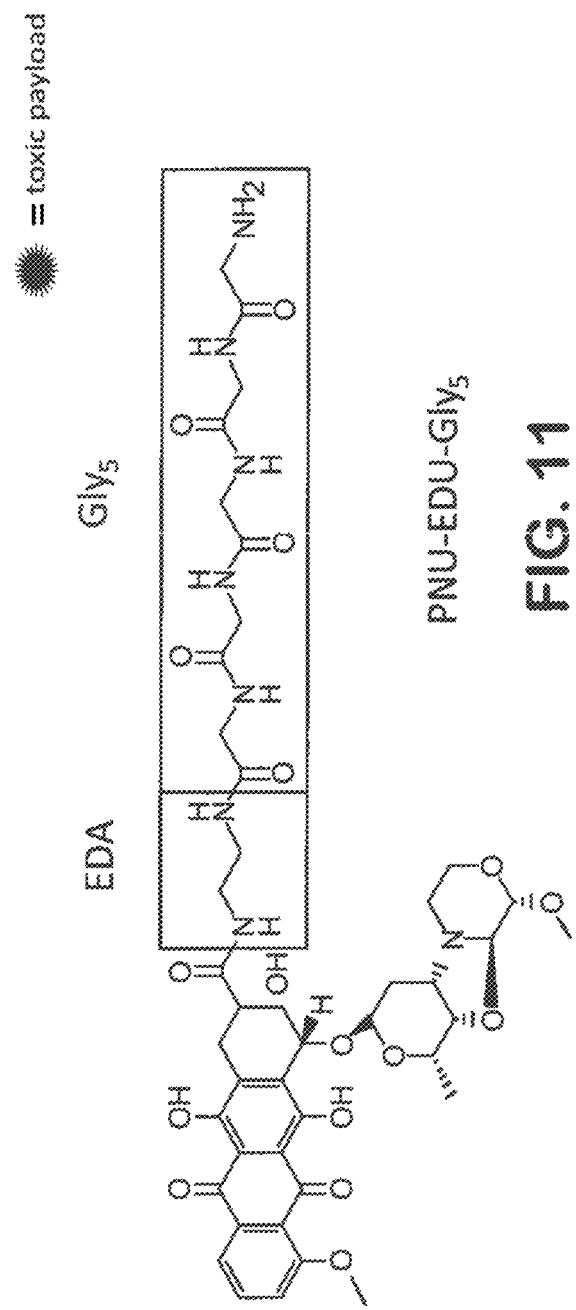

In the embodiment where the synthetic molecule is of formula (i), it is preferred that the linker comprise an alkyldiamino group of the form $NH_2$—$(CH_2)_m$—$NH_2$, where m≥1 and ≤11, preferably m=2, such that one amino group is directly linked at the wavy line of formula (i) to form an amide bond. It is moreover preferred that the second amino group is linked to an oligopeptide linker, which is more preferably an oligoglycine $Gly_{(n)}$, with n being ≥1 and ≤21. The most preferred payload is shown in FIG. 11 (B).

In some embodiments, the synthetic molecule can be conjugated to any antibody, antibody-based binding protein, or antibody-fragment. In some embodiments, the synthetic molecule can be a label. Labels can be useful in diagnostic applications and can include, for example, contrast agents. A contrast agent can be a radioisotope label such as iodine ($^{131}$I or $^{125}$I) indium ($^{111}$In), technetium ($^{99}$Tc), phosphorus ($^{32}$P), carbon ($^{14}$C), tritium ($^{3}$H), other radioisotope (e.g., a radioactive ion), or a therapeutic radioisotope such as one of the therapeutic radioisotopes listed above. Additionally, contrast agents can include radiopaque materials, magnetic resonance imaging (MRI) agents, ultrasound imaging agents, and any other contrast agents suitable for detection by a device that images an animal body. A synthetic molecule can also be a fluorescent label, a biologically active enzyme label, a luminescent label, or a chromophore label.

In some other embodiments, the synthetic molecule can be a liposome, as described in Bendas, BioDrugs, 15: 215-224, 2001. In such embodiments, the antibody can be conjugated to a colloidal particle, e.g., a liposome, and used for controlled delivery of an agent to diseased cells. In preparing an antibody conjugated to a liposome, e.g., an immunoliposome, an agent such as a chemotherapeutic or other drug can be entrapped in the liposome for delivery to a target cell. In some embodiments, the antibodies, antibody-based binding proteins or antibody fragments thereof of the invention can also have specificity for one or more antigens in addition to ROR1. For example, the antibody of the invention can be engineered (e.g., as a bivalent diabody or a conjugated Fab dimer or trimer) to have specificity for ROR1 and another tumor antigen, e.g., an antigen associated with neuroblastoma, renal cell carcinoma, breast cancer, gastric cancer, prostate cancer, colon cancer (e.g., colon adenocarcinoma), or breast cancer (e.g., breast adenocarcinoma). The antibody can be engineered to have specificity for ROR1 and an antigen that promotes activation or targeting of cytotoxic effector cells.

IV. Polynucleotides, Vectors and Host Cells for Producing ROR1 Antibodies

The invention provides substantially purified polynucleotides (DNA or RNA) that are identical or complementary to sequences encoding polypeptides comprising segments or domains of the antibody, antibody-based binding protein or antibody fragment thereof chains described herein. In some embodiments, the polynucleotides of the invention encode the heavy chain or light chain domains sequences shown in FIGS. 1 and 23. When expressed from appropriate expression vectors, polypeptides encoded by these polynucleotides are capable of exhibiting ROR1 antigen binding capacity. Also provided in the invention are polynucleotides which encode at least one CDR region and usually all three CDR regions from the heavy or light chain of the antibodies described herein. Some other polynucleotides encode all or substantially all of the variable region sequence of the heavy chain and/or the light chain of the exemplified antibodies. For example, some of these polynucleotides encode the amino acid sequence of the heavy chain variable region shown in any one SEQ ID NOs:1-13 or 130-135, and/or the amino acid sequence of the light chain variable region shown in any one SEQ ID NOs:14-26 or 136-141. Because of the degeneracy of the code, a variety of nucleic acid sequences will encode each of the immunoglobulin amino acid sequences.

The polynucleotides of the invention can encode only the variable region sequences of the exemplified antibodies. They can also encode both a variable region and a constant region of the antibody. Some of polynucleotide sequences of the invention nucleic acids encode a mature heavy chain variable region sequence that is substantially identical (e.g., at least 80%, 90%, 95% or 99%) to the mature heavy chain variable region sequence shown in any one SEQ ID NOs: 1-13 or 130-135. Some other polynucleotide sequences encode a mature light chain variable region sequence that is substantially identical (e.g., at least 80%, 90%, 95% or 99%) to the mature light chain variable region sequence shown in any one SEQ ID NOs:14-26 or 136-141. Some of the polynucleotide sequences encode a polypeptide that comprises variable regions of the heavy chain or the light chain of one of the exemplified antibodies. Some other polynucleotides encode two polypeptide segments that respectively are substantially identical to the variable regions of the heavy chain or the light chain of one of the exemplified antibodies.

The polynucleotide sequences can be produced by de novo solid-phase DNA synthesis or by PCR mutagenesis of an existing sequence (e.g., sequences as described in the Examples below) encoding an exemplified functional antibody. Direct chemical synthesis of nucleic acids can be accomplished by methods known in the art, such as the phosphotriester method of Narang et al., Meth. Enzymol. 68:90, 1979; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., *PCR Technology: Principles and Applications for DNA Amplification*, H. A. Erlich (Ed.), Freeman Press, NY, NY, 1992; *PCR Protocols: A Guide to Methods and Applications*, Innis et al. (Ed.), Academic Press, San Diego, Calif., 1990; Manila et al., Nucleic Acids Res. 19:967, 1991; and Eckert et al., PCR Methods and Applications 1:17, 1991.

Also provided in the invention are expression vectors and host cells for producing the functional antibodies described herein. Specific examples of plasmid and transposon based vectors for expressing the antibodies are described in the Examples below. Various other expression vectors can also be employed to express the polynucleotides encoding the functional antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat. Genet. 15:345, 1997). For example, nonviral vectors useful for expression of the antibody polynucleotides and polypeptides in mammalian (e.g., human) cells include pCEP4, pREP4, pThioHis A, B & C, pcDNA3.1/His, pEBVHis A, B & C (Invitrogen, San Diego, Calif.), MPSV vectors, and numerous other vectors known in the art for expressing other proteins. Other useful nonviral vectors include vectors that comprise expression cassettes that can be mobilized with Sleeping Beauty, PiggyBack and other transposon systems. Useful viral vectors include vectors based on lentiviruses or other retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding a functional antibody chain or fragment. In some embodiments, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of a functional antibody chain or fragment. These elements typically include an ATG initiation codon and adjacent ribosome binding site (Kozak consensus sequence) or other sequences. In addition, the efficiency of expression may be enhanced by the inclusion of enhancers appropriate to the cell system in use (see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted functional antibody sequences. More often, the inserted functional antibody sequences are linked to a signal sequences before inclusion in the vector. Vectors to be used to receive sequences encoding the functional antibody light and heavy chain variable domains sometimes also encode constant regions or parts thereof. Such vectors allow expression of the variable regions as fusion proteins with the constant regions thereby leading to production of intact antibodies or fragments thereof. Typically, such constant regions are human, and preferably of human IgG1 antibodies.

The host cells for harboring and expressing the functional antibody chains can be either prokaryotic or eukaryotic. In some preferred embodiments, mammalian host cells are used to express and to produce the antibody polypeptides of the present invention. For example, they can be either a hybridoma cell line expressing endogenous immunoglobulin genes or a mammalian cell line harboring an exogenous expression vector. These include any normal mortal or normal or abnormal immortal animal or human cell. In addition to the cell lines exemplified herein, a number of other suitable host cell lines capable of secreting intact immunoglobulins are also known in the art. These include, e.g., the CHO cell lines, various HEK 293 cell lines, various Cos cell lines, HeLa cells, myeloma cell lines, transformed B-cells and hybridomas. The use of mammalian tissue cell culture to express polypeptides is discussed generally in, e.g., Winnacker, From Genes to Clones, VCH Publishers, N.Y., N.Y., 1987. Expression vectors for mammalian host cells can include expression control sequences, such as an origin of replication, a promoter, and an enhancer, and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, EFla and human UbC promoters exemplified herein, the metallothionein promoter, the constitutive adenovirus major late promoter, the dexamethasone-inducible MMTV promoter, the SV40 promoter, the MRP pol III promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transformation is commonly utilized for prokaryotic cells, whereas calcium phosphate treatment or electroporation may be used for other cellular hosts (see generally Sambrook et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the antibody chains or binding fragments can be prepared using expression vectors of the invention which contain viral origins of replication or endogenous expression elements and a selectable marker gene. Following introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate for the cell type.

The invention further provides eukaryotic or non-eukaryotic cells (e.g., T lymphocytes) that have been recombinantly engineered to produce the antibodies, antibody-based binding proteins or antibody fragments thereof of the invention. The eukaryotic or non-eukaryotic cells can be used as an expression system to produce the antibody of the invention. In some embodiments, the invention provides ROR1 targeted immune cells that are engineered to recombinantly express an ROR1 specific antibody of the invention. For example, the invention provides a T cell engineered to express an antibody of the invention (e.g., an scFv, scFv-Fc, or (scFv)2), which is linked to a synthetic molecule containing one or more of the following domains: a spacer or hinge region (e.g., a CD28 sequence or a IgG4 hinge-Fc sequence), a transmembrane region (e.g., a transmembrane canonical domain), and an intracellular T-cell receptor (TCR) signaling domain, thereby forming a chimeric antigen receptor (CAR) or T-body. Intracellular TCR signaling domains that can be included in a CAR (or T-body) include, but are not limited to, CD3ζ, FcR-γ, and Syk-PT signaling domains as well as the CD28, 4-1BB, and CD134 co-signaling domains. Methods for constructing T-cells expressing a CAR (or T-body) are known in the art. See, e.g., Marcu-Malina et al., Expert Opinion on Biological Therapy, Vol. 9, No. 5 (posted online on Apr. 16, 2009).

V. Therapeutic and Diagnostic Applications

The ROR1 antibodies, antibody-based binding proteins, antibody fragments thereof, ADCs and CARs disclosed herein can be used in various therapeutic and diagnostic applications. ROR1 is expressed and implicated in the development of various tumors. See, e.g., Rebagay et al., Front Oncol. 2, 34, 2012; and Shabani et al., Expert Opin. Ther. Targets 19, 941-955, 2015. For example, ROR1 is expressed on the tumor cell surface in CLL, ALL, mantle cell lymphoma, neuroblastoma, sarcoma, renal cell carcinoma, breast cancer, lung cancer, colon cancer, head and neck cancer, melanoma, and other cancers. Importantly, ROR1 is expressed in embryogenesis but largely shut down after birth. Very few adult healthy tissues and cells express ROR1. Consistently, anti-ROR1 CAR-engineered T cells were found to be safe and active in nonhuman primates, validating ROR1 as a therapeutic target in cancer (Berger (2015) *Cancer Immunol Res.* 3(2), page 2016). Thus, mAbs to ROR1 have high therapeutic and diagnostic utility in cancer.

In some embodiments, the invention provides methods for inhibiting cells that express ROR1 (ROR1 cells) by contacting the cells with an antibody, antibody-based binding protein, antibody fragment thereof, ADC or CAR of the invention. The antibody, antibody-based binding protein or antibody fragment thereof can be a naked (unconjugated) molecule or an antibody, antibody-based binding protein, antibody fragment thereof conjugated to a synthetic molecule, e.g., a cytotoxic, cytostatic, or antiangiogenic agent, a radioisotope, or even to a liposome. Preferably, cells are contacted with an ADC comprising a conjugated cytotoxic molecule. The method can be used to inhibit ROR1 cells in vitro or in a subject (i.e., in vivo). The contacted ROR1 cells can be in, for example, a cell culture or animal model of a disorder associated with elevated levels of ROR1. The methods are useful, for example, to measure and/or rank (relative to another antibody) the antibody's inhibitory activity for a specific ROR1 cell type. Inhibiting ROR1 cells can include blocking or reducing the activity or growth of ROR1 cells. Inhibiting can also include the killing of ROR1 cells. While the methods are not bound by or limited to any particular mechanism of action, inhibitory activity can be mediated by blocking ROR1-mediated signaling or by blocking the signaling of an ROR1 associated receptor. Inhibitory activity can also be mediated by recruitment of immune system effectors that attack ROR1 cells, e.g., by activating constituents of the antibody-dependent cell-mediated cytotoxicity (ADCC) or complement systems.

In some related embodiments, the invention provides methods for treating a subject that has, is suspected to have, or is at risk of developing a disorder associated with expression of ROR1. Generally, the methods include administering a therapeutically effective amount of an isolated antibody, antibody-based binding protein, antibody fragment thereof, ADC or CAR of the invention to the subject. The antibody can be any anti-ROR1 antibody, anti-ROR1 antibody fragment, anti-ROR1 antibody-based binding protein of the invention as described herein. Thus, the antibody can be chimeric, humanized, synthetic, F(ab)2, Fv, scFv, IgGACH2, F(ab')2, scFv2CH3, Fab, VL, VH, scFv4, scFv3, scFv2, dsFv, Fv, or (scFv)2. In some embodiments, the method includes administering an IgG, an scFv, a dsFv, a F(ab')2, a diabody, or a bivalent antibody. The administered antibody, antibody-based binding protein, antibody fragment thereof can be conjugated to a synthetic molecule described above, e.g., a cytotoxic, cytostatic, or antiangiogenic agent, a therapeutic radioisotope, or a liposome. An exemplary cytotoxic agent is *Pseudomonas* exotoxin A (PE38). Disorders that can be treated include CLL, ALL, mantle cell lymphoma, neuroblastoma, sarcoma, renal cell carcinoma, breast cancer, lung cancer, colon cancer, head and neck cancer, melanoma, and other disorders with elevated ROR1 expression.

In some embodiments, the invention provides methods for treating a subject that has, is suspected to have, or is at risk of developing a disorder associated with elevated levels of ROR1 by adoptive transfer of the genetically engineered T-cells described herein, which express an antibody or antigen-binding fragment of the invention as a chimeric antigen receptor (CAR) that selectively binds ROR1. Recombinant technology can be used to introduce CAR-encoding genetic material into any suitable T-cells, e.g., central memory T-cells from the subject to be treated. The T cells carrying the genetic material can be expanded (e.g., in the presence of cytokines). The genetically engineered T-cells are transferred, typically by infusion, to the patient. The transferred T-cells of the invention can then mount an immune response against ROR1 expressing cells in the subject. The adoptive transfer method can be used, for example, to treat subjects that have or are suspected to have any of the cancers associated with ROR1, including CLL, ALL, mantle cell lymphoma, neuroblastoma, sarcoma, renal cell carcinoma, breast cancer, lung cancer, colon cancer, head and neck cancer, melanoma, and other cancers. In some embodiments, the foregoing methods of treatment can further include co-administering a second therapeutic agent for treating the disorder associated with elevated ROR1. For example, when the disorder to be treated involves an ROR1-expressing cancer, the method can further include co-administration of a cytotoxic, cystostatic, or antiangiogenic or immune-stimulatory agent (e.g. immune-checkpoint inhibitor antibodies, for instance, but not limited to, those binding to PD1, PDL1, CTLA4, OX40, TIM3, GITR, LAG3 and the like) suitable for treating the cancer. If the cancer is a B-cell malignancy, the method can further include, for example, co-administration of rituximab, alemtuzumab, ofatumumab, ocrelizumab, or a CHOP chemotherapeutic regimen.

In some other embodiments, the invention provides method for detecting in a biological sample an altered level of ROR1 (e.g., cell surface ROR1), for example, relative to a control, either by FACS, immunohistochemistry (IHC) or Western Blotting. Generally, the method includes contacting a biological sample with an antibody, antibody-based binding protein, antibody fragment thereof of the invention and determining the amount of antibody that selectively binds to material (e.g., cells) in the sample to thereby determine the level of ROR1 in the biological sample. A biological sample can be from a cell culture or from a test subject, e.g., a plasma or a tissue sample from a subject that has, is suspected to have, or is at risk of developing a disease or condition associated with elevated ROR1 in a subject. A control level desirably corresponds to the ROR1 level detected using the same antibody in a corresponding sample(s) from one or more control cultures or disease-free subjects. Methods of using the antibody of the invention to determine ROR1 levels can include any immunoassay such as immuno-(Western) blotting, enzyme-linked immunosorbent assay (ELISA), Immunohistochemistry (IHC) and flow cytometry, e.g., fluorescence-activated cell sorting (FACS) analysis.

The methods of detection can be used to screen for the presence of a disorder associated with elevated ROR1. The methods include obtaining a sample from a test subject in need of screening, e.g., a subject that has, is suspected to have, or is at risk of developing a disorder associated with elevated ROR1. The level of ROR1 (e.g., the amount or concentration) in the sample is measured using an antibody, antibody-based binding protein, antibody fragment thereof of the invention, and the level in the sample is compared to a control level of ROR1. The control level represents, for example, the mean level (e.g., the amount or concentration) in sample(s) from one or, preferably, multiple control group subjects that do not have a disorder associated with elevated ROR1. Alternatively, the control level can correspond to the level or mean level of ROR1 in one or more samples taken from the test subject at one or more prior times, such as when the test subject did not have or did not exhibit, a condition associated with elevated ROR1. A significantly higher level of ROR1 in the biological sample relative to the control level is indicative of a disorder associated with elevated ROR1 in the subject. In subjects such as humans, where cell surface ROR1 expression is largely restricted to embryonic development, a control level of ROR1 can be zero or none. Thus, in some embodiments of the method of the detection provided by the invention, any significant and detectable amount of ROR1 in a biological sample can be indicative of a disorder associated with elevated ROR1 in the subject.

Additionally, the methods of detection can be used to monitor the progress of a disorder associated with elevated ROR1. The method includes obtaining a sample from a subject in need of screening, e.g., a subject having been diagnosed or suspected to have a disorder associated with elevated ROR1. The level of ROR1 in the sample is measured using an antibody, antibody-based binding protein, antibody fragment thereof of the invention, and the level in the sample is compared to a control level corresponding to the level or mean level of ROR1 in one or more samples taken from the test subject at one or more prior times. Levels of ROR1 that are significantly elevated or decreased relative to control indicate that the subject's disorder is deteriorating or improving, respectively. The foregoing methods of detection can be used to screen for the presence or to monitor the progress of disorders including, for example, CLL, ALL, mantle cell lymphoma, neuroblastoma, sarcoma, renal cell carcinoma, breast cancer, lung cancer, colon cancer, head and neck cancer, melanoma, and other cancers.

In some embodiments, the invention provides methods for screening a subject for an altered level of ROR1. Generally, the methods entail administering to the subject an antibody, antibody-based binding protein, antibody fragment thereof of the invention that is conjugated to a label (e.g., a contrast agent), imaging the subject in a manner suitable for detecting the label, and determining whether a region in the subject has an altered density or concentration of label as compared to the background level of label in proximal tissue. Alternatively, the methods include determining whether there is an altered density or concentration of label in a region as compared to the density or concentration of label previously detected in the same region of the subject. Methods of imaging a subject can include x-ray imaging, x-ray computed tomography (CT) imaging (e.g., CT angiography (CTA) imaging), magnetic resonance (MR) imaging, magnetic resonance angiography (MRA), nuclear medicine, ultrasound (US) imaging, optical imaging, elastography, infrared imaging, microwave imaging, and the like, as appropriate for detecting the label conjugated to the antibody. In a preferred embodiment, the subject has, is suspected to have, or is at risk of developing an ROR1-expressing tumor, such as CLL, ALL, mantle cell lymphoma, neuroblastoma, sarcoma, renal cell carcinoma, breast cancer, lung cancer, colon cancer, head and neck cancer, melanoma, and other cancers, and the method is used to screen for or detect the presence of the tumor. In another embodiment, the method can be used to monitor the size or density of a ROR1-expressing tumor over time, e.g., during a course of treatment.

VI. Pharmaceutical Compositions and Combinations

In another aspect, the invention provides pharmaceutical compositions that contain an antibody, an antibody fragment, an antibody-based binding protein, or an ADC as described herein and a pharmaceutically acceptable carrier. Pharmaceutical compositions can be prepared from any of the antibodies described herein. Exemplary compositions include one or more of a chimeric antibody having SEQ ID NO:14 (light chain) and/or SEQ ID NO:1 (heavy chain), a chimeric antibody having SEQ ID NO:18 (light chain) and/or SEQ ID NO:5 (heavy chain), a chimeric antibody having SEQ ID NO:25 (light chain) and/or SEQ ID NO:12 (heavy chain), and a chimeric antibody having SEQ ID NO:26 (light chain) and/or SEQ ID NO:13 (heavy chain). Other antibodies, antibody fragments, antibody-based binding proteins, or ADCs suitable for the pharmaceutical compositions of the invention include those having a light chain sequence as shown in SEQ ID NOs:14-26 or 136-141, and/or a heavy chain sequence as shown in SEQ ID NOs: 1-13 or 130-135. Other exemplary compositions of the invention can contain a humanized antibody having one, two, three, four, five, or six CDRs selected from the group consisting of SEQ ID NOs:27-104, like the ones exemplified in SEQ ID NOs: 130-141 In some embodiments the antibody includes three CDR sequences of the same exemplified light or heavy chains shown in FIG. 1. These include the heavy chain CDR1, CDR2 and CDR3 sequences and light chain CDR1, CDR2 and CDR3 sequences respectively shown in (1) SEQ ID NOs:27-29 and SEQ ID NOs:66-68 (antibody XBR1-402), (2) SEQ ID NOs:30-32 and SEQ ID NOs:69-71 (antibody ERR1-301), (3) SEQ ID NOs:33-35 and SEQ ID NOs:72-74 (antibody ERR1-306), (4) SEQ ID NOs:36-38 and SEQ ID NOs:75-77 (antibody ERR1-316), (5) SEQ ID NOs:39-41 and SEQ ID NOs:78-80 (antibody ERR1-324), (6) SEQ ID NOs:42-44 and SEQ ID NOs:81-83 (antibody ERR1-403), (7) SEQ ID NOs:45-47 and SEQ ID NOs:84-86 (antibody ERR1-409), (8) SEQ ID NOs:48-50 and SEQ ID NOs:87-89 (antibody ERR1-TOP4), (9) SEQ ID NOs:51-53 and SEQ ID NOs:90-92 (antibody ERR1-TOP15), (10) SEQ ID NOs:54-56 and SEQ ID NOs:93-95 (antibody ERR1-TOP22), (11) SEQ ID NOs:57-59 and SEQ ID NOs:96-98 (antibody ERR1-TOP40), (12) SEQ ID NOs: 60-62 and SEQ ID NOs:99-101 (antibody ERR1-TOP43), or (13) SEQ ID NOs:63-65 and SEQ ID NOs:102-104 (antibody ERR1-TOP54). In some embodiments, the pharmaceutical composition includes an antibody having six CDR sequences of the same antibody exemplified in FIG. 1, e.g., (a) SEQ ID NOs:66-68 and SEQ ID NOs:27-29 (antibody XBR1-402); (b) SEQ ID NOs:78-80 and SEQ ID NOs:39-41(antibody ERR1-324); (c) SEQ ID NOs:99-101 and SEQ ID NOs:60-62 (antibody ERR1-TOP43), or (d) SEQ ID NOs:102-104 and SEQ ID NOs:63-65 (antibody ERR1-TOP54). Still another exemplary pharmaceutical composition includes a dsFv fragment, which can include one or more modifications to the amino acid sequence as appropriate and understood by one of ordinary skill in the art.

In some embodiments, the compositions of the invention contain a carrier for the antibody, the antibody fragment, the antibody-based binding protein or the ADC, desirably a pharmaceutically acceptable carrier. The pharmaceutically acceptable carrier can be any suitable pharmaceutically acceptable carrier. It can be one or more compatible solid or liquid fillers, diluents, other excipients, or encapsulating substances which are suitable for administration into a human or veterinary patient (e.g., a physiologically acceptable carrier or a pharmacologically acceptable carrier). The term "carrier" denotes an organic or inorganic ingredient, natural or synthetic, with which the active ingredient is combined to facilitate the use of the active ingredient, e.g., the administration of the active ingredient to a subject. The pharmaceutically acceptable carrier can be co-mingled with one or more of the active components, e.g., a hybrid molecule, and with each other, when more than one pharmaceutically acceptable carrier is present in the composition, in a manner so as not to substantially impair the desired pharmaceutical efficacy. Pharmaceutically acceptable materials typically are capable of administration to a subject, e.g., a patient, without the production of significant undesirable physiological effects such as nausea, dizziness, rash, or gastric upset. It is, for example, desirable for a composition comprising a pharmaceutically acceptable carrier not to be immunogenic when administered to a human patient for therapeutic purposes.

Pharmaceutical compositions of the invention can additionally contain suitable buffering agents, including, for example, acetic acid in a salt, citric acid in a salt, boric acid in a salt, and phosphoric acid in a salt. The compositions can also optionally contain suitable preservatives, such as benzalkonium chloride, chlorobutanol, parabens, and thimerosal. Pharmaceutical compositions of the invention can be presented in unit dosage form and can be prepared by any suitable method, many of which are well known in the art of pharmacy. Such methods include the step of bringing the antibody of the invention into association with a carrier that constitutes one or more accessory ingredients. In general, the composition is prepared by uniformly and intimately bringing the active agent into association with a liquid carrier, a finely divided solid carrier, or both, and then, if necessary, shaping the product.

A composition suitable for parenteral administration conveniently comprises a sterile aqueous preparation of the inventive composition, which preferably is isotonic with the blood of the recipient. This aqueous preparation can be formulated according to known methods using suitable dispersing or wetting agents and suspending agents. The sterile injectable preparation also can be a sterile injectable solution or suspension in a non-toxic parenterally-acceptable diluent or solvent, for example, as a solution in 1,3-butane diol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed, such as synthetic mono-or di-glycerides. In addition, fatty acids such as oleic acid can be used in the preparation of injectables. Carrier formulations suitable for oral, subcutaneous, intravenous, intramuscular, etc. administrations can be found in Remington's Pharmaceutical Sciences, Mack Publishing Co., Easton, Pa.

Preparation of pharmaceutical compositions of the invention and their various routes of administration can be carried out in accordance with methods well known in the art. See, e.g., Remington: *The Science and Practice of Pharmacy*, Mack Publishing Co., 20$^{th}$ ed., 2000; and *Sustained and Controlled Release Drug Delivery Systems*, J. R. Robinson, ed., Marcel Dekker, Inc., New York, 1978. The delivery systems useful in the context of the invention include time-released, delayed release, and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain compositions of the invention.

Many types of release delivery systems are available and known to those of ordinary skill in the art. Suitable release delivery systems include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and triglycerides; hydrogel release systems; sylastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The invention also provides kits suitable for carrying out the methods of the invention. Typically, the kits contain two or more components required for performing the therapeutic or diagnostic methods of the invention. Kit components include, but are not limited to, one or more antibodies, antibody-based binding proteins, antibody fragments thereof, or ADC of the invention, appropriate reagents, and/or equipment. In some embodiments, the kits can contain an antibody, antibody-based binding protein, antibody fragment thereof of the invention and an immunoassay buffer suitable for detecting ROR1 (e.g. by ELISA, flow cytometry, magnetic sorting, or FACS). The kit may also contain one or more microtiter plates, standards, assay diluents, wash buffers, adhesive plate covers, magnetic beads, magnets, and/or instructions for carrying out a method of the invention using the kit. The kit scan include an antibody, antibody-based binding proteins, antibody fragments thereof of the invention bound to a substrate (e.g., a multi-well plate or a chip), which is suitably packaged and useful to detect ROR1. In some embodiments, the kits include an antibody, antibody-based binding proteins, antibody fragments thereof of the invention that is conjugated to a label, such as, a fluorescent label, a biologically active enzyme label, a luminescent label, or a chromophore label. The kits can further include reagents for visualizing the conjugated antibody, antibody-based binding proteins, antibody fragments thereof, e.g., a substrate for the enzyme. In some embodiments, the kits include an antibody, antibody-based binding proteins, antibody fragments thereof of the invention that is conjugated to a contrast agent and, optionally, one or more reagents or pieces of equipment useful for imaging the antibody in a subject.

Generally the antibody, antibody-based binding proteins, antibody fragments thereof of the invention in a kit is suitably packaged, e.g., in a vial, pouch, ampoule, and/or any container appropriate for a therapeutic or detection method. Kit components can be provided as concentrates (including lyophilized compositions), which may be further diluted prior to use, or they can be provided at the concentration of use. For use of the antibody of the invention in vivo, single dosages may be provided in sterilized containers having the desired amount and concentration of components.

EXAMPLES

The following examples are provided to further illustrate the invention but not to limit its scope. Other variants of the invention will be readily apparent to one of ordinary skill in the art and are encompassed by the appended claims.

Example 1. Cell Lines

Cell Lines:

MDA-MB-231, MDA-MB-469, 697, Kasumi-2, T47D, HS578T, 63-12 and 63-12/hROR1 and 63-12/hROR2 transfectants, K562 and K562/hROR1 transfectants, EMT-6 and EMT-6/ROR1 transfectants were cultured in DMEM (Invitrogen; Carlsbad, Calif.) supplemented with 10% (v/v) heat inactivated FBS (Thermo Scientific; Logan, Utah), 100 U/mL penicillin, and 100 mg/mL streptomycin (Invitrogen). HEK 293F cells were purchased from Invitrogen and maintained in FreeStyle Medium supplemented with 1% (v/v) heat inactivated FBS (Thermo Scientific) to support adherent culture or without FBS for suspension culture, 100 U/mL penicillin, and 100 mg/mL streptomycin (Invitrogen).

Cloning of Full-Length hROR1 and hROR1 Mammalian Expression Vectors:

Transposable vector backbones (pPB-Puro) were assembled from modular parts with flanking restriction sites that were synthesized or derived from sequence-verified commercially available vectors, and are described in detail in Patent WO2014013026A1. These original transposable vector backbones were modified by exchanging IRES-driven expression of the Puromycin resistance gene in the original vector with separate, phosphoglycerate kinase promoter (PGK) driven expression. This was done by replacing the IRES sequence with an SV40-pA sequence located 3' of the multiple cloning site, followed by introduction of the PGK-promoter sequence 5' of the Puromycin resistance gene. Full-length ROR1/2 open reading frames were synthesized by total gene synthesis (Genscript, Piscataway) with flanking restriction sites (5'NotI/3'BstBI) and were then cloned into the multiple cloning site of the transposable vectors using the respective restriction enzymes.

Cell Line Engineering for Ectopic Expression of hROR1 or hROR2 in the 63-12 Murine A-MuLV-Transformed preB Cell Line:

The mouse Abelson murine pre-B cell line 63-12 (Shinkai et al. (1992) Cell 68:855-67) were cultured in culture media (17.7 g/L Gibco® IMDM (Life Technologies, 42200-030), 3.024 g/L NaHCO$_3$(Sigma-Aldrich, p.a., >99.7%), 10 mL/L 100× non-essential amino acids (Life Technologies, 11140035), 5 mg/L insulin (Sigma-Aldrich, I-5500), 3 mL/L of 10% primatone RL/UF in H$_2$O (Sheffield Bioscience), and 1 mL/L of 50 mM 2-mercaptoethanol (Sigma-Aldrich, M-3148) in H$_2$O), supplemented with 2% (v/v) FCS, 100 IU/mL Pen/Strep/Fungizone (Amimed, 4-02F00-H), 200 mM L-glutamine (Amimed, 5-10K00-H) and 50 µM 2-mercaptoethanol (Amresco, 0482) at 37° C. and 7.5% CO$_2$. Cells were engineered to overexpress hROR1 and hROR2 by transposition as follows: cells were centrifuged (6 min, 1200 rpm, 4° C.) and resuspended in RPMI-1640 media (5×10$^6$ cells/mL). 400 µL of cell suspension was then added to 400 µL of RPMI containing 10 µg of transposable vector pPB-PGK-Puro-ROR1 (directing co-expression of full-length ROR1 (NP_005003.2) and the puromycin-resistance gene), or 10 µg of transposable vector pPB-PGK-Puro-ROR2 (directing co-expression of full-length ROR2 (NP_004551.2) and the puromycin-resistance gene), along with 10 µg of transposase-containing vector pCDNA3.1_hy_mPB. DNA/63-12 cell mixtures were transferred to electroporation cuvettes (0.4 cm-gap, 165-2088, BioRad, Cressier, Switzerland) and electroporated using the Biorad Gene Pulser II with capacitance extender at 300V and 950 µf. Then, cells were incubated for 5-10 min at room temperature. Following the incubation, cells were centrifuged at 1200 rpm for 6 min (4° C.), washed once and subsequently resuspended in aqueous culture media (17.7 g/L Gibco® IMDM (Life Technologies, 42200-030), 3.024 g/L NaHCO$_3$(Sigma-Aldrich, p.a., >99.7%), 10 mL/L 100× non-essential amino acids (Life Technologies, 11140035), 5 mg/L insulin (Sigma-Aldrich, I-5500), 3 mL/L of 10% primatone RL/UF in H$_2$O (Sheffield Bioscience), and 1 mL/L of 50 mM 2-mercaptoethanol (Sigma-Aldrich, M-3148) in H$_2$O), supplemented with 2% (v/v) FCS, 100 IU/mL Pen/Strep/Fungizone (Amimed, 4-02F00-H), 200 mM L-glutamine (Amimed, 5-10K00-H) and 50 µM 2-mercaptoethanol (Amresco, 0482). After two days incubation at 37° C. in a humidified incubator at 5% CO$_2$ atmosphere, cell pools stably expressing hROR1 or hROR2 were selected by adding 2 µg/mL puromycin (Sigma-Aldrich, P8833).

After 4 to 5 days, hROR1 or hROR2 expression on engineered cells were confirmed by flow cytometry. Briefly, following trypzinization, 10$^6$ cells were centrifuged in FACS tubes; obtained pellets were resuspended in buffer (PBS with 2% (v/v) FCS). In the case of hROR1-engineered cells, cells were then incubated with 2A2 (mAb066 antibody targeting ROR1, final concentration 2 µg/mL) for 30 min at 4° C., followed by centrifugation and washing. Cells were resuspended as previously and incubated with anti-human IgG antibody (Fc gamma-specific) PE (eBioscience, Vienna, Austria, 12-4998-82), at a 1:100 dilution, in the dark (30 min, 4° C.), washed once in buffer and kept on ice until FACS sorting. For hROR2-engineered 63-12 cells, the same protocol was followed but using EPR3779 (Abcam antibody targeting ROR2; 1:100 dilution) as primary antibody and allophycocyanin-conjugated AffiniPure F(ab')2 goat anti-rabbit IgG (H+L) (Jackson Immunoresearch, 111-136-144) as secondary antibody.

In the case of hROR1-engineered 63-12 cells, cells were single cell sorted into 96-well flat-bottom plates containing 200 µL of supplemented culture media per well using a FACS Aria II. Plates were incubated at 37° C. and clones were expanded to 6-well plates before analysis. Target expression was confirmed by flow cytometry using a FACSCalibur instrument (BD Biosciences) and FlowJo analytical software (Tree Star, Ashland, Oreg.).

Cell Line Engineering for Ectopic Expression of hROR1 in the EMT-6 Murine Breast Cancer Cell Line:

Murine EMT-6 breast cancer cells (kind gift from Prof. Dr. med. Alfred Zippelius, University Hospital of Basel, Switzerland) were cultured in DMEM complete (Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept, Allschwil, Switzerland)) at 37° C. and 5% CO$_2$. Cells were engineered to overexpress ROR1 by transposition as follows: cells were centrifuged (6 min, 1200 rpm, 4° C.) and resuspended in RPMI-1640 media (5×10$^6$ cells/mL). 400 µL of this cell suspension was then added to 400 µL of RPMI containing 13.3 µg of transposable vector pPB-PGK-Puro-ROR1, directing co-expression of full-length ROR1 (NP_005003.2) and the puromycin-resistance gene, and 6.6 µg of transposase-containing vector pCDNA3.1_hy_mPB. DNA/EMT-6 cell mixture was transferred to electroporation cuvettes (0.4 cm-gap, 165-2088, BioRad, Cressier, Switzerland) and electroporated using the Biorad Gene Pulser II with capacitance extender at 300V and 950 µf. Then, cells were incubated for 5-10 min at room-temperature. Following the incubation, cells were centrifuged at 1200 rpm for 6 min, washed once and subsequently resuspended in DMEM complete prior to incubation at 37° C. in a humidified incubator at 5% CO$_2$ atmosphere. One day after electroporation, cell pools stably expressing human ROR1 were selected by adding 3 µg/mL puromycin (Sigma-Aldrich, P8833).

ROR1 expression on selected EMT-6-ROR1 cells was confirmed by flow cytometry. Briefly, following trypsinization, 10$^6$ cells were centrifuged in FACS tubes; obtained pellets were resuspended in buffer (PBS with 2% (v/v) FCS). Cells were then incubated with 2A2 (mAb066); 30 min, 4° C., final concentration 2 µg/mL), followed by centrifugation and washing. Cells were then resuspended as previously and incubated with anti-human IgG antibody (Fc gamma-specific) PE (eBioscience, Vienna, Austria, 12-4998-82) with a 1:250 dilution in the dark (30 min, 4° C.), washed once in buffer and kept on ice until FACS sorting.

Using a FACS Aria II, cells were single cell sorted into a 96-well flat-bottom plate containing 200 µL of DMEM complete per well. This plate was incubated at 37° C. and clones were expanded to 6-well plates before analysis of ROR1-expression by flow cytometry as outlined above, using a FACSCalibur instrument (BD Biosciences) and FlowJo analytical software (Tree Star, Ashland, Oreg.) for analysis.

FIG. 16C shows the FACS analysis data of clone 14 (high ROR1-expressing) and WT (ROR1 negative) EMT-6, detected with anti-ROR1 antibody 2A2 (mAb066).

Example 2. Generation of High-Complexity Rabbit Fab Library and Reagents for Screening Construction, Expression, and Purification of Recombinant Human ROR1 Proteins: Construction, expression, purification and biotinylation of hFc fusion proteins containing different domains of human ROR1 or mouse ROR1 were described (Yang et al., PloS One 6:e21018, 2011). For hROR1-AVI-6×HIS fusion protein, the extracellular domain of human ROR1 (24-403) was PCR amplified with primers pCEP4-hROR1-F and pCEP4-hROR1-Avi tag-R (note that the AVI tag was introduced to the C terminus of ROR1 by primer pCEP4-hROR1-Avi tag-R), followed by extension PCR with primers pCEP4-signal-F-KpnI and pCEP4-6HIS—R-XhoI to add a signal peptide and 6×HIS tag to the N and C terminus separately before cloning into pCEP4 via KpnI/XhoI. This construct was then transiently transfected into HEK 293F cells (Invitrogen) using 293fectin (Invitrogen), and the protein was purified by Immobilized Metal Ion Affinity Chromatography using a 1-mL HisTrap column (GE Healthcare) as described in Kwong and Rader, Curr Protoc Protein Sci Chapter 6:Unit 6 10, 2009. The quality and quantity of purified hROR1-AVI-6×HIS was analyzed by SDS-PAGE and Also absorbance, respectively. Subsequently, the fusion protein was biotinylated by BirA enzyme kit from Avidity (Aurora, Colo.) following the protocol. Briefly, 2 mg ROR1-AVI-6×HIS at 40 04 in 10 mM Tris-HCl (pH 8) was biotinylated in the presence of biotin using 10 μg BirA after incubation for 30 min at 37° C., followed by purification again using a 1-mL HisTrap column (GE Healthcare) as described above.

pCEP4-hROR1-F:
(SEQ ID NO: 105)
5'-atcctgtttctcgtagctgctgcaactggagcacactccgcccg gggcgccgccgcccag-3';

pCEP4-hROR1-Avi-tag-R:
(SEQ ID NO: 106)
5'-ccactcgatcttctgggcctcgaagatgtcgttcaggccctcca tcttgttcttctccttt-3';

pCEP4-signal-F-KpnI:
(SEQ ID NO: 107)
5' gctgggtaccggcgcgccaccatggactggacttggagaatcct gtttctcgtagctgct-3';

pCEP4-6HIS-R-XhoI:
(SEQ ID NO: 108)
5'-gccggcctcgagtcagtgatggtgatggtggtgctcgtgccact cgatcttctgggcctc-3'.

Construction, expression, and purification of recombinant human ROR1 (hROR1-His) and human ROR2 (hROR2-His) proteins: hROR1-His was PCR-amplified with primers SP-hROR1_F (5' gctgggtaccggcgcgccaccatggactggacttg-gagaatcctginctcgtagctgctgcaactggagcacactccgcccggggcgccgccgcccag 3') (SEQ ID NO:109) and hROR1-His_R (5' cggcctcgagtcagtgatggtgatggtggtgctccatcttgttcttctcctt 3') (SEQ ID NO:110) using pCEP4-hFc-hROR1 (Yang et al., PloS One 6:e21018, 2011) as template, while hROR2-His was PCR-amplified with primers SP-hROR2_F (gctgggtaccggcgcgccaccatggactggacttg-gagaatcctginctcgtagctgctgcaactggagcacactccgaagtggaggttctggatccg) (SEQ ID NO:111) and hROR2-His_R (cggcctcgagtcagtgatggtgatggtggtgccccatcttgctgctgtctcg) (SEQ ID NO:112) using pCEP4-hFc-hROR2 as template.

Then they are cloned into pCEP4 (Invitrogen) separately via KpnI/XhoI. These constructs were then separately and transiently transfected into HEK 293F cells (Invitrogen) using 293fectin (Invitrogen), and the corresponding proteins were purified by Immobilized Metal Ion Affinity Chromatography using a 1-mL HisTrap column (GE Healthcare) as described in Kwong and Rader, Curr Protoc Protein Sci Chapter 6:Unit 6 10, 2009. The quality and quantity of purified hROR1-His and hROR2-His were analyzed by SDS-PAGE and $A_{280}$ absorbance, respectively.

Generation and Selection of Naïve Chimeric Rabbit/Human Fab Libraries:

All rabbit handling was carried out by veterinary personnel at Pocono Rabbit Farm & Laboratory (Canadensis, Pa.) or R & R Research (Stanwood, Wash.). A total of nine rabbits (ages 3-4 months) were used. Five of these rabbits were of the New Zealand White (NZW) strain, with three obtained from Pocono Rabbit Farm & Laboratory (Canadensis, Pa.) and two obtained from R & R Research (Stanwood, Wash.). Four b9 wild-type rabbits were derived from a separate R & R Research colony that originated from a pedigreed colony developed and characterized at the National Institute of Allergy and Infectious Diseases (NIAID) (McCartney-Francis et al., Proc. Natl. Acad. Sci. USA 81:1794-1798, 1984; and Popkov et al., J. Mol. Biol. 325:325-335, 2003. Spleen and bone marrow from each rabbit were collected and processed for total RNA preparation and RT-PCR amplification of rabbit $V_κ$, $V_λ$, and $V_H$ encoding sequences using established protocols (Rader, Methods Mol Biol 525:101-128, xiv, 2009. Rabbit (rb) $V_κ$/human (hu) $C_κ$/rb$V_H$ and rb$V_λ$hu$C_λ$/rb$V_H$ segments, respectively, were assembled in one fusion step based on 3-fragment overlap extension PCR. Note that the $V_L$ derived from b9 rabbits were also assembled with $V_H$ from NZW rabbits. The Fab-encoding fragments were digested with SfiI and ligated with SfiI-treated phage display vector pC3C (Hofer et al., J Immunol Meth 318:75-87, 2007) at 16° C. for 24 h. Subsequently, 15 μg purified pC3C-rb$V_κ$/h$C_κ$/rb$V_H$ ligated products were transformed into E. coli strain SR320 (a kind gift from Dr. Sachdev S. Sidhu, University of Toronto, Toronto, Ontario, Canada) by 30 separate electroporations (each using 0.5 μg DNA in 50 μl electrocompetent cells) and yielded 7.5×10$^9$ independent transformants for library λ. For library λ, 4.8×10$^9$ independent transformants were obtained using the same procedure. Using VCSM13 helper phage (Stratagene; La Jolla, Calif.), the phagemid libraries were converted to phage libraries and stored at −80° C. Phage library κ and library λ were re-amplified using XL1-Blue (Stratagene) or ER2738 (Lucigen) and mixed equally before four rounds of panning against biotinylated hFc-hROR1 or hROR1-AVI-6HIS. During the panning, 5 μg/mL antigen was pre-incubated with streptavidin coated magnetic beads (Dynabeads MyOne Streptavidin C1; Invitrogen) at 37° C. for 30 min and then binders from the phage library were captured in the presence of 1 mg/mL unspecific polyclonal human IgG (Thermo Scientific) when hFc-ROR1 was used. Starting from the third round of panning, the input phage was negatively depleted by incubation with empty beads before selection against antigen-loaded beads. Following selection, supernatants of IPTG-induced bacterial clones were analyzed by ELISA and by flow cytometry. Repeated clones were identified by DNA fingerprinting with AluI, and the $V_L$ and $V_H$ sequences of unique clones were determined by DNA sequencing (FIG. 1).

Example 3. Expression and Purification of Chimeric Rabbit/Human Fab and Full-Length IgG1 Antibodies Construction, Expression, and Purification of Chimeric Rabbit/Human Fab and IgG1:

MAb XBR1-402 in chimeric rabbit/human Fab format was cloned into *E. coli* expression plasmid pC3C-His and expressed and purified as described in Kwong and Rader, Curr Protoc Protein Sci Chapter 6:Unit 6 10, 2009. For the expression of mAb XBR1-402 in chimeric rabbit/human IgG1 format, the previously described vector PIGG-R11 was used (Yang et al., PloS One 6:e21018, 2011). The $V_H$ encoding sequence of Fab XBR1-402 was PCR amplified using primers 4-2_VH_F and 4-2_VH_R, and cloned via ApaI/SacI into PIGG-R11. Then the light chain encoding sequence of XBR1-402 was PCR amplified using primers 4-2_λ_F and LEAD-B, and cloned via HindIII/XbaI into PIGG-R11 with the corresponding heavy chain encoding sequence. Note that an internal ApaI site in FR4 of $V_H$ encoding sequences of Fab XBR1-402 was removed by silent mutation in primer 4-2_VH_R. In addition, we changed a TAG stop codon, which was suppressed during selection in *E. coli* strain XL1-Blue, to CAG (glutamine) encoding the first amino acid of native $V_H$ (FIG. 1) with primer 4-2_VH_F. The resulting PIGG-XBR1-402 plasmid was transiently transfected into HEK 293F cells (Invitrogen) using 293fectin (Invitrogen), and the protein purified with a 1-mL recombinant Protein A HiTrap column (GE Healthcare, Piscataway, N.J.) as described (Yang et al., PloS One 6:e21018, 2011; and Yang and Rader, Methods Mol Biol 901:209-232, 2012). The quality and quantity of purified IgG1 were analyzed by SDS-PAGE and $A_{280}$ absorbance, respectively.

All the other mAbs in chimeric rabbit/human Fab format were cloned into *E. coli* expression plasmid pET11a and expressed and purified as described (Yang et al., PloS One 6:e21018, 2011). For the expression of mAbs ERR1-324, ERR1-TOP43 and ERR1-TOP54 in chimeric rabbit/human IgG1 format, pCEP4 (Invitrogen) was used to clone the heavy chain and light chain separately. For heavy chain, a gBlock containing a heavy-chain signal peptide encoding sequence, $V_H$ of ERR2-302 (a mAb to hROR2) and CH1 (1-49) of human IgG1 was synthesized by IDT (San Jose, Calif.) and amplified with primers KpnI/AscI-Signal and CH1-internal/overlap-R, and fused to CH1 (50-88)-CH2-CH3 amplified from PIGG with primers CH1-internal/overlap-F and HC-CH3-R-XhoI by overlap extension PCR with primers KpnI/AscI-Signal and HC-CH3-R-XhoI, and then cloned into pCEP4 by AscI/XhoI. Note that a EheI site was introduced into CH1 at Ala[12] by synonymous mutation when the gBlock was synthesized. Consequently, this construct served as vector to clone the heavy chains of other mAbs by replacing the $V_H$ using AscI/EheI: $V_H$ of ERR1-324, ERR1-TOP43 and ERR1-TOP54 were amplified with forward primer ERR1-324 HC-F, ERR1-TOP43 HC-F and ERR1-TOP54 HC-F and reverse primer VH-CH1-R-EheI separately, followed by extension PCR to add the signal peptide with primer KpnI/AscI-Signal and VH-CH1-R-EheI. Then each $V_H$ was inserted into the vector by AscI/EheI. For light chain cloning, while lambda light chains of ERR1-TOP43 and ERR1-TOP54 were amplified with primers ERR1-TOP43 LC-F and ERR1-TOP54 LC-F separately combined with LC—R-XhoI, kappa light chains of ERR1-324 was amplified with primers ERR1-324 KC-F and KC—R-XhoI. Then, a signal peptide encoding sequence was added by extension PCR with forward primer KpnI/AscI-Signal and reverse primer LC—R-XhoI or KC—R-XhoI. Subsequently, each light chain PCR products was cloned into pCEP4 by AscI/XhoI. The resulting constructs containing heavy chain or light chain for each IgG were co-transfected transiently into HEK 293F cells (Invitrogen) using 293fectin (Invitrogen), and the corresponding proteins were purified with a 1-mL recombinant Protein A HiTrap column (GE Healthcare, Piscataway, N.J.) as described (Yang et al., PloS One 6:e21018, 2011; and Yang and Rader, Methods Mol Biol 901:209-232, 2012). The quality and quantity of purified IgG1 was analyzed by SDS-PAGE and $A_{280}$ absorbance, respectively.

TABLE 1

Primer sequences for cloning antibody sequences

| Primer | Sequence | SEQ ID NO: |
|---|---|---|
| 4-2_VH_F | gaggaggagctcactctcaggagcagcagaagga gtccggg | 113 |
| 4-2_VH_R | cgatgggcccttggtggaggctgaagagacggtg acgagggtccctggcccccagaggtc | 114 |
| 4-2_λ_F | gagaagcttgttgctctggatctctggtgcctac gggtcctatgagctgacacagctgcc | 115 |
| LEAD-B | ggccatggctggttgggcagc | 116 |
| KpnI/ AscI- Signal | ggtaccggcgcgccaccatggactggacttgg agaatcctgtttctcgtagctgctgcaa | 117 |
| CH1- internal/ overlap-R | gccgctggtcagggctcctg | 118 |
| CH1- internal/ overlap-F | caggagccctgaccagcggc | 119 |
| HC-CH3-R- XhoI | ggcctcgagtcatttacccggagacaggga | 120 |
| ERR1-324 HC-F | tttctcgtagctgctgcaactggagcacact cc cagtcgctggaggagtccggg | 121 |
| ERR1- TOP43 HC-F | tttctcgtagctgctgcaactggagcacact cc cagtcgttggaggagtccggg | 122 |
| ERR1- TOP54 HC-F | Same as ERR1-TOP43 HC-F | 123 |
| VH-CH1- R-EheI | ggagggcgccaggggaagaccgatgggccc ttggt | 124 |
| ERR1- TOP43 LC-F | tttctcgtagctgctgcaactggagcacact cc tcctatgagctgacacagctg | 125 |
| ERR1- TOP54 LC-F | Same as ERR1-TOP43 LC-F | 126 |
| ERR1-324 KC-F | tttctcgtagctgctgcaactggagcacact cc gagctcgtgctgacccagact | 127 |
| LC-R- XhoI | ggcctcgagttatgaacattctgtaggggc | 128 |
| KC-R- XhoI. | ggcctcgagttaacactctcccctgttgaa | 129 |

Example 4. Examination of Antibody Binding Activities

Figure 4:
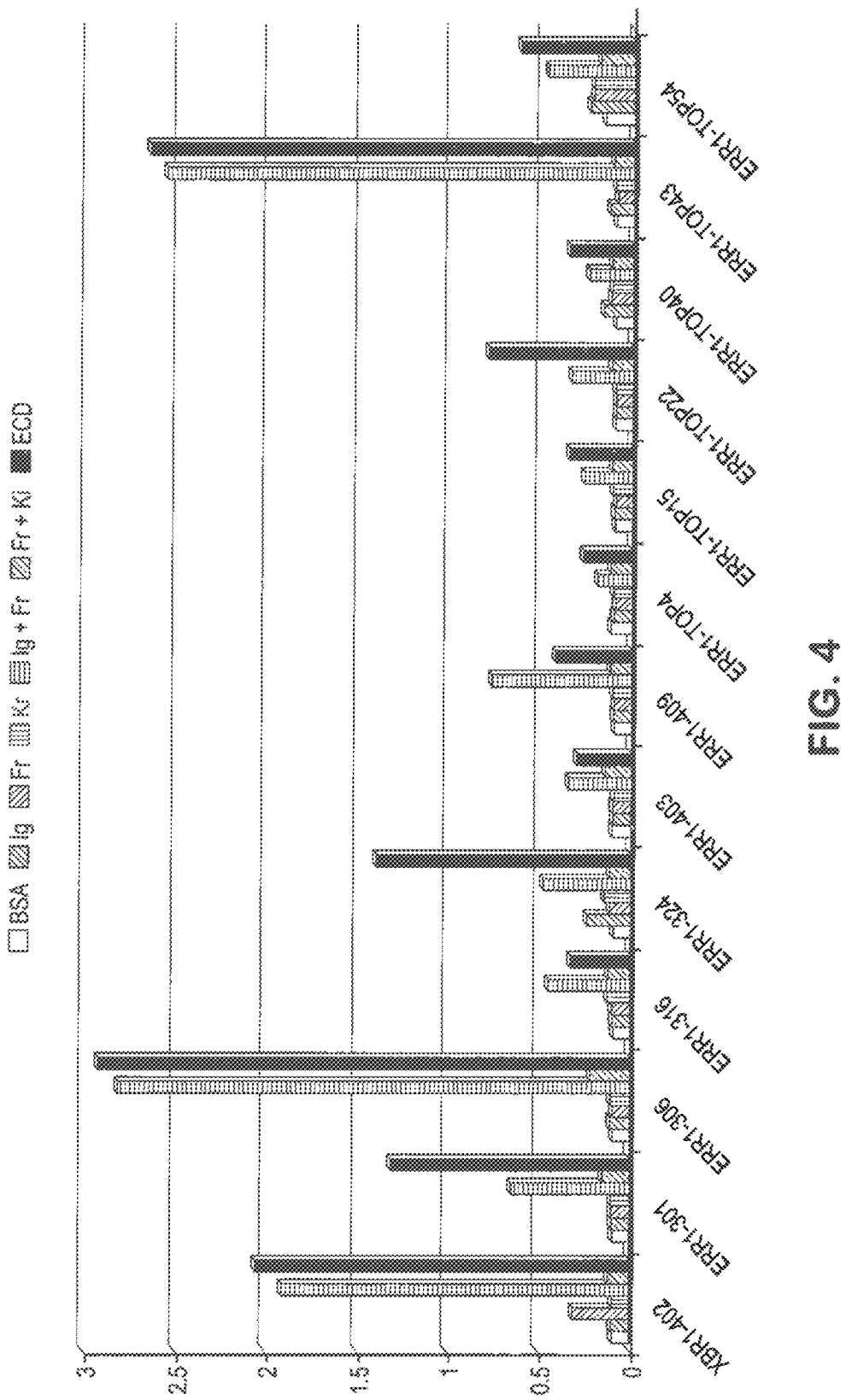
FIG. 4 shows epitope mapping studies for chimeric rabbit/human Fabs on six different immobilized IgG1-Fc fusion proteins that comprise different parts of the extracellular domain of human ROR1: hFc-hROR1-Ig (comprising the Immunoglobulin-domain of hROR1), hFc-hROR1-Fr (comprising the Frizzled domain of hROR1), hFc-hROR1-Kr (comprising the Kringle domain of hROR1), hFc-hROR1-Ig-Fr (comprising the Immunoglobulin and Frizzled domains of hROR1), hFc-hROR1-Fr-Ki (comprising the Frizzled and Kringle domains of hROR1) and hFc-hROR1 (comprising the entire extracellular domain (ECD) of hROR1).

ELISA:

For ELISA (FIG. 2), each well of a 96-well Costar 3690 plate (Corning, Corning, N.Y.) was coated with 100 ng anti-human IgG1 Fc in 25 µL coating buffer (0.1 M $Na_2CO_3$, 0.1 M $NaHCO_3$, pH 9.6) for 1 h at 37° C. After blocking with 150 µL 3% (w/v) BSA/TBS for 1 h at 37° C., hFc-hROR1 or hFc-mROR1 was captured following incubation at 100 ng/50 µL for 1 h at 37° C. Then 100 ng/50 µL of Fab was applied in each well at 37° C. 2 h later, 50 µL of a 1:1000 dilution of a mouse anti-His tag mAb conjugated to horse radish peroxidase (HRP) (R&D Systems, Minneapolis, Minn.) in 1% (w/v) BSA/TBS was used to detect the Fab. To determine the epitopes (FIG. 4), hFc fusion proteins containing different domains of hROR1 were coated directly, followed by incubation with Fab before detection by mouse anti-His tag mAb conjugated to HRP. Washing with PBS was repeated and colorimetric detection was performed using 2,2'-azino-bis (3-ethylbenzthiazoline)-6-sulfonic acid (Roche) as substrate according to the manufacturer's directions. The absorbance was measured at 405 nm using a SpectraMax M5 microplate reader (Molecular Devices; Sunnyvale, Calif.) and SoftMax Pro software (Molecular Devices).

Flow Cytometry:

Cells were stained using standard flow cytometry methodology. Briefly, for purified anti-ROR1 Fab (FIG. 3), 0.1-1×10⁶ cells were stained with 1000 ng/100 µL of Fab on ice for 1 h. After washing twice with ice-cold flow cytometry buffer (PBS containing 1% (v/v) BSA, 0.1% sodium azide and 1 mM EDTA), the cells were incubated with a 1:1000 dilution of a mouse anti-His tag mAb conjugated to Alexa Fluor 488 (Qiagen) in 100 µL flow cytometry buffer on ice for 30 min. For purified anti-ROR1 IgG1 (FIG. 8), 0.1~1×10⁶ cells were blocked by 4% goat serum for 15 min at room temperature and then incubated with 100 ng/100 µL of IgG on ice for 1 h. After washing twice with ice-cold flow cytometry buffer, cells were stained with a 1:500 dilution of goat anti-human IgG, Fcγ pAbs conjugated to APC (Jackson ImmunoResearch) in 100 µL flow cytometry buffer on ice for 30 min. For commercial goat anti human ROR1 polyclonal antibody (FIG. 8), 0.1~1×10⁶ cells were stained with 200 ng/100 µL of Ab on ice for 1 h. After washing twice with ice-cold flow cytometry buffer (PBS containing 1% (v/v) BSA, 0.1% sodium azide and 1 mM EDTA), the cells were incubated with a 1:1000 dilution of a Alexa Fluor 647-conjugated AffiniPure F(ab')₂ donkey anti goat IgG (H+L) in 100 µL flow cytometry buffer on ice for 30 min. Finally, 4',6-diamidino-2-phenylindole (DAPI) was added to a final concentration of 100 ng/mL to exclude dead cells from the analysis. Cells were analyzed using a FACSCalibur instrument (BD Biosciences) and FlowJo analytical software (Tree Star, Ashland, Oreg.).

Figure 5:
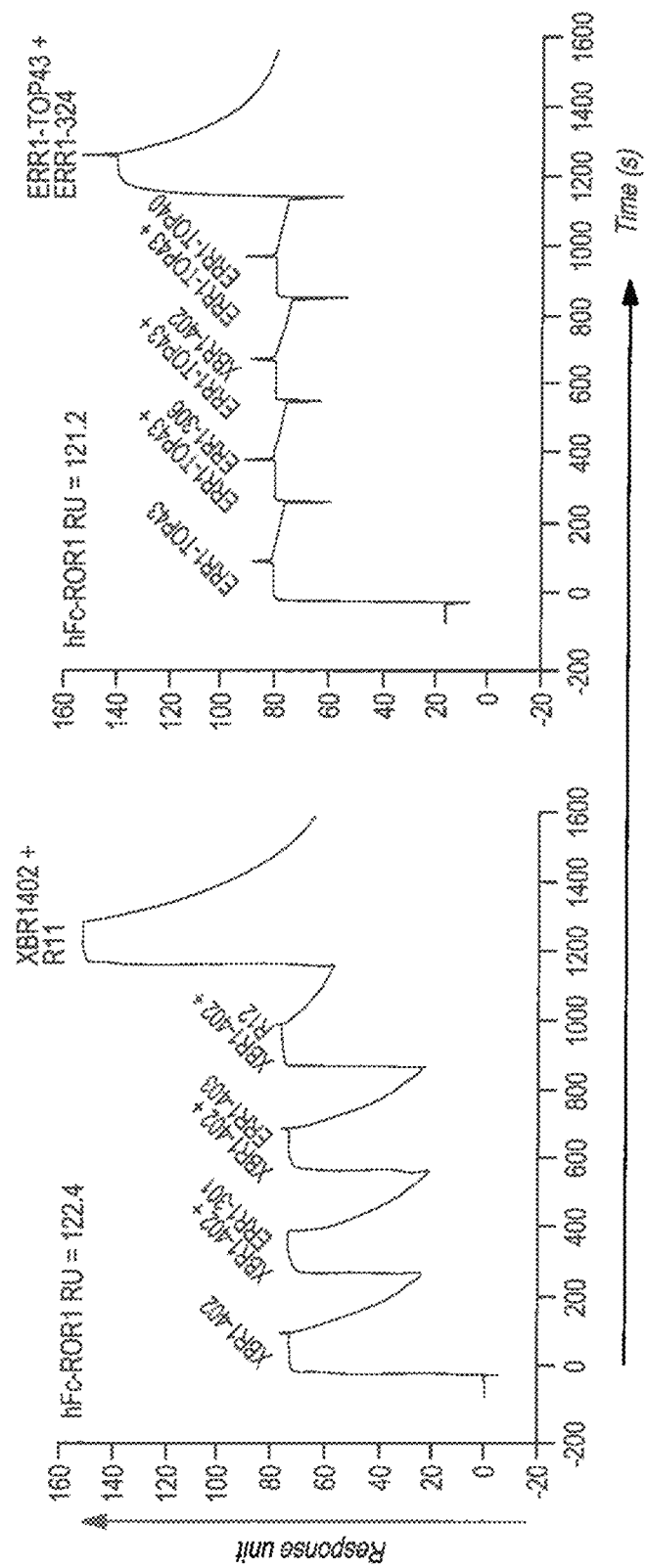
FIG. 5 shows epitope binding studies performed by surface plasmon resonance. Shown are SPR sensograms obtained for the binding of different Fabs to hFc-hROR1 captured by anti-human Fcγ antibody immobilized on a CM5 chip. Fabs were injected in different orders to identify independent and overlapping epitopes. Resonance unit (RU, y axis) increases that exceeded the values found for previously injected Fabs indicated independent epitopes because they allow simultaneous binding. For example, the increase found for the binding of Fab R11 exceeded the values found for XBR1-402 alone, indicating that Fab R11 and XBR1-402 can bind simultaneously to human ROR1. By contrast, the epitope of Fab XBR1-402 overlaps with the epitopes of ERR1-301, ERR1-403 and R12 (left graph); the epitope of Fab ERR1-TOP43 overlaps with the epitope of ERR1-306, XBR1-402 and ERR1-TOP40. The x axis depicts the time in seconds (s).

Surface Plasmon Resonance:

Surface plasmon resonance for the measurement of the affinities of all Fabs to hFc-hROR1 and for epitope mapping studies were performed on a Biacore ×100 instrument using Biacore reagents and software (GE Healthcare, Piscataway, N.J.). Anti-Human IgG (Fc) antibody was immobilized on a CM5 sensor chip following the instruction of Human Antibody Capture Kit (GE Healthcare, Piscataway, N.J.). Then, hFc-hROR1 fusion proteins were captured at certain density (indicated in FIG. 5 and FIG. 6). The sensor chip included an empty flow cell for instantaneous background depletion. All binding assays used 1×HBS-EP+ running buffer (10 mM HEPES, 150 mM NaCl, 3 mM EDTA (pH 7.4), and 0.05% (v/v) Surfactant P20) and a flow rate of 30 mL/min. For affinity measurements, all Fabs were injected at five different concentrations (dilution factor was 2), and the lowest concentration was tested in duplicates (the highest concentrations for each Fab are indicated in FIG. 6B). The sensor chip was regenerated with 3 $MgCl_2$ from the Human Antibody Capture Kit without any loss of binding capacity. Calculation of association ($k_{on}$) and dissociation ($k_{off}$) rate constants was based on a 1:1 Langmuir binding model. The equilibrium dissociation constant ($K_d$) was calculated from $k_{off}/k_{on}$. For epitope mapping studies, each Fab was prepared at 500 nM alone in 1×HBS-EP+ running buffer and then injected in order as indicated in FIG. 5.

Figure 9:
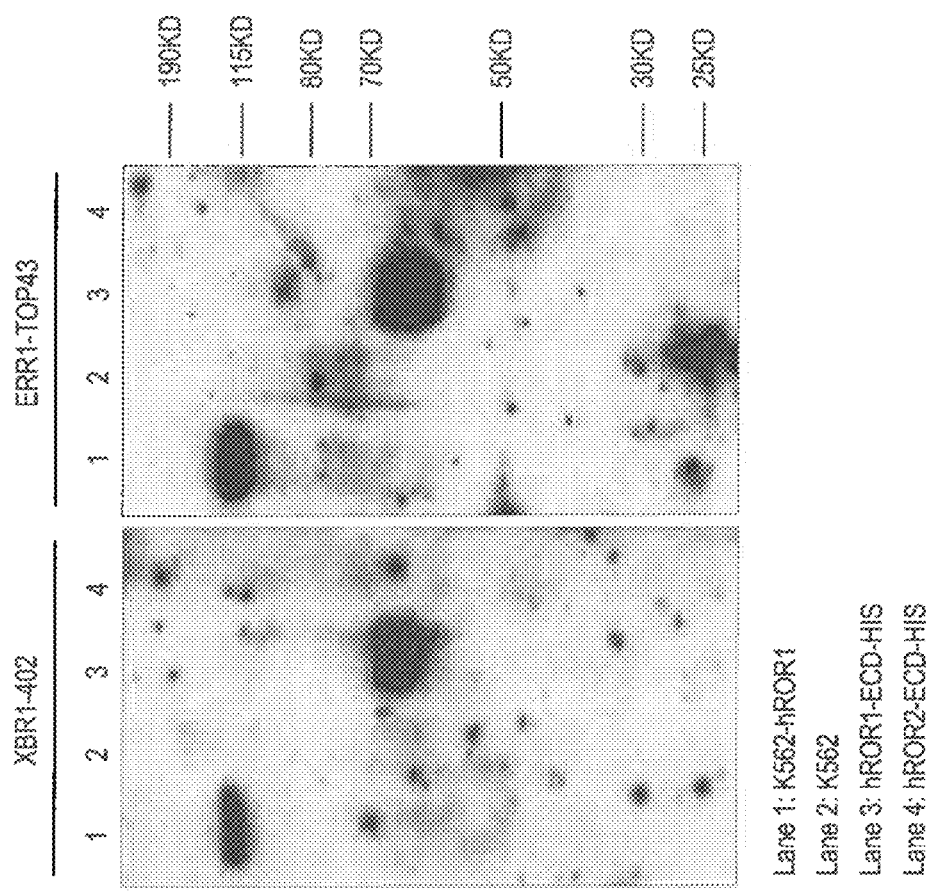
FIG. 9 shows the binding activity of chimeric rabbit/human IgG1 XBR1-402 and ERR1-TOP43 (both hROR1 specific) to denatured hROR1 in Western-blot experiments. hROR1 expressed on the cell surface K562 cells or purified protein was denatured and detected by Western blotting. The Western blots contained the following samples as indicated: Lane 1: K562 cells ectopically expressing full length of hROR1. Lane 2: untransfected K62 cells. Lane 3: purified extracellular domain of hROR1. Lane 4: purified extracellular domain of hROR2.

Western Blotting:

Cells or proteins were lysed by 1× sample buffer (containing 1% β-mercaptoethanol) and boiled before running on NuPAGE Novex 4-12% Bis-Tris gels (Invitrogen). After membrane transferring and blocking by 5% milk, 2 µg/mL chimeric rabbit/human IgG1 of XBR1-402 or ERR1-TOP43 was applied to detect the denatured proteins, followed by incubation with 1/1000 anti-human Fcγ conjugated to HRP before developing using ECL Prime Western Blotting Detection Reagent (GE Healthcare) (FIG. 9).

Example 5 Expression of Purified, Recombinant Strep-Tagged Human ROR1 and Human Twin Strep-Tagged Human ROR2

StrepII-tagged human ROR1-extracellular domain was produced as follows: the nucleotide sequence encoding the extracellular domain of human ROR1 (NP_005003.2) was N-terminally fused to a signal sequence (MNFGLRLIFLVLTLKGVQC) (SEQ ID NO:162) and C-terminally fused with a sequence encoding a strepII-tag (GWSHPQFEK) (SEQ ID NO:163). The entire nucleotide sequences with flanking 5'NotI and 3'HindIII sites were produced by total gene synthesis (GenScript, Piscataway, USA), assembled in the proprietary mammalian expression vector pEvi5 by Evitria AG (Schlieren, Switzerland) and verified by DNA sequencing.

Expression of the proteins was performed in suspension-adapted CHO K1 cells by Evitria AG (Schlieren, Switzerland). Supernatants from pools of transfected CHO K1 cells were harvested by centrifugation and sterile filtered (0.2 µm) before FPLC-based affinity purification using StrepTactin columns (IBA GmbH, Goettingen, Germany).

Recombinant human twin strep-tagged ROR2 (NP_004551.2) was expressed and purified in-house according to the following protocol: the EBNA expression vector pCB14b-ROR2-ECD-TwinStrep, directing expression of ROR2 extracellular domain (ECD), C-terminally tagged with a TwinStep tag, was transfected into HEK293T using Lipofectamine® LTX with PLUS™ Reagent (Thermo Fisher Scientific, 15388100). Following a 1-day incubation (37° C., 5% $CO_2$, growth media: Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept)), cells were expanded under selection conditions (2 µg/mL of puromycin (Sigma-Aldrich, P8833-25 mg stock at 2 mg/mL)). Cells were split and further expanded (37° C., 5% $CO_2$); once confluency was reached, tissue culture dishes were coated with 20 µg/ml poly-L-Lysine (Sigma-Aldrich, P1524) for 2 hrs at 37° C. and washed twice with PBS. Then, cells were trypsinized, washed with PBS and split 1:3 onto poly-L-lysine-coated plates. Again after reaching confluency, cells were washed with PBS followed by with media replacement using production media (DMEM/F-12, Gibco/Thermo Fisher Scientific, 31330-03) supplemented with 1 µg/mL puromycin (Sigma-Aldrich, P8833), 100 IU/mL of Pen-Strep-Fungizone (Bioconcept, 4-02F00-H), 161 µg/mL of N-acetyl-L-cysteine (Sigma-Aldrich, A8199) and 10 µg/mL of L-glutathione reduced (Sigma-Aldrich, G6529). Supernatant, harvested bi-weekly and filtered (0.22 µm) to remove cells, was stored at 4° C. until purification. For purification, filtered supernatant was loaded onto a Streptactin® Superflow® high capacity cartridge (IBA, Gottingen, Germany, 2-1238-001) column; purification and elution was performed according to the manufacturer's protocol on an AEKTA pure (GE Healthcare). Fractions were analyzed for protein purity and integrity by SDS-PAGE. Protein-containing fractions were mixed and subjected to buffer exchange using Amicon filtration units (Millipore, Schaffhausen, Switzerland) to reach a dilution of ≥1:100 in PBS, and then sterile filtered using a low retention filter (0.20 µm, Carl Roth, Karlsruhe, Germany, Pa. 49.1).

Example 6. Expression of Purified, Recombinant Humanized Anti-Human ROR1 and Isotype Control Antibodies Expression Vectors:

Antibody variable region coding regions were produced by total gene synthesis (GenScript) using MNFGLRLIFLVLTLKGVQC (SEQ ID NO:162) as leader sequence, and were assembled with human IgH-γ 1 and IgL-κ or IgL-λ constant regions, as applicable, in the expression vector pCB14. This vector, a derivative of the episomal mammalian expression vector pCEP4 (Invitrogen), carries the EBV replication origin, encodes the EBV nuclear antigen (EBNA-1) to permit extrachromosomal replication, and contains a puromycin selection marker in place of the original hygromycin B resistance gene.

In-House Expression and Purification:

pCB14-based expression vectors were transfected into HEK293T cells using Lipofectamine® LTX Reagent with PLUS™ Reagent (Thermo Fisher Scientific, Reinach, Switzerland, 15388100); following a 1-day incubation (37° C., 5% $CO_2$, growth media: Dulbecco's Modified Eagle Medium (DMEM) High Glucose (4.5 g/l) with L-Glutamine with 10% (v/v) Fetal Calf Serum (FCS), 100 IU/mL of Pen-Strep-Fungizone and 2 mM L-glutamine (all Bioconcept, Allschwil, Switzerland)), cells were expanded under selection conditions (2 µg/mL of puromycin (Sigma-Aldrich, Buchs SG, Switzerland, P8833-25 mg stock at 2 mg/mL)). Cells were split and further expanded (37° C., 5% $CO_2$); once confluency was reached, tissue culture dishes were coated with 20 µg/ml poly-L-Lysine (Sigma-Aldrich, P1524) for 2 h at 37° C. and washed twice with PBS. Then, cells were trypsinized and split 1:3 onto poly-L-lysine-coated plates. Again after reaching confluency, cells were washed with PBS followed by media replacement to production media (DMEM/F-12, Gibco/Thermo Fisher Scientific, 31330-03) supplemented with 1 µg/mL puromycin (Sigma, P8833), 100 IU/mL of Pen-Strep-Fungizone (Bioconcept), 161 µg/mL of N-acetyl-L-cysteine (Sigma-Aldrich, A8199) and 10 µg/mL of L-glutathione reduced (Sigma-Aldrich, G6529). Supernatant, harvested bi-weekly and filtered (0.22 µm) to remove cells, was stored at 4° C. until purification.

For purification, filtered supernatant was loaded onto a PBS-equilibrated Protein A HiTrap column (GE Healthcare, Frankfurt am Main, Germany, 17-0405-01) or a JSR Amsphere™ Protein A column (JSR Life Sciences, Leuven, Belgium, JWT203CE) and washed with PBS; elution was performed using 0.1 M glycine (pH 2.5) on an AEKTA pure (GE Healthcare). Fractions were immediately neutralized with 1 M Tris-HCl buffer (pH 8.0), and analyzed for protein purity and integrity by SDS-PAGE. Protein-containing fractions were mixed and subjected to buffer exchange using Amicon filtration units (Millipore, Schaffhausen, Switzerland, UFC901008) to reach a dilution of 1:100 in the buffer listed in Table 2, and then sterile filtered using a low retention filter (0.20 µm, Carl Roth, Karlsruhe, Germany, Pa.49.1).

Antibodies were transiently expressed in CHO cells by methods known in the art and recombinant antibodies were purified by standard protein A purification from CHO cell supernatants, as known in the art. The purity and the integrity of the recombinant antibodies were analyzed by SDS-PAGE.

Table 2 lists the antibodies used in subsequent examples, along with their final concentration and buffer.

TABLE 2

List of antibodies used in the Examples

| Antibody (ref.) | Format | Antibody SEQ ID HC/LC | C-Terminal Tags (HC: Heavy Chain, LC: Light Chain) | Buffer | Final conc. (mg/mL) |
|---|---|---|---|---|---|
| XBR1-402 (mAb031) | IgG | HC: SEQ ID NO. 1 LC: SEQ ID NO. 14 | HC: LPETG-Strep LC: G5SLPETG-Strep | PBS | 3.9 |
| ERR1-301 (mAb027) | IgG | HC: SEQ ID NO. 2 LC: SEQ ID NO. 15 | HC: LPETG-Strep LC: G5SLPETG-Strep | PBS | 3.8 |
| ERR1-306 (mAb033) | IgG | HC: SEQ ID NO. 3 LC: SEQ ID NO. 16 | HC: LPETG-Strep LC: G5SLPETG-Strep | PBS | 3.0 |
| ERR1-324 (mAb034) | IgG | HC: SEQ ID NO. 5 LC: SEQ ID NO. 18 | HC: LPETG-Strep LC: G5SLPETG-Strep | PBS | 3.0 |
| ERR1-403 (mAb035) | IgG | HC: SEQ ID NO. 6 LC: SEQ ID NO. 19 | HC: LPETG-Strep LC: G5SLPETG-Strep | PBS | 2.9 |
| ERR1-Top43 (mAb036) | IgG | HC: SEQ ID NO. 12 LC: SEQ ID NO. 25 | HC: LPETG-Strep LC: G5SLPETG-Strep | PBS | 3.0 |

TABLE 2-continued

List of antibodies used in the Examples

| Antibody (ref.) | Format | Antibody SEQ ID HC/LC | C-Terminal Tags (HC: Heavy Chain, LC: Light Chain) | Buffer | Final conc. (mg/mL) |
|---|---|---|---|---|---|
| XBR1-402 (mAb186) | IgG | HC: SEQ ID NO. 1 LC: SEQ ID NO. 14 | HC: LPETG-Strep LC: G5SLPETG-Strep | PBS | 3.9 |
| ERR1-324 (mAb188) | IgG | HC: SEQ ID NO. 5 LC: SEQ ID NO. 18 | HC: LPETG-Strep LC: G5SLPETG-Strep | PBS | 7.1 |
| ERR1-Top43 (mAb189) | IgG | HC: SEQ ID NO. 12 LC: SEQ ID NO. 25 | HC: LPETG-Strep LC: G5SLPETG-Strep | PBS | 7.0 |
| XBR1-402 (mAb202) | IgG | HC: SEQ ID NO. 1 LC: SEQ ID NO. 14 | HC: LPETG-Strep LC: G5SLPETG-Strep | PBS | 6.3 |
| Ms961 (mAb190) | IgG | HC: SEQ ID NO. 148 LC: SEQ ID NO. 149 | HC: LPETG-Strep LC: G5SLPETG-Strep | PBS | 6.4 |
| 2A2 (mAb066) | IgG | HC: SEQ ID NO. 150 LC: SEQ ID NO. 151 | HC: LPETG-Strep LC: G5SLPETG-Strep | PBS | 8.0 |
| hu2A2 (mAb038) | IgG | HC: SEQ ID NO. 152 LC: SEQ ID NO. 153 | HC: LPETG-Strep LC: G5SLPETG-Strep | PBS | 4.7 |
| R11 (mAb062) | IgG | HC: SEQ ID NO. 154 LC: SEQ ID NO. 155 | HC: LPETG-Strep LC: G5SLPETG-Strep | PBS | 6.6 |
| R12 (mAb067) | IgG | HC: SEQ ID NO. 156 LC: SEQ ID NO. 157 | HC: LPETG-Strep LC: G5SLPETG-Strep | PBS | 5.7 |
| Trastuzumab ("Tras" mAb042) | IgG | HC: SEQ ID NO. 158 LC: SEQ ID NO. 159 | HC: LPETG-Strep LC: G5SLPETG-Strep | PBS | 2.7 |
| Ac10 (mAb046) | IgG | HC: SEQ ID NO. 160 LC: SEQ ID NO. 161 | HC: LPETG-Strep LC: G5SLPETG-Strep | PBS | 7.9 |

Ms961 corresponds to an anti-ROR1 antibody with a heavy chain according to SEQ ID NO. 1 and light chain according to SEQ ID NO. 3 of WO 2014/031174. 2A2 refers to an anti-ROR1 antibody as described in WO 2010/124188, while hu2A2 refers to a humanized 2A2 as described in unpublished PCT/EP2016/076244. R11 and R12 are anti-ROR1 antibodies described in WO 2012/075158. Isotype control antibodies trastuzumab and Ac10 target HER-2 and CD30, respectively. The heavy and light chain variable region sequences of monoclonal antibody brentuximab (clone cAc10) specific for the human CD30 target were obtained from patent US2008213289A1, those of the human HER-2 specific trastuzumab antibody contained in the commercial antibody Herceptin (trastuzumab), or the ADC Kadcyla® derived thereof, were derived from the online IMGT database.

Example 7. mAb ROR1 and ROR2-Binding—Characterization by ELISA

Each well of a 96-well plate was coated with 100 µL of 2 µg/mL strep-tagged human ROR1 (from Example 5) in 0.1 M bicarbonate coating buffer (pH 9.6), and incubated for 12 h at 4° C. A second 96-well plate was likewise prepared with twin-strep tagged human ROR2 (from Example 5).

After blocking with 150 µL of 3% (w/v) bovine serum albumin (BSA)/TBS for 1 h at 37° C., the following antibodies were added to a well within each plate at a concentration of 0.5 µg/mL, and serially diluted (dilution factor 4) with 1% (w/v) BSA/TBS, before incubation for 1 h at 37° C.: ERR1-301 (mAb027), XBR1-402 (mAb031), ERR1-306 (mAb033), ERR1-324 (mAb034), ERR1-403 (mAb035) and ERR1-Top43 (mAb036). HRP-conjugated F(ab')2 anti-human FC-gamma (Jackson Immunoresearch, 109-036-008) was then added at a 1:20'000 dilution, 100 µL per well, and incubated for 1 h at 37° C. prior to detection using an Spark 10M plate reader (Tecan). As shown in FIG. 10, the anti-human ROR1 antibodies bind human ROR1 (panel A) and are not cross-reactive with human ROR2 (panel B).

Example 8. Humanization of Anti-hROR1-Specific Antibody XBR1-402

Humanized variable region sequences (seven hu4-2 VH variants and 4 hu4-2 VL variants) were designed by Fusion Antibodies (Belfast, Ireland). Briefly, frameworks in rabbit variable regions were exchanged with human framework regions (following an in-silico assisted CDR-grafting approach based on proprietary algorithms) to form 28 possible heavy chain/light chain pairs.

Expression of antibodies representing all 28 possible heavy chain/light chain pairs was achieved by transiently transfecting pCB14-based expression constructs into HEK-293T cells and harvesting cell supernatants.

For transient antibody expression, cells were transfected in 24-well-plates using Avanti Transfection Reagent I (Avanti Polar Lipids, Alabaster, USA). Per well, 0.5 µg of total DNA was transfected, and fresh growth medium was added the next day and conditioned for 4 days. Supernatants were sterile-filtered and stored at −20° C. until analysis.

Affinity screening was then performed to select the best binders. Affinities were determined using a Biacore T200 instrument (GE Healthcare, Buckinghamshire, UK) and data was evaluated using Biacore Evaluation T200 V2.0 software. To capture mAbs, goat α-human Fc-gamma-specific IgG (Jackson ImmunoResearch, #109-005-098) was covalently immobilized on a CM5 chip (GE Healthcare, #BR-1005-30).

Briefly, for capturing mAbs in HEK293T supernatants, the undiluted supernatants were captured with a flow of 30 µl/min for 120 s. ROR1-strep was diluted in running buffer (HBS-EP+pH 7.4 (10 mM HEPES, 150 mM NaCl, 3 mM EDTA, 0.05% Tween 20) to 20 nM. Association was measured at a flow of 30 µl/min for 120 s, and dissociation was followed for 200 s at a flow of 30 µl/min. Capture levels ranged from 31.8 RU to 59.4 RU.

Selected antibodies were expressed and purified as per Example 6, subject to the conditions of Table 3 below.

Example 10. Generation of Site-Specifically Conjugated ADCs Using SMAC-Technology Sortase a Enzyme.

Recombinant and affinity purified Sortase A enzyme from *Staphylococcus aureus* was produced in *E. coli* as disclosed in WO2014140317A1.

Generation of Glycine-Modified Toxins.

In order to generate SMAC-Technology™ conjugated ADCs with pentaglycine-modified PNU-159682 derivative Gly$_5$-EDA-PNU (FIG. 11B) was manufactured as disclosed in WO2016102697. The identity and the purity of the pentaglycine-modified PNU toxin was confirmed by mass-spectrometry and HPLC. The Gly$_5$-modified toxin exhibited >95% purity, as determined by the single peak in the HPLC chromatogram.

TABLE 3

Protocols and concentrations of humanized mAbs used in the Examples

| Antibody (ref.) | Format | Antibody SEQ ID HC/LC | C-Terminal Tags (HC: Heavy Chain, LC: Light Chain) | Buffer | Final conc. (µg/mL) | KD (nM) |
|---|---|---|---|---|---|---|
| HuXBR1-402(3) (mAb288) | IgG | HC: SEQ ID NO. 130<br>LC: SEQ ID NO. 136 | HC: LPETG-TwinStrep<br>LC: G$_5$SLPETG-TwinStrep | PBS | 0.49 | 3.16 |
| HuXBR1-402(8) (mAb289) | IgG | HC: SEQ ID NO. 131<br>LC: SEQ ID NO. 137 | HC: LPETG-TwinStrep<br>LC: G$_5$SLPETG-TwinStrep | PBS | 0.48 | 2.14 |
| HuXBR1-402(15) (mAb290) | IgG | HC: SEQ ID NO. 132<br>LC: SEQ ID NO. 138 | HC: LPETG-TwinStrep<br>LC: G$_5$SLPETG-TwinStrep | PBS | 0.45 | 3.55 |
| HuXBR1-402(17) (mAb291) | IgG | HC: SEQ ID NO. 133<br>LC: SEQ ID NO. 139 | HC: LPETG-TwinStrep<br>LC: G$_5$SLPETG-TwinStrep | PBS | 0.63 | 3.34 |
| HuXBR1-402(19) (mAb295) | IgG | HC: SEQ ID NO. 134<br>LC: SEQ ID NO. 140 | HC: LPETG-TwinStrep<br>LC: G$_5$SLPETG-TwinStrep | PBS | 0.50 | 2.98 |
| HuXBR1-402(26) (mAb296) | IgG | HC: SEQ ID NO. 135<br>LC: SEQ ID NO. 141 | HC: LPETG-TwinStrep<br>LC: G$_5$SLPETG-TwinStrep | PBS | 0.49 | 3.13 |

Example 9. FACS Staining of Cells for hROR1 Expression $5 \times 10^5$ of each cell type were added per well to 96-well plates. Plates were centrifuged (3 min, 1300 rpm) with re-suspension in buffer (PBS supplemented with 2% (v/v) of FCS). 2A2 (mAb066) was added to each well to reach a concentration of 2 µg/mL. Plates were then incubated on ice for 30 min and washed with 200 µL of buffer prior to resuspension in 200 µL of buffer supplemented with anti-human IgG antibody (Fc gamma-specific) PE (eBioscience 12-4998-82) at a 1:250 dilution. Following 30 min incubation on ice and one washing, cells were analyzed using a FACSCalibur instrument (BD Biosciences) and data was analyzed using FlowJo analytical software (Tree Star, Ashland, Oreg.).

Figure 7:
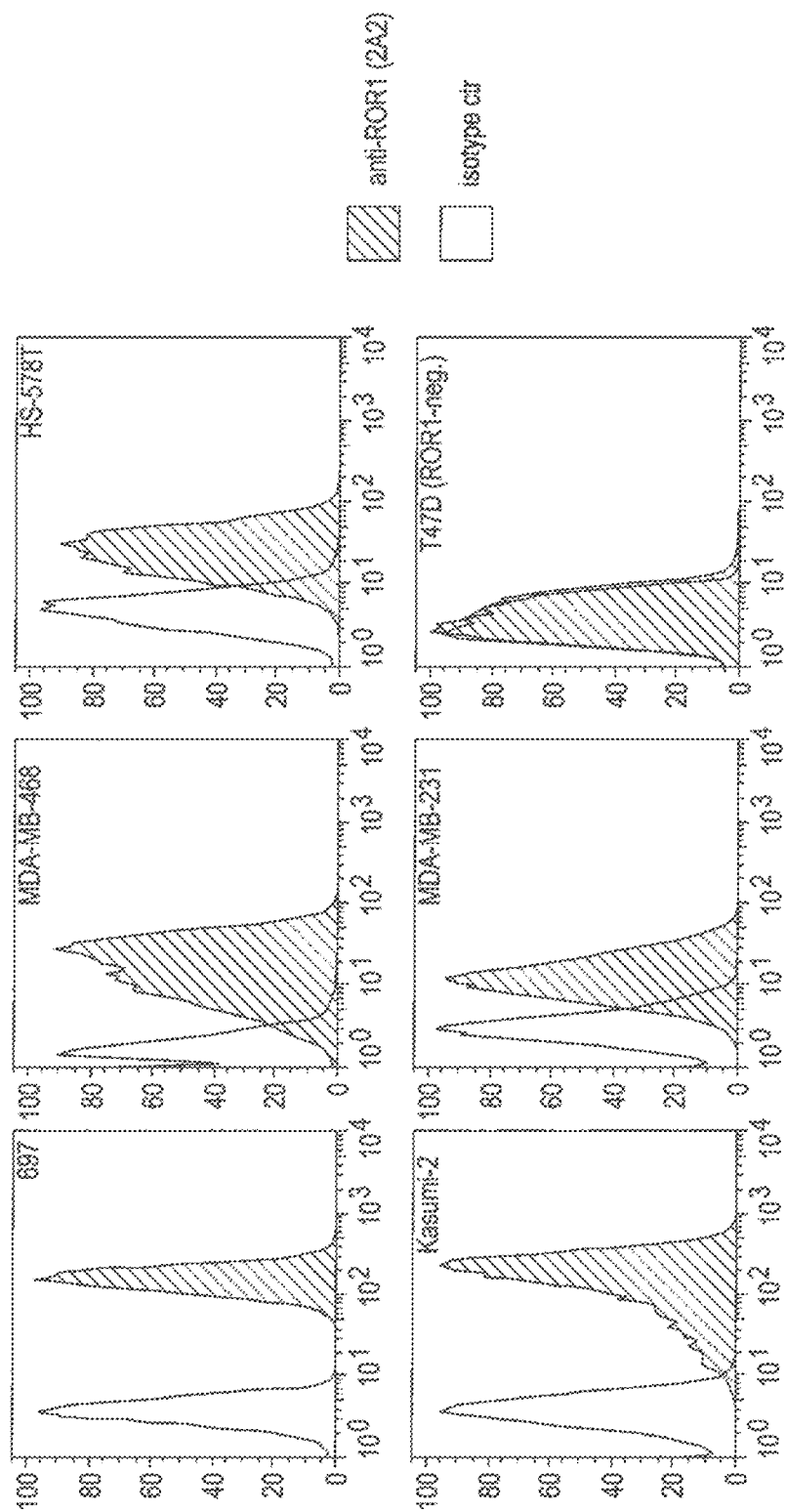
FIG. 7 shows FACS-based cell staining of hROR1 on various human cancer cell lines with anti-human ROR1 antibody 2A2 as described in Example 9. Cell lines analyzed lines include 697 (human acute lymphocytic leukemia, ALL), Kasumi-2 (human preB acute lymphocytic leukemia), human triple-negative breast cancer cell lines MDA-MB-231, MDA-MB-468 and HS-578T, as well as human breast cancer cell line T47D. Except for the T47D human breast cancer cell line, all of the evaluated cells are positive for hROR1 expression.

FIG. 7 shows the FACS analysis data of ROR1-positive human ALL cell lines 697 and Kasumi-2, human triple-negative breast cancer cell lines MDA-MB-231, MDA-MB-468 and HS-578T, and ROR1-negative human breast cancer cell line T47D as a negative control.

Sortase-Mediated Antibody Conjugation.

The above-mentioned toxin was conjugated to anti-ROR1 antibodies as per Table 3 by incubating LPETG-tagged mAbs [10 µM] with glycine modified toxin [200 µM] and 3 µM Sortase A in the listed conjugation buffer for 3.5 h at 25° C. The reaction was stopped by passing it through an rProtein A GraviTrap column (BioRad). Bound conjugate was eluted with 5 column volumes of elution buffer (0.1 M glycine pH 2.5, 50 nM NaCl), with 1 column volume fractions collected into tubes containing 25% v/v 1M HEPES pH 8 to neutralize the acid. Protein containing fractions were pooled and formulated in the formulation buffer of Table 7 using a ZebaSpin desalting column.

Adc Analytics.

DAR was assessed by Reverse Phase Chromatography performed on a Polymer Labs PLRP 2.1 mm×5 cm, 5 µm column run at 1 mL/min/80° C. with a 25 minute linear gradient between 0.05 to 0.1% TFA/H$_2$O and 0.04 to 0.1% TFA/CH$_3$CN. Samples were first reduced by incubation with DTT at pH 8.0 at 37° C. for 15 minutes. The DAR determined by Reverse Phase Chromatography is summarized in Table 4 below.

TABLE 4

Manufacturing conditions and analytical summary of ADCs manufactured in this study. DAR, drug-to-antibody ratio.

| ADC (ref.) | mAb (ref.) | Toxin | Conjugation Buffer | Formulation Buffer | DAR |
|---|---|---|---|---|---|
| XBR1-402-G5-PNU (Adc135) | XBR1-402 (mAb031) | G5-PNU | 50 mM HEPES (pH 7.5), 150 mM NaCl, 5 mM $CaCl_2$ | PBS without $Ca^{2+}$ and $Mg^{2+}$ (Amimed-Bioconcept) | ND |
| ERR1-301-G5-PNU (Adc200) | ERR1-301 (mAb027) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.7 |
| ERR1-306-G5-PNU (Adc201) | ERR1-306 (mAb033) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.7 |
| ERR1-324-G5-PNU (Adc202) | ERR1-324 (mAb034) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.6 |
| ERR1-403-G5-PNU (Adc203) | ERR1-403 (mAb035) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.7 |
| ERR1-Top43-G5-PNU (Adc204) | ERR1-Top43 (mAb036) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.6 |
| XBR1-402-G5-PNU (Adc262) | XBR1-402 (mAb186) | G5-PNU | 50 mM HEPES (pH 7.5), 150 mM NaCl, 5 mM $CaCl_2$ | PBS without $Ca^{2+}$ and $Mg^{2+}$ (Amimed-Bioconcept) | 3.7 |
| XBR1-402-G5-PNU (Adc288) | XBR1-402 (mAb186) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.7 |
| XBR1-402-G5-PNU (Adc394) | XBR1-402 (mAb202) | G5-PNU | 50 mM HEPES (pH 7.5), 10% (v/v) glycerol, 1 mM $CaCl_2$ | PBS without $Ca^{2+}$ and $Mg^{2+}$ (Amimed-Bioconcept) | 3.9 |
| ERR1-324-G5-PNU (Adc395) | ERR1-324 (mAb188) | G5-PNU | 50 mM HEPES (pH 7.5), 10% (v/v) glycerol, 1 mM $CaCl_2$ | PBS without $Ca^{2+}$ and $Mg^{2+}$ (Amimed-Bioconcept) | 3.8 |
| XBR1-402-G5-PNU (Adc409) | XBR1-402 (mAb202) | G5-PNU | 50 mM HEPES (pH 7.5), 10% (v/v) glycerol, 1 mM $CaCl_2$ | PBS without $Ca^{2+}$ and $Mg^{2+}$ (Amimed-Bioconcept) | ND |
| 2A2-G5-PNU (adc165) | 2A2 (mAb066) | G5-PNU | 50 mM HEPES (pH 7.5), 150 mM NaCl, 1 mM $CaCl_2$ | HEPES buffer saline pH 6.8 | 3.8 |
| hu2A2-G5-PNU (adc287) | hu2A2 (mAb038) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.7 |
| R11-G5-PNU (adc041) | R11 (mAb062) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | ND |
| R12-G5-PNU (adc263) | R12 (mAb067) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.6 |
| R12-G5-PNU (adc292) | R12 (mAb067) | G5-PNU | 25 mM HEPES (pH 7.5), 150 mM NaCl, 1 mM $CaCl_2$, 10% (v/v) glycerol | 10 mM Succinate pH 5.0, 175 mM Sucrose, 0.02% Tween 20 | 3.8 |
| R12-G5-PNU (adc327) | R12 (mAb067) | G5-PNU | 25 mM HEPES (pH 7.5), 150 mM NaCl, 1 mM $CaCl_2$, 10% (v/v) glycerol | 10 mM Succinate pH 5.0, 175 mM Sucrose, 0.02% Tween 20 | 3.8 |
| Ms961-G5-PNU (adc396) | Ms961 (mAb190) | G5-PNU | 50 mM HEPES (pH 7.5), 1 mM $CaCl_2$, 10% (v/v) glycerol | 10 mM Succinate pH 5.0, 175 mM Sucrose, 0.02% Tween 20 | ND |
| Tras-G5-PNU (adc196) | Trastuzumab (mAb042) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.6 |
| Tras-G5-PNU (adc286) | Trastuzumab (mAb042) | G5-PNU | 50 mM HEPES (pH 7.5), 150 mM NaCl, 1 mM $CaCl_2$ | 25 mM HEPES pH6.8, 15 mM NaCl | 3.7 |
| Ac10-G5-PNU (adc159) | Ac10 (mAb046) | G5-PNU | 50 mM HEPES (pH 7.5), 150 mM NaCl, 1 mM $CaCl_2$ | PBS without $Ca^{2+}$ and $Mg^{2+}$ (Amimed-Bioconcept) | 3.8 |
| HuXBR1-402(3)-G5-PNU (Adc456) | HuXBR1-402(3) (mAb288) | G5-PNU | 50 mM HEPES (pH 7.5), 150 mM NaCl, 1 mM $CaCl_2$, 2% (w/v) Glycerol | PBS without $Ca^{2+}$ and $Mg^{2+}$ (Amimed-Bioconcept) | ND |
| HuXBR1-402(8)-G5-PNU (Adc457) | HuXBR1-402(8) (mAb289) | G5-PNU | 50 mM HEPES (pH 7.5), 150 mM NaCl, 1 mM $CaCl_2$, 2% (w/v) Glycerol | PBS without $Ca^{2+}$ and $Mg^{2+}$ (Amimed-Bioconcept) | ND |
| HuXBR1-402(15)-G5-PNU (Adc458) | HuXBR1-402(15) (mAb290) | G5-PNU | 50 mM HEPES (pH 7.5), 150 mM NaCl, 1 mM $CaCl_2$, 2% (w/v) Glycerol | PBS without $Ca^{2+}$ and $Mg^{2+}$ (Amimed-Bioconcept) | ND |

TABLE 4-continued

Manufacturing conditions and analytical summary of ADCs manufactured in this study. DAR, drug-to-antibody ratio.

| ADC (ref.) | mAb (ref.) | Toxin | Conjugation Buffer | Formulation Buffer | DAR |
|---|---|---|---|---|---|
| HuXBR1-402(17)-G5-PNU (Adc459) | HuXBR1-402(17) (mAb291) | G5-PNU | 50 mM HEPES (pH 7.5), 150 mM NaCl, 1 mM CaCl$_2$, 2% (w/v) Glycerol | PBS without Ca$^{2+}$ and Mg$^{2+}$ (Amimed-Bioconcept) | ND |
| HuXBR1-402(19)-G5-PNU (Adc460) | HuXBR1-402(19) (mAb295) | G5-PNU | 50 mM HEPES (pH 7.5), 150 mM NaCl, 1 mM CaCl$_2$, 2% (w/v) Glycerol | PBS without Ca$^{2+}$ and Mg$^{2+}$ (Amimed-Bioconcept) | ND |
| HuXBR1-402(26)-G5-PNU (Adc461) | HuXBR1-402(26) (mAb296) | G5-PNU | 50 mM HEPES (pH 7.5), 150 mM NaCl, 1 mM CaCl$_2$, 2% (w/v) Glycerol | PBS without Ca$^{2+}$ and Mg$^{2+}$ (Amimed-Bioconcept) | ND |

ND, not determined.

From these analyses it can be concluded that the SMAC-Technology™ conjugation has proceeded at high efficiency resulting in overall average DARs in the range of ca. 3.5 to 4.0 for IgG-format anti-ROR1 antibody-toxin combinations.

Example 11. In Vitro Serum Stability of ROR1-Targeting ADC XBR1-402-G5-PNU

Figure 19:
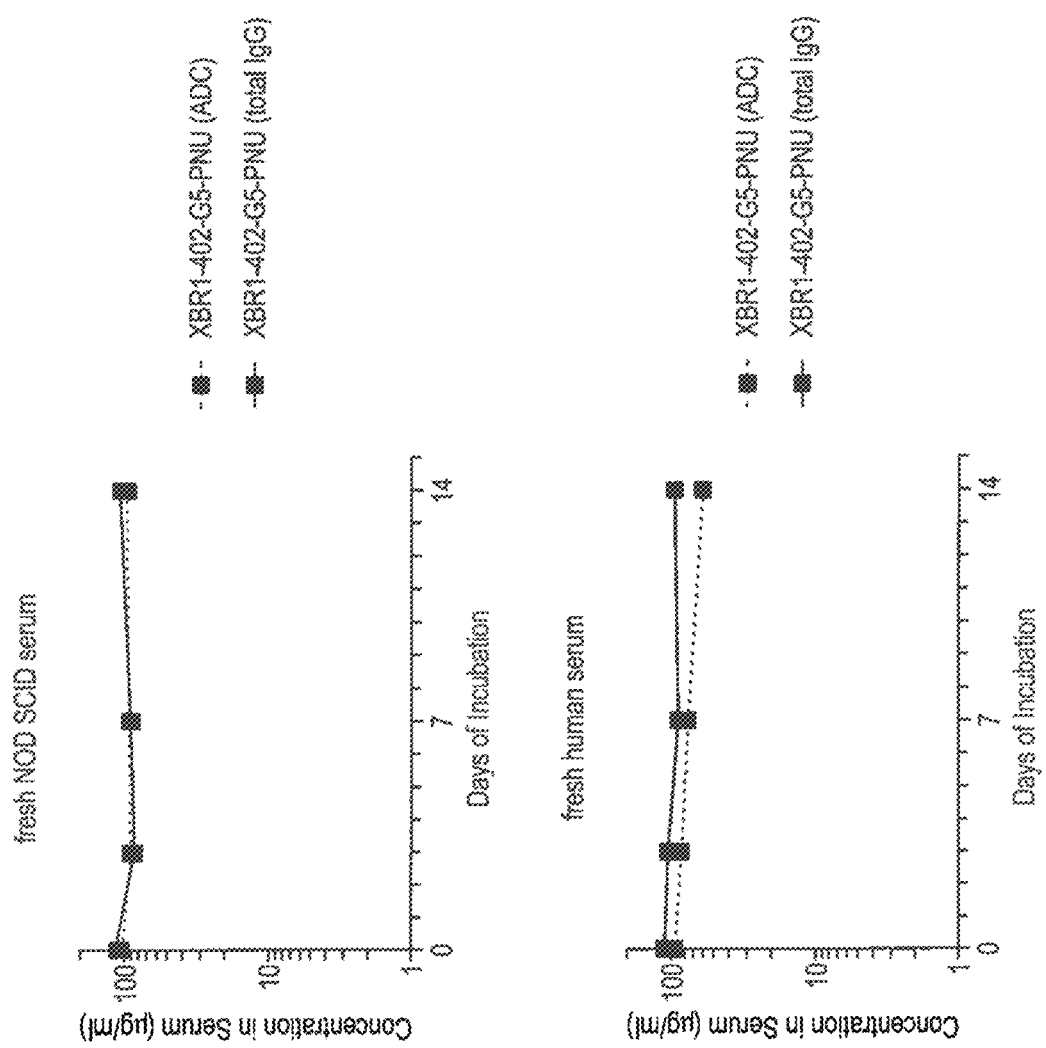
FIG. 19 shows the in vitro stability of the XBR1-402-G5-PNU ADC in NOD SCID mouse serum (panel A) and in human serum (panel B) analyzed by an immune-based ELISA assay detecting either the total antibody (solid line) or the intact ADC (dotted line).

The in vitro serum stability of XBR1-402-G5-PNU was evaluated in an ELISA-based serum stability assay. Briefly, the ADC was diluted to a concentration of 100 μg/mL in NOD SCID mouse (kind gift from Prof. Dr. med. Alfred Zippelius, University Hospital of Basel, Switzerland) and human serum (from the SRK blood donation center, Basel, Switzerland; 50:50 mixture of male:female blood centrifuged 15 min. at 2000 g to obtain serum), and incubated at 37° C. Samples were snap-frozen in liquid nitrogen on days 0, 3, 7 and 14 and stored at −80° C. until ELISA analysis. For mouse serum, dilution series of ADC serum samples (dilution factor 3.5, from 5 to 0.0008 μg/ml) were captured on ELISA plates coated with 2 μg/ml of an in-house developed mouse anti-PNU mAb (generated by immunizing mice with a human IgG-PNU conjugate and screening with a BSA-PNU conjugate) to bind ADC, or with goat anti-human Fc F(ab')2 (Jackson Immunoresearch, 109-006-098) to bind total IgG, and detected with a 1:2500 dilution of an HRP-conjugated donkey anti-human IgG (Jackson Immunoresearch, 709-035-149). For human serum, 2 μg/ml of recombinant human ROR1 (strep-tagged, Example 5) was coated on ELISA plates and a 1:2500 dilution of HRP-conjugated donkey anti-human IgG (Jackson Immunoresearch, 709-035-149) or 2 μg/ml of a mouse anti-PNU IgG (produced in-house) followed by a 1:5000 diluted HRP-conjugated goat anti-mouse Fcγ F(ab')2 (Jackson Immunoresearch, 115-036-071) was used for detection of total IgG and ADC, respectively. Serum concentrations of ADC and total IgGs were calculated from half maximal values of the sample titrations by comparison with a sample of the same ADC of known concentration. As shown in FIG. 19, XBR1-402-G5-PNU remains essentially stable in both sera.

Example 12. In Vitro Cytotoxicity Assays of Anti-ROR1 Antibody-Based ADCs on Wild Type EMT-6 and ROR1-Overexpressing EMT-6 Breast Cancer Cells Cytotoxicity of anti-ROR1 ADC XBR1-402-G5-PNU (adc262) was investigated using wild type (WT) EMT-6 and EMT-6 cells engineered to overexpress human ROR1 (from Example 2). Tras-G5-PNU (adc286) was included as isotype control.

For this, 1×10$^3$ WT EMT-6 and hROR1 overexpressing EMT-6 cells per well were plated on 96-well plates (excluding edge wells, which contained water) in 75 μl DMEM supplemented with 10% by vol. FCS, 100 IU/ml Pen-Strep-Fungizone and 2 mM L-Glutamine and were grown at 37° C. in a humidified incubator at 7.5% CO$_2$ atmosphere. After 1-day incubation, each ADC was added to respective wells in an amount of 25 μl of 3.5-fold serial dilutions in growth medium (resulting in final ADC concentrations from 20 μg/mL to 0.88 ng/ml). After 4 additional days, plates were removed from the incubator and equilibrated to room temperature. After approximately 30 min, 50 μL was removed from each well, and then 50 μl of CellTiter-Glo® 2.0 Luminescent Solution (Promega, G9243) was added to each well. After shaking the plates at 450 rpm for 5 min followed by 10 min incubation without shaking, luminescence was measured on a Tecan Spark 10M plate reader with an integration time of 250 ms per well. Curves of luminescence versus ADC concentration (ng/mL) were fitted with Graphpad Prism Software. The IC50 values, determined using the built-in "log(inhibitor) vs. response—Variable slope (four parameters)" IC$_{50}$ determination function of Prism Software, are reported in Table 5.

TABLE 5

In vitro cell killing of EMT-6 cells (WT and engineered clone 14) by anti-ROR1 or isotype control ADCs (IC=, ng/mL)

| ADC | WT EMT-6 | hROR1-overexpressing EMT-6 |
|---|---|---|
| XBR 1-402-G5-PNU (adc262) | 3.359 | 15 |
| Tras-G5-PNU (adc286) | 4.713 | 4.293 |

Figure 16:
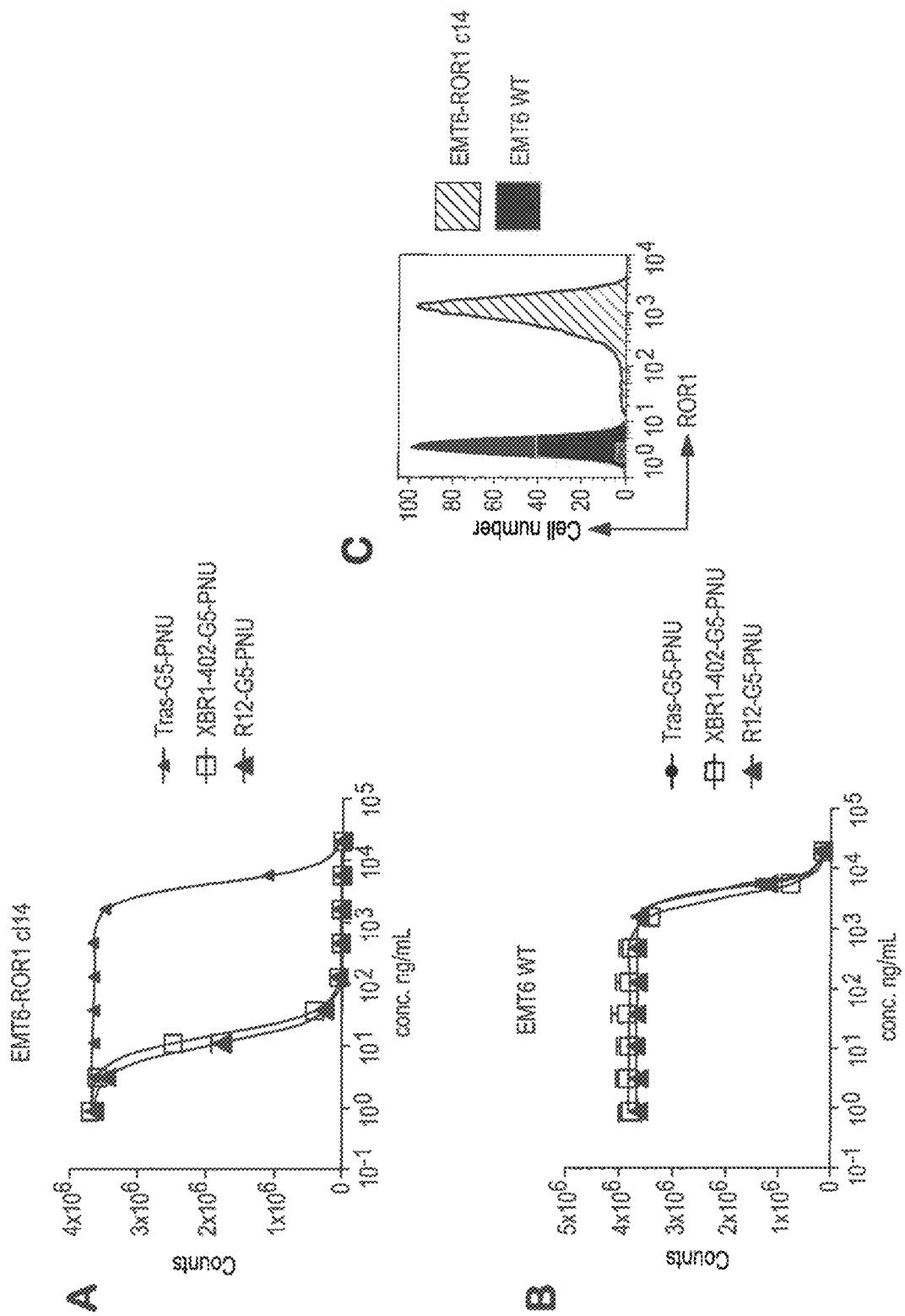
FIG. 16. Panel (A) shows in vitro cell killing of hROR1 transfected mouse breast cancer cell line EMT6-clone14 (abbreviated EMT6-cl14) with site-specifically conjugated PNU-ADCs based on anti-ROR1 antibody R12 and novel antibody XBR1-402, both expressed as chimeric human IgG1 antibodies. A Trastuzumab-G5-PNU ADC, specific for HER2, was used as an isotype-matched control ADC. (B) As a further control the same cell killing experiment with the same ADCs was also performed on the untransfected (and ROR1-negative) EMT6 parental cells. Panel (C) shows the relative expression of hROR1 in hROR1 transfected versus untransfected EMT6 cells as detected by FACS with ROR1-specific antibody 2A2.

FIG. 16 shows the dose-repose curves of the in vitro cell killing assays on WT and hROR1-overexpressing EMT6 cells with the ADCs of Table 5. As per the above Table and FIG. 16, XBR1-402-G5-PNU provides specific killing dependent on ROR1 expression status.

Example 13. In Vitro Cytotoxicity Assays of Novel and Known Anti-ROR1 Antibody-Based ADCs on ROR1-Overexpressing EMT-6 Cells Cytotoxicity of anti-ROR1 ADC XBR1-402-G5-PNU (adc409) was investigated using human EMT-6 cells engineered to overexpress human ROR1 (from Example 2), and compared to an anti-ROR1 ADC based on antibody Ms961 (adc396). Tras-G5-PNU (adc394) was included as isotype control.

For this, $1 \times 10^3$ hROR1 overexpressing EMT-6 cells per well were plated on 96-well plates (excluding edge wells, which contained water) in 75 μL DMEM supplemented with 10% by vol. FCS, 100 IU/ml Pen-Strep-Fungizone and 2 mM L-Glutamine and were grown at 37° C. in a humidified incubator at 7.5% $CO_2$ atmosphere. After 1-day incubation, each ADC was added to respective wells in an amount of 254 of 3.5-fold serial dilutions in growth medium (resulting in final ADC concentrations from 20 μg/mL to 0.88 ng/ml). After 4 additional days, plates were removed from the incubator and equilibrated to room temperature. After approximately 30 min, 50 μL was removed from each well, and then 50 μL of CellTiter-Glo® 2.0 Luminescent Solution (Promega, G9243) was added to each well. After shaking the plates at 450 rpm for 5 min followed by 10 min incubation without shaking, luminescence was measured on a Tecan Spark 10M plate reader with an integration time of 250 ms per well. Curves of luminescence versus ADC concentration (ng/mL) were fitted with Graphpad Prism Software. The IC50 values, determined using the built-in "log(inhibitor) vs. response—Variable slope (four parameters)" $IC_{50}$ determination function of Prism Software, are reported in Table 6.

TABLE 6

In vitro cell killing of engineered EMT-6 cells by inventive and known anti-ROR1 or isotype control ADCs ($IC_{50}$, ng/mL)

| ADC | hROR1-overexpressing EMT-6 |
|---|---|
| XBR1-402-G5-PNU (adc409) | 1.1 |
| Ms961-G5-PNU (adc396) | 11.5 |
| Tras-G5-PNU (adc394) | 3469 |

Figure 17:
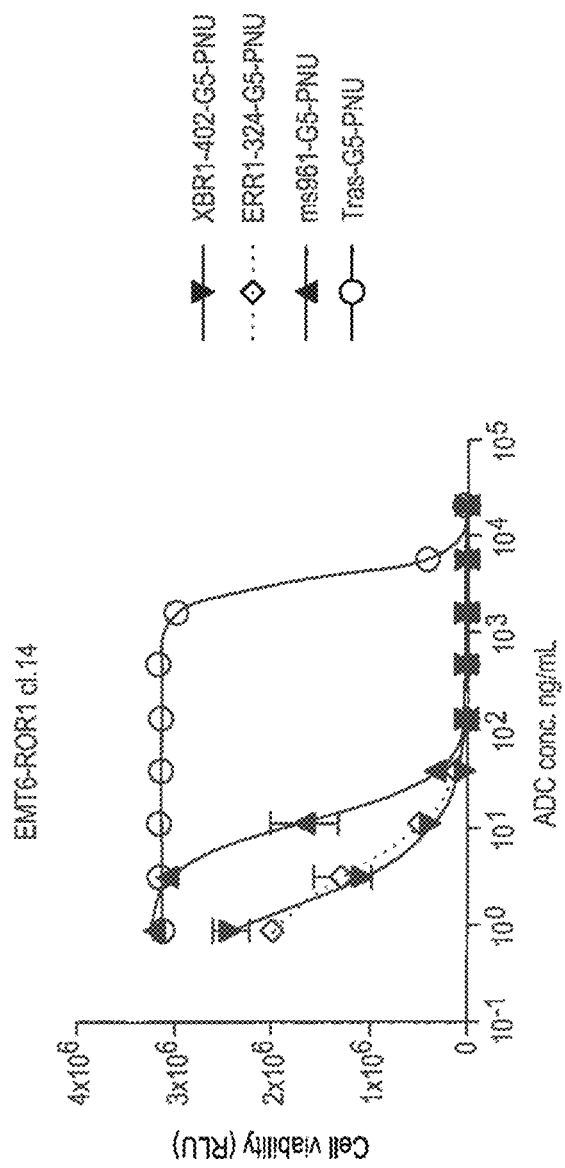
FIG. 17. In vitro cell killing of hROR1 transfected mouse breast cancer cell line EMT6-clone14 (abbreviated EMT6-cl.14) with site-specifically conjugated PNU-ADCs based on anti-ROR1 antibody ms961 and novel antibodies XBR1-402 and ERR1-324, each expressed as chimeric human IgG1 antibodies. A Trastuzumab-G5-PNU ADC, specific for HER2, was used as an isotype-matched control ADC.
Figure 18:
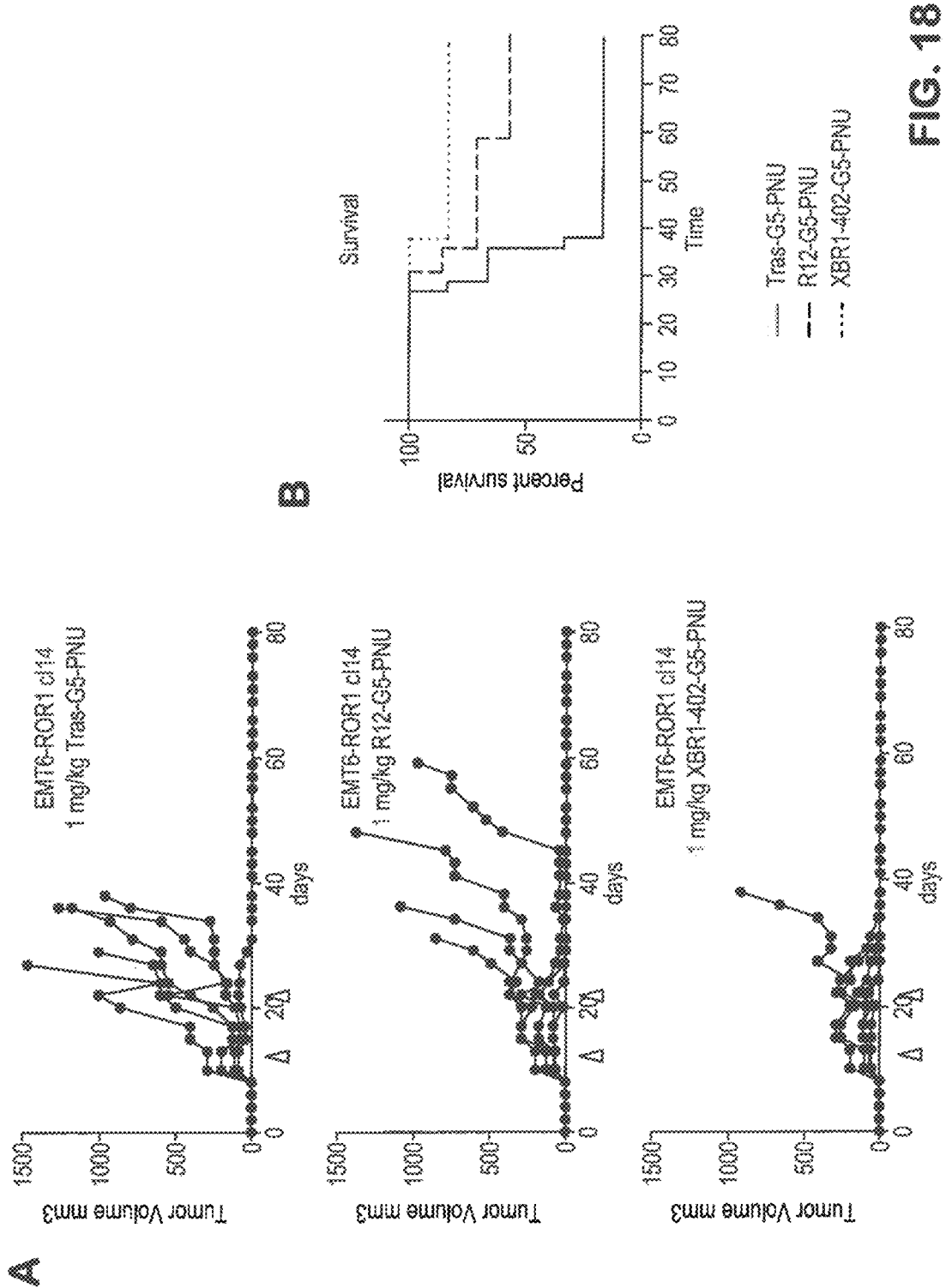
FIG. 18 (A) shows results of an in vivo efficacy study with an orthotopic mouse breast cancer model using hROR1 transfected EMT6 mouse breast cancer cell line that was implanted into the mammary fat pads of Balb/c wild-type mice. The upper panel shows survival curves of mice treated twice with control ADC trastuzumab-G5-PNU. The middle panel shows survival curves of mice treated with PNU-ADC based on anti-ROR1 antibody R12, and the lower panel shows the survival curves of mice treated with PNU-ADC based on novel anti-ROR1 antibody XBR1-402. Little triangles below the x-axis indicate the two treatments with 1 mg/kg of each respective ADC at day 14 and 21 after transplantation of the tumors. (B) shows the Kaplan-Meier Plot of the three experiments displayed in panel (A).

FIG. 17 shows the dose-repose curves of the in vitro cell killing assays on hROR1-overexpressing EMT6 cells with the ADCs of Table 6. As per the above Table and FIG. 17, XBR1-402-G5-PNU provides more potent killing than a comparable ADC based on antibody Ms961.

Example 14. In Vitro Cytotoxicity Assays of Novel and Known Anti-ROR1 Antibody-Based ADCs on Human 697 and Kasumi-2 ALL Cells Cytotoxicity of anti-ROR1 ADC XBR1-402-G5-PNU (adc262) was investigated using human cell line 697, and compared to anti-ROR1 ADCs based on known antibodies 2A2, R11 and R12 (FIG. 13), or by a separate experiment using again 697 and Kasumi-2 ALL cells to 2A2 and R12.

For this, $2.5 \times 10^3$ 697 or Kasumi-2 cells per well were plated on 96-well plates (excluding edge wells, which contained water) in 75 μL RPMI supplemented with 10% by vol. FCS, 100 IU/ml Pen-Strep-Fungizone and 2 mM L-Glutamine and were grown at 37° C. in a humidified incubator at 7.5% $CO_2$ atmosphere. After 1-day incubation, each ADC was added to respective wells in an amount of 254 of 3.5-fold serial dilutions of in growth medium (resulting in final ADC concentrations from 20 μg/mL to 0.88 ng/ml). After 4 additional days, plates were removed from the incubator and equilibrated to room temperature. After approximately 30 min, 50 μL was removed from each well, and then 50 μL of CellTiter-Glo® Luminescent Solution (Promega, G7570) was added to each well. After shaking the plates at 750 rpm for 5 min followed by 20 min incubation without shaking, luminescence was measured on a Tecan Infinity F200 plate reader with an integration time of 1 second per well. Curves of luminescence versus ADC concentration (ng/mL) were fitted with Graphpad Prism Software. The $IC_{50}$ values, determined using the built-in "log (inhibitor) vs. response—Variable slope (four parameters)" $IC_{50}$ determination function of Prism Software, are reported in Table 7.

TABLE 7

In vitro cell killing of 697 cells by anti-ROR1 or isotype control ADCs ($IC_{50}$, ng/mL)

| ADC | 697 |
|---|---|
| 2A2-G5-PNU | 38.0 |
| R11-G5-PNU (adc041) | 469.9 |
| R12-G5-PNU (adc292) | 72.1 |
| XBR1-402-G5-PNU (adc262) | 17.6 |

FIG. 13 shows the dose-repose curves of the in vitro cell killing assays on 697 cells with the ADCs of Table 7. As per the above Table and FIG. 13, ADCs of the invention provide killing of human 697 B cell precursor leukemia cells that is superior to ADCs based on the known anti-ROR1 antibodies.

Example 15. In Vitro Cytotoxicity Assays of Anti-ROR1 Antibody-Based ADCs on Breast Cancer MDA-MB-468 and HS 578T Cells Cytotoxicity of anti-ROR1 ADCs 2A2-G5-PNU (adc165), XBR1-402-G5-PNU (adc135), R12-G5-PNU (adc292), ERR1-Top43-G5-PNU (adc204), and 50:50 by weight mixtures of ERR1-324-G5-PNU (adc202) and 2A2-G5-PNU (adc165), of ERR1-324-G5-PNU (adc202) and XBR1-402-G5-PNU (adc135), of ERR1-324-G5-PNU (adc202) and R12-G5-PNU (adc292), and of ERR1-324-G5-PNU (adc202) and ERR1-Top43-G5-PNU (adc204) was investigated using human cell lines: MDA-MB-468, HS 578T. Ac10-G5-PNU (adc159) was included as isotype control.

For this, the following cells per well were plated on 96-well plates (excluding edge wells, which contained water) and were grown at 37° C. in a humidified incubator at 7.5% $CO_2$ atmosphere in growth medium (DMEM supplemented with 10% by vol. FCS, 100 IU/ml Pen-Strep-Fungizone and 2 mM L-Glutamine).

TABLE 8

Cell plating of Example 17

| Cell type | Cells per well |
|---|---|
| MDA-MD-468 | $6.7 \times 10^4$ |
| HS 578T | $2.7 \times 10^4$ |

After 1-day incubation, each ADC was added to respective wells in an amount of 254 of 3.5-fold serial dilutions in growth medium (resulting in final ADC concentrations from 20 μg/mL to 0.88 ng/ml). After 4 additional days, plates were removed from the incubator and equilibrated to room temperature. After approximately 30 min, 50 μL was removed from each well, and then 50 μL of CellTiter-Glo® 2.0 Luminescent Solution (Promega, G9423) was added to each well. After shaking the plates at 750 rpm for 5 min followed by 20 min incubation without shaking, luminescence was measured on a Tecan Infinity F200 plate reader with an integration time of 1 second per well. Curves of luminescence versus ADC concentration (ng/mL) were fitted with Graphpad Prism Software. The $IC_{50}$ values, determined using the built-in "log(inhibitor) vs. response—Variable slope (four parameters)" $IC_{50}$ determination function of Prism Software, are reported in Table 9.

TABLE 9

In vitro cell killing of various human cancer cells by anti-ROR1 ADCs as well as an isotype control (IC50 values are provided in ng/mL)

| | ADC/Cell type | |
|---|---|---|
| hROR1 status | MDA-MD-468 positive | HS 578T positive |
| 2A2-G5-PNU (adc165) | 456 | 1,784 |
| XBR1-402-G5-PNU (adc135) | ND | 1,403 |
| R12-G5-PNU (adc292) | 349 | 3,498 |
| ERR1-Top43-G5-PNU (adc204) | 143 | 707 |
| Ac10-G5-PNU (adc159) | 3,593 | 8,408 |

Figure 12:
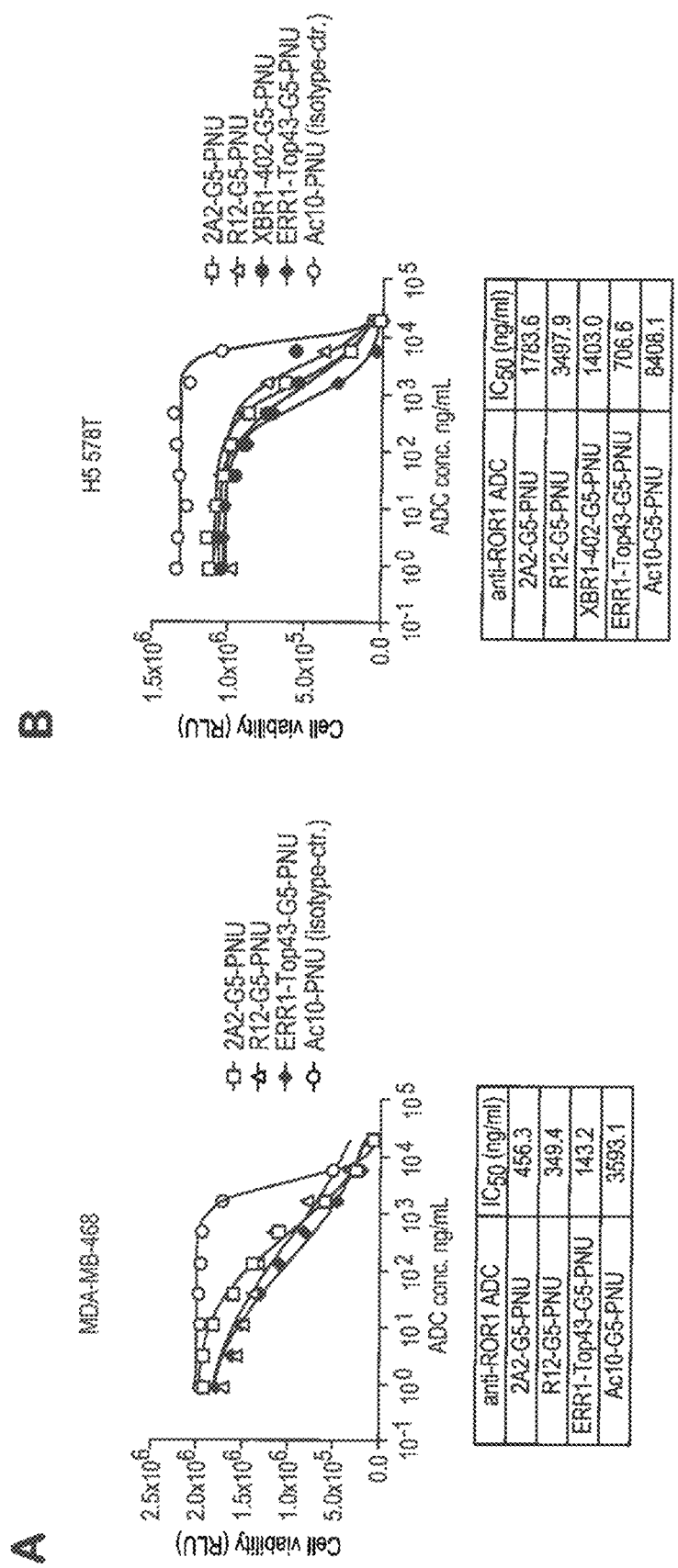
FIG. 12 shows the efficacy for in vitro cell killing assays performed on (panel A) immortalized human breast cancer cell line MDA-MB-468 with known hROR1-targeting ADCs (2A2-G5-PNU, R12-G5-PNU) and a novel ADC provided in the invention (ERR1-Top43-G5-PNU), and (panel B) immortalized human breast cancer cell line HS 578T with known hROR1-targeting ADCs (2A2-G5-PNU, R12-G5-PNU) and novel ADCs provided in the invention (XBR1-402-G5-PNU and ERR1-Top43-G5-PNU). CD30 targeting ADC Ac10-G5-PNU was used as an isotype-matched control ADC in both panels.

FIG. 12 shows the dose-repose curves of the in vitro cell killing assays on MDA-MB-468 and HS 578T cells with the ADCs of Table 9. As per the above Table and FIG. 12, selected ADCs of the invention provides killing of certain human cancer cells that is superior to the known anti-ROR1 antibodies 2A2 and R12.

Example 16. In Vitro Cytotoxicity Assays of Humanized Anti-ROR1 Antibody-Based ADCs on 697 Cells Cytotoxicity of humanized anti-ROR1 ADCs huXBR1-402-3-G5-PNU (adc456), huXBR1-402-8-G5-PNU (adc457), huXBR1-402-15-G5-PNU (adc458), huXBR1-402-17-G5-PNU (adc459), huXBR1-402-19-G5-PNU (adc460) and huXBR1-402-26-G5-PNU (adc461) was investigated using human 697 cells. Tras-G5-PNU (adc286) was included as isotype control.

For this, $5 \times 10^4$ 697 cells per well were plated on 96-well plates (excluding edge wells, which contained water) in 75 μL RPMI supplemented with 10% by vol. FCS, 100 IU/ml Pen-Strep-Fungizone and 2 mM L-Glutamine and were grown at 37° C. in a humidified incubator at 7.5% $CO_2$ atmosphere. After 1-day incubation, each ADC was added in duplicate to respective wells in an amount of 254 of 3.5-fold serial dilutions in growth medium (resulting in final ADC concentrations from 20 μg/mL to 0.88 ng/ml). After 4 additional days, plates were removed from the incubator and equilibrated to room temperature. After approximately 30 min, 50 μL was removed from each well, and then 50 μL of CellTiter-Glo® 2.0 Luminescent Solution (Promega, G9243) was added to each well. After shaking the plates at 450 rpm for 5 min followed by 10 min incubation without shaking, luminescence was measured on a Tecan Spark 10M plate reader with an integration time of 250 ms per well. Curves of luminescence versus ADC concentration (ng/mL) were fitted with Graphpad Prism Software. The $IC_{50}$ values, determined using the built-in "log(inhibitor) vs. response—Variable slope (four parameters)" $IC_{50}$ determination function of Prism Software, are reported in Table 10.

TABLE 10

In vitro cell killing of 697 cells by non-humanized and humanized anti-ROR1 or isotype control ADCs ($IC_{50}$, ng/mL)

| ADC | $IC_{50}$ values on 697 cells (ng/ml) |
|---|---|
| XBR1-402-G5-PNU (adc394) | 211.6 |
| HuXBR1-402(3)-G5-PNU (Adc456) | 98.1 |
| HuXBR1-402(8)-G5-PNU (Adc457) | 164.2 |
| HuXBR1-402(15)-G5-PNU (Adc458) | 105.6 |
| HuXBR1-402(17)-G5-PNU (Adc459) | 70.6 |
| HuXBR1-402(19)-G5-PNU (Adc460) | 91.7 |
| HuXBR1-402(26)-G5-PNU (Adc461) | 93.9 |
| Tras-G5-PNU (Adc286) | 5214 |

FIG. 25 shows the dose-repose curves of the in vitro cell killing assays on 697 cells with the humanized ADCs of Table 10. As per the above Table and FIG. 25, the humanized ADCs are more potent compared to ADCs manufactured with the parental, non-humanized mAb.

Example 17. In Vivo Pharmacokinetic Study of the Anti-ROR1 XBR1-402 Antibody and XBR1-402-G5-PNU ADC in CD-1 Wild-Type Mouse Strain The following study was performed at ABPRO (Burlington, Mass., USA). Female CD-1 mice (at least 6-weeks of age at study start, from Taconic Biosciences, Germantown, N.Y., USA), housed in groups of up to 5 animals per cage, were randomized by weight into two groups of 9 animals each. One group received, by intravenous administration, a single dose of 1 mg/kg of XBR1-402 (mAb202), while the second group received a single dose of 1 mg/kg of XBR1-402-G5-PNU (adc409). Post-dose blood samples were collected according to the protocol of Table 11 from subgroups consisting of 3 animals each. Blood sampling proceeded by lancet puncture of the submandibular vein (collecting approximately 200 μL), with the exception of the sampling at 21 days, which was by cardiac puncture (collecting approximately 600 μL). Samples from subgroups were pooled for each time point. Plasma was isolated by blood centrifugation at 1'500 g for 10 min., and stored in sterile cryovials at −80° C. until in-house analysis by ELISA.

TABLE 11

Pharmacokinetic study blood sampling protocol

| Treatment group (no. of animals) | Subgroup (no. of animals) | Blood samplings post dose |
|---|---|---|
| 1 mg/kg XBR1-402 (9) | 1 (3) | 1 h, 7 days |
| | 2 (3) | 24 h, 14 days |
| | 3 (3) | 3 days, 21 days (terminal bleed) |
| 1 mg/kg XBR1-402-G5-PNU (9) | 1 (3) | 1 h, 7 days |
| | 2 (3) | 24 h, 14 days |
| | 3 (3) | 3 days, 21 days (terminal bleed) |

Plasma was isolated from blood by centrifugation at 1500 g for 10 min, and transferred to sterile cryovials for storage at −80° C. until analysis by ELISA. The in vivo stability of mAb XBR1-402 and of ADC XBR1-402-G5-PNU was evaluated by an ELISA-based assay. Dilution series of ADC serum samples were captured on ELISA plates coated with 2 μg/ml of a mouse anti-PNU mAb (produced in-house by immunizing mice with a human IgG-PNU conjugate and screening with a BSA-PNU conjugate) to bind ADC, or with anti-human Fc F(ab')2 (Jackson Immunoresearch) to bind total IgG, and detected with a 1:2500 dilution of an HRP-conjugated anti-human IgG F(ab')2 (Jackson Immunoresearch). Serum concentrations of ADC and total IgGs were calculated from half maximal values of the sample titrations by comparison with a sample of the same ADC of known concentration.

Figure 20:
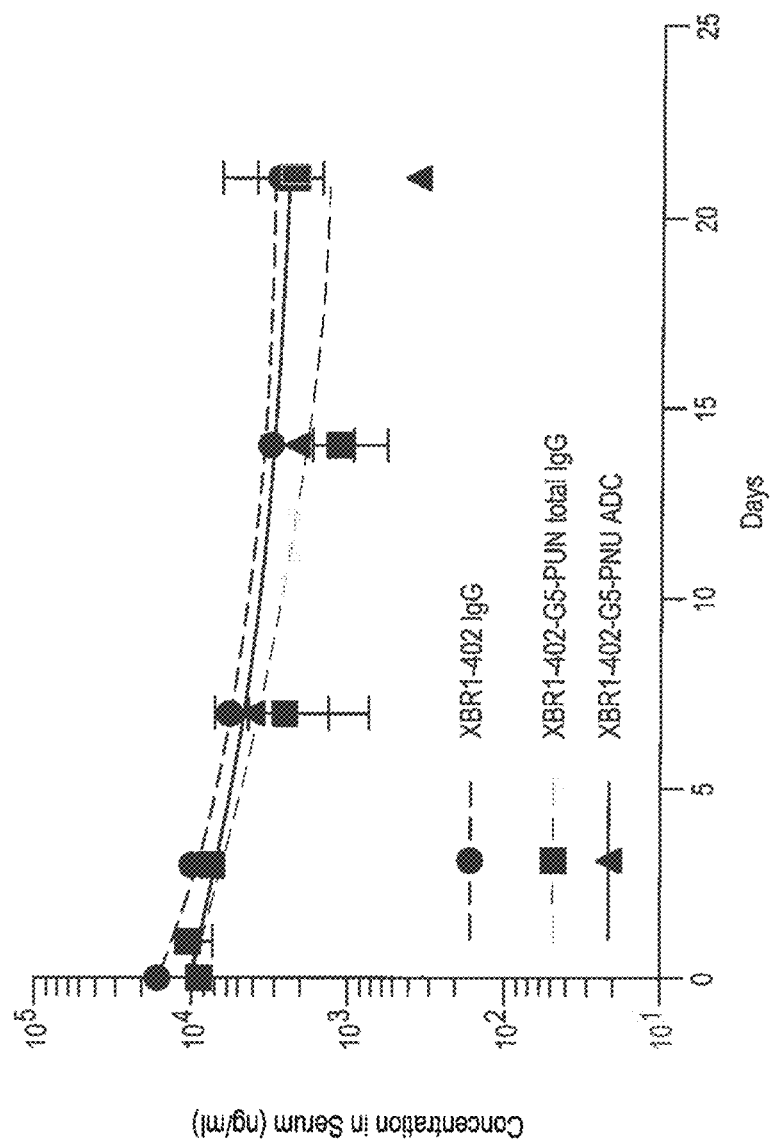
FIG. 20 shows the in vivo plasma stability of novel naked anti-ROR1 antibody XBR1-402, as well as of XBR1-402-G5-PNU ADC evaluated in female CD-1 mice. Depicted are plasma stability measured by immune-based ELISA assay of total IgG detected with a human Fc detection reagent as well as of intact ADC detected with a PNU-specific detection reagent.

The data in FIG. 20 shows the high stability of the ADC of the invention.

Example 18. Evaluation of In Vivo Potency of ADCs in a Disseminated Xenograft Model of Human Acute Lymphocytic Leukemia (ALL) Cell Line 697 in NOD-SCID Mice The following study was performed at Pipeline Biotech (Trige, Denmark). The efficacy of XBR1-402-G5-PNU (adc288) and humanized hu2A2-G5-PNU (adc287; based on unpublished PCT/EP2016/076244) was compared in a disseminated xenograft model in female NOD-SCID mice injected with hROR1 positive 697 ALL cells. An ADC based in HER2 specific anti body Trastuzumab, Tras-G5-PNU (adc286) served as a negative isotype-matched control ADC.

9-week old mice, each weighing at least 20 g, were inoculated with 697 tumor cells ($5\times10^6$ cell/animal, in 200 µL PBS) on study day 0. Each ADC, formulated in PBS, was administered (i.v.) to a group of 6 mice at 1.0 mg/kg on days 7, 14 and 21, with administration of mouse IgG (Jackson ImmunoResearch, 015-000-003), 30 mg/kg) 20 hours before each ADC administration. Any animal showing clinical signs of moderate pain, moderate distress, any degree of suffering, or any clinical signs exceeding the limits of the study specific humane endpoints, according to the European and Danish legislation on animals in experimental studies, was euthanized. Blood (904 in EDTA vials) was collected from the tail vein each animal on days 12 and 19. Plasma was isolated by blood centrifugation according to standard procedures. Samples from treatment groups were pooled for each time point.

Dilution series of ADC plasma samples were captured on ELISA plates coated with 2 µg/ml of a mouse anti-PNU mAb (produced in-house by immunizing mice with a human IgG-PNU conjugate and screening with a BSA-PNU conjugate) to bind ADC, or with anti-human Fc F(ab')2 (Jackson Immunoresearch, 109-006-098) to bind total IgG, and detected with a 1:2500 dilution of an HRP-conjugated anti-human IgG F(ab')2 (Jackson Immunoresearch, 709-035-149). Serum concentrations of ADC and total IgGs were calculated from half maximal values of the sample titrations by comparison with a sample of the same ADC of known concentration.

Data analysis was performed using the software PRISM. Mice treated with the inventive XBR1-402-G5-PNU ADC showed prolonged survival relative to those treated with comparable ROR1-targeting hu2A2-G5-PNU ADC, or with isotype control ADC (FIG. 15, panel A). Moreover, the concentration of XBR1-402-G5-PNU ADC remains higher in plasma than the known or isotype control ADC (FIG. 15, panel B).

Example 19. Evaluation of In Vivo Efficacy of Anti-ROR1 ADCs in Orthotopic Breast Cancer Models Established with hROR1-Overexpressing EMT-6 Cells ADC based on novel anti-ROR1 antibody XBR1-402-G5-PNU (adc262) was compared to R12-G5-PNU (adc327), an ADC based on known antibody R12 and isotype control Tras-G5-PNU (adc286) ADCs in the following mouse model according to the study protocol of Table 13.

TABLE 12

Orthotopic breast cancer models used for evaluation of ADCs

| Model | Mouse Strain and Sex | Tumor Establishment |
| --- | --- | --- |
| hROR1-overexpressing EMT-6, clone 14 (from Example 2) | Syngeneic female BALB/c mice, implantation at 4-8 weeks of age | Injection of $1 \times 10^6$ cells into the mammary fat pads. Tumor volume at randomization from 100-150 mm$^3$ |

TABLE 13

Protocols used for evaluation of anti-ROR1 XBR1-402-G5-PNU ADC in orthotopic breast cancer models with orthotopically implanted EMT6 cells overexpressing ROR1 (clone (cl 14))

| Group | No. of Mice | Total Dose | Dosing Days post implantation | Route |
| --- | --- | --- | --- | --- |
| 1 (Tras-G5-PNU, adc286) | 6 | 1 mg/kg/day of Tras-G5-PNU (in PBS) | 14, 21, 28 | Intravenous |
| 2 (XBR1-402-G5-PNU, adc409) | 6 | 1 mg/kg/day of XBR1-402-G5-PNU (in PBS) | 14, 21, 28 | Intravenous |
| 3 (R12-G5-PNU, adc327) | 6 | 1 mg/kg/day of R12-G5-PNU (in PBS) | 14, 21, 28 | Intravenous |

FIG. 18 shows the tumor volume evolving over the study in each of the 6 individual mice. Orthotopic breast cancer models established with breast cancer cells having high hROR1 expression respond significantly to treatment with the ADC of the invention, as opposed to the non-response of the ROR1-negative WT EMT-6 model. The remarkable response of the ADC of the invention moreover demonstrates a significant improvement over a comparable ADC based on the known R12 ROR1-targeting antibody.

Example 20. Analysis of hROR1 Expression in Human Patient Derived Tumor Lysates by Western Blot Tumor lysates of human patient-derived xenograft (PDX) models (Charles River, Freiburg, Germany) and lysate of a highly ROR1-positive immortalized cell line (Kasumi-2) as a control, as well as lysate from immortalized A549 cancer cells, were probed for hROR1 protein expression by Western blot. For this, lysates were denatured by mixing with 5×SDS-PAGE loading buffer (250 mM Tris-HCl pH 6.8, 10% SDS, 30% Glycerol, 5% µ-mercaptoethanol) and heating to 99° C. for 5 min. After separation by SDS-PAGE, proteins were transferred to PVDF membranes using an eblot transfer System (Genscript). Membranes were then incubated at 4° C. overnight with commercially available polyclonal rabbit anti-ROR1 antibody 4102 (Cell Signaling Technology, Danvers, USA) diluted 1:200 in TBST (20 mM Tris-HCl, 150 mM NaCl, pH 7.6, 0.1% Tween-20) containing 10% horse serum (Amimed, Bioconcept, Switzerland). After two washes with TBST, membranes were incubated with HRP-coupled anti-rabbit secondary antibodies (WesternSure HRP goat-anti-rabbit IgG, LiCor, Lincoln, USA) for 1 hour at room temperature. Signals were revealed by incubating membranes in luminescent substrate (SuperSignal West Femto (34094, Thermo Fisher) and imaging using a cDigit Western blot reader (LiCor, Lincoln, USA). Detection of the housekeeping gene GAPDH served as a loading control.

TABLE 14

Tumor lysate hROR1 status of Example 22

| Tumor Designation | Tumor Origin | hROR1 status |
|---|---|---|
| PXF 1118 | lung, peuramesothelioma | +++ |
| RXF 486 | kidney tumor, hypernephroma | + |
| PXF 541 | lung, peuramesothelioma | +++ |
| SXFS 1407 | soft tissue sarcoma, neurofibrosarcoma | ++ |
| CX 533 | colon cancer, adenocarcinoma | + |
| Kasumi-2 | B cell precursor leukemia | +++ |
| A549 | lung carcinoma | + |

Figure 21:
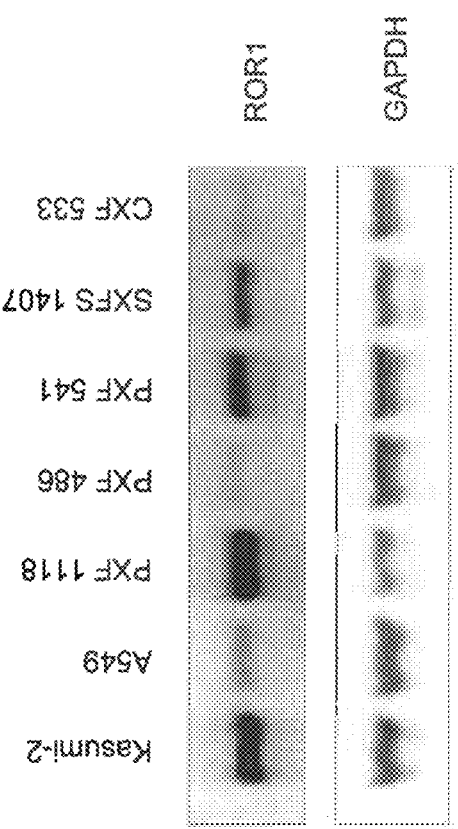
FIG. 21 shows the analysis of different patient derived tumor lysates for hROR1 protein expression by Western-Blot analysis, including lysates from two control cell lines Kasumi-2 (human ALL cell line) and A549 (human lung cancer cell line). The patient-derived tumor lysates are of the following designation and origin: PXF 1118: pleuramesothelioma, RXF 486: hypernephroma, PXF 541, pleuramesothelioma, SXFS 1407: neurofibrosarcoma, CXF 533: adenocarcinoma.

FIG. 21 shows the Western Blot analysis of human tumor lysates, as well as lysates from immortalized cancer cells.

Example 21. Analysis of In Vivo Efficacy of ADC XBR1-402-G5-PNU in Patient-Derived Tumor Xenograft Models The following study was performed at Charles River (at Oncotest GmbH, Freiburg, Germany).

TABLE 15

Patient-derived tumor xenograft models used for evaluation of anti-ROR1 XBR1-402-G5-PNU ADC

| Model | Mouse Strain and Sex | Tumor Establishment |
|---|---|---|
| PXF 1118 (lung, peuramesothelioma), unilateral | Female NMRI nude mice, implantation at 5-7 weeks of age | Tumor implantation unilateral or bilateral, and subcutaneous. Tumor volume at randomization from 50-250 mm³ |
| RXF 486 (kidney tumor, hypernephroma) | | |
| PXF 541 (lung, peuramesothelioma) | | |
| SXFS 1407 (soft tissue sarcoma, neurofibrosarcoma) | | |
| CX 533 (colon cancer, adenocarcinoma) | | |

The XBR1-402-G5-PNU (adc409) ADC, previously confirmed to be endotoxin-free, was investigated in each model according to the following study protocol:

TABLE 16

Protocols used for evaluation of anti-ROR1 XBR1-402-G5-PNU ADC in patient derived tumor xenograft models

| Group | No. of Mice | Total Daily Dose | Dosing Days | Route |
|---|---|---|---|---|
| 1 (vehicle control) | 3 | 10 ml/kg/day of PBS | 0, 8. 15 | Intravenous |
| 2 (XBR1-402-G5-PNU, adc409) | 3 | 1 mg/kg/day of XBR1-402-G5-PNU (in PBS) | 0, 8. 15 | Intravenous |

Mice were subcutaneously implanted with PDX material (either one-sided (PXF 111, RXF 486, CX 533) or bilaterally (SXFS 1407, PXF 541). Mice were randomized when tumors reached a size of 100 cm³ and were treated with ADC at 1 mg/kg or vehicle for a total of 3 times. Tumor volumes were determined by caliper measurement and body weight was recorded twice weekly. Mice were euthanized on reaching a tumor burden of 2000 mm³ (unilateral) or 1700 mm³ (bilateral), or on significant body weight loss (overall more than 30%, or more than 20% in two days).

FIG. 22 shows the tumor volume evolution over the study. Tumor xenografts established with patient-derived tumor material having high hROR1 expression respond significantly to treatment with the ADC of the invention.

Example 22. In Vitro Activity of XBR1-402 CAR-T

CAR-T cells based on XBR1-402 were engineered using methods previously described for ROR1-targeting mAbs R11 and R12 (Hudecek, M., Lupo-Stanghellini, M. T., Kosasih, P. L., Sommermeyer, D., Jensen, M. C., Rader, C., and Riddell, S. R. (2013) Receptor affinity and extracellular domain modifications affect tumor recognition by ROR1-specific chimeric antigen receptor T cells. Clin. Cancer Res. 19, 3153-3164). Ex vivo expanded primary human CD8⁺ CD62L⁺ T cells were lentivirally transduced with XBR1-402 or R12-derived CARs containing CD3ζ and 4-1BB signaling domains and a short spacer. Transduced T cells were purified via tEGFR by FACS and their phenotype was assesed the day before functional assays. CD8+ purity varied between 97% and 99%, tEGFR expression varied between 95% and 99%. Following 72 h co-culture with ROR1-positive or ROR1-negative human breast cancer cells, CFSE-stained CD8+CD62L+ cells were analyzed by flow cytometry, revealing target-dependent proliferation of XBR1-402 and R12 CAR-T (FIG. 26; upper left panel). IFNγ and IL2 concentrations in the supernatant taken after 24 h of co-culture were measured by ELISA (FIG. 26; upper right panel). Selective cytotoxicity was measured with a luciferase-based cytotoxicity assay following 11 h of co-culture with ROR1-positive and ROR1-negative cells (FIG. 26; lower panel).

The same experiments were repeated to compare XBR1-402 CAR-T with a short spacer to XBR1-402 CAR-T with a long spacer. Following 72 h co-culture with ROR1-positive or ROR1-negative human breast cancer cells, CFSE-stained CD8+CD62L+ cells were analyzed by flow cytometry, revealing stronger proliferation of the XBR1-402 CAR-T with the short spacer (FIG. 27; upper panel). Selective cytotoxicity with the luciferase-based cytotoxicity assay following 11 h of co-culture with ROR1-positive and ROR1-negative cells revealed selective cytotoxicity for both XBR1-402 CAR-Ts with short and long spacer (FIG. 27; lower panel).

Example 23. Specificity Analysis of XBR1-402

Figure 28:
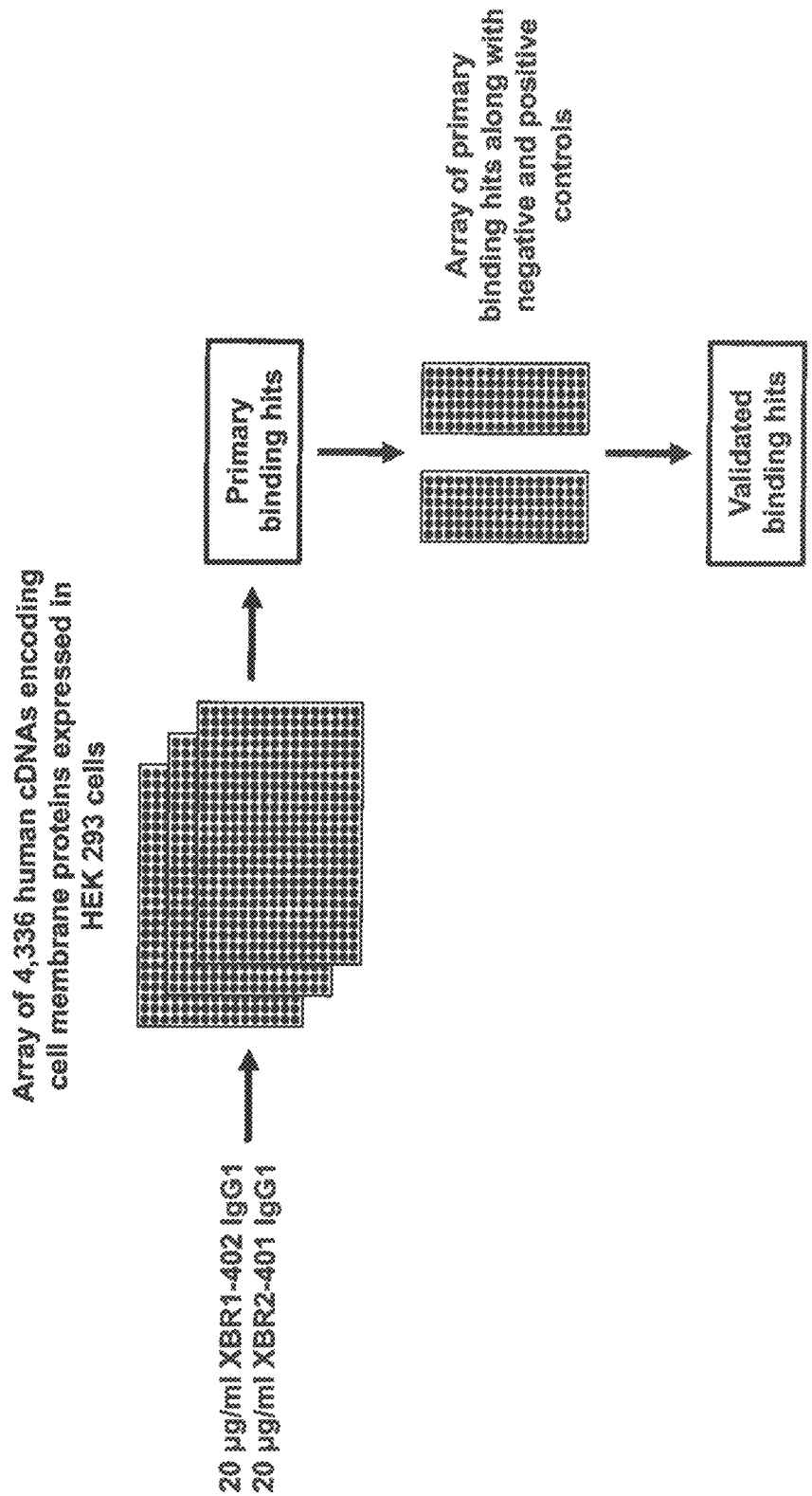
FIG. 28 provides an overview of the specificity analysis of chimeric rabbit/human anti-human ROR1 IgG1 XBR1-402 and, as a control, chimeric rabbit/human anti-human ROR2 IgG1 XBR2-401, with the Retrogenix Cell Microarray Platform.
Figure 29:
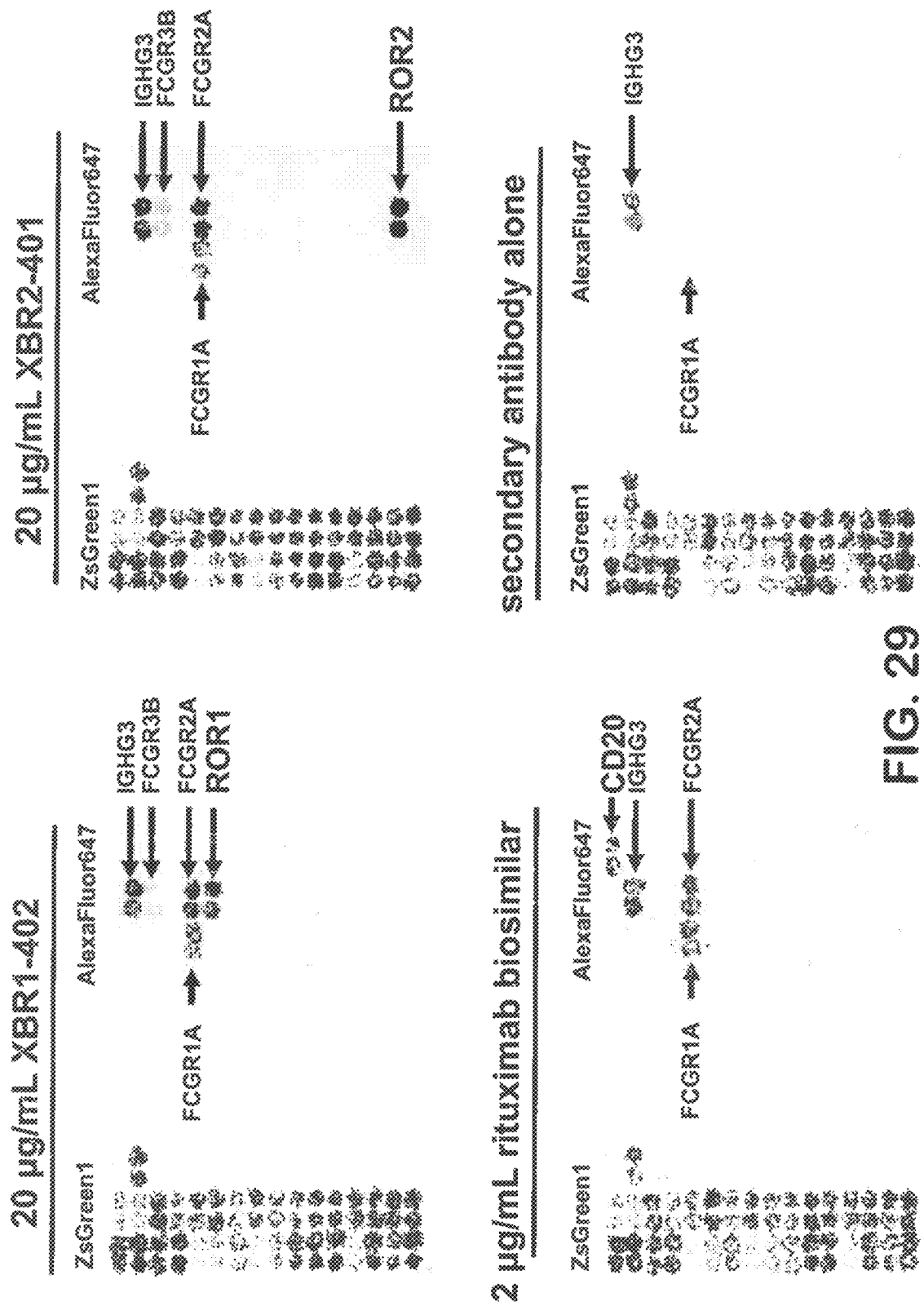
FIG. 29 shows a specificity analysis of chimeric rabbit/human anti-human ROR1 IgG1 XBR1-402 and, as a control, chimeric rabbit/human anti-human ROR2 IgG1 XBR2-401, with the Retrogenix Cell Microarray Platform. Primary binding hits from the large screen involving 4,336 human plasma membrane proteins (see FIG. 28) were combined on a single slide and stained with chimeric rabbit/human anti-human ROR1 IgG1 XBR1-402 and, as controls, chimeric rabbit/human anti-human ROR2 IgG1 XBR2-401 and a rituximab biosimilar. ZsGreenl signals on the left indicate the expression levels of the various human membrane proteins. In addition to their respective antigens (ROR1, ROR2, and CD20), the tested antibodies in IgG1 format also bind to Fcγ receptors FCGR3B (CD16B), FCGR1A (CD64A), and FCGR2A (CD32A) as expected. Staining with the secondary antibody alone detects the human IgG3 heavy chain (IGHG3) as expected.

FIG. 28 provides an overview of the Retrogenix Cell Microarray Platform. Primary screen: Purified chimeric rabbit/human IgG1 XBR1-402 and purified chimeric rabbit/human IgG1 XBR2-401 were pooled to a concentration of 2 µg/mL each. The pool was screened for binding against fixed HEK293 cells/slides expressing 4,336 human plasma membrane proteins individually (13 slide sets; n=2 slides per slide set). All transfection efficiencies exceeded the minimum threshold. An AlexaFluor647 anti-human IgG Fc detection antibody was used. Primary hits (duplicate spots) were identified by analyzing fluorescence (AlexaFluor647 and ZsGreenl) on ImageQuant. Vectors encoding all hits were sequenced to confirm their correct identities. Confirmation screen: Vectors encoding all hits, plus control vectors, were spotted in duplicate on new slides, and used to reverse transfect human HEK293 cells as before. All transfection efficiencies exceeded the minimum threshold. Identical fixed slides were treated with each of the two test antibodies (XBR1-402 and XBR2-401) individually, plus positive and negative controls (n=2 slides per treatment). Slides were analyzed as before (FIG. 29).

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, GenBank sequences, patents, and patent applications cited in this specification are herein incorporated by reference as if each was specifically and individually indicated to be incorporated by reference.

We claim:

1. An antibody, antibody-based binding protein or antibody fragment that specifically binds to the extracellular domain of human receptor tyrosine kinase-like orphan receptor 1 (ROR1), comprising the HCDR1, HCDR2 and HCDR3 sequences and LCDR1, LCDR2 and LCDR3 sequences of SEQ ID NO: 27 (HCDR1), SEQ ID NO: 28 (HCDR2), SEQ ID NO: 29 (HCDR3), SEQ ID NO: 66 (LCDR1), SEQ ID NO: 67 (LCDR2) and SEQ ID NO: 68 (LCDR3).

2. The antibody, antibody-based binding protein or antibody fragment of claim 1, wherein the antibody, antibody-based binding protein or antibody fragment is humanized.

3. A pharmaceutical composition comprising (1) a therapeutically effective amount of the antibody, antibody-based binding protein or antibody fragment of claim 1 and (2) a pharmaceutically acceptable carrier.

4. A method of treating a disease or condition associated with elevated expression of ROR1 in a subject, comprising administering the pharmaceutical composition of claim 3 to a subject having a disease or condition associated with elevated expression of ROR1, thereby treating the disease or condition associated with elevated expression of ROR1 in the subject.

5. A polynucleotide encoding an antibody, antibody-based binding protein or antibody fragment comprising the HCDR1, HCDR2 and HCDR3 sequences and LCDR1, LCDR2 and LCDR3 sequences of SEQ ID NO: 27 (HCDR1), SEQ ID NO: 28 (HCDR2), SEQ ID NO: 29 (HCDR3), SEQ ID NO: 66 (LCDR1), SEQ ID NO: 67 (LCDR2) and SEQ ID NO: 68 (LCDR3).

6. An antibody drug conjugate (ADC), comprising an antibody, antibody-based binding protein or antibody fragment that specifically binds to the extracellular domain of human receptor tyrosine kinase-like orphan receptor 1 (ROR1), comprising the heavy HCDR1, HCDR2 and HCDR3 sequences and LCDR1, LCDR2 and LCDR3 sequences of SEQ ID NO: 27 (HCDR1), SEQ ID NO: 28 (HCDR2), SEQ ID NO: 29 (HCDR3), SEQ ID NO: 66 (LCDR1), SEQ ID NO: 67 (LCDR2) and SEQ ID NO: 68 (LCDR3), and at least one cytotoxic agent.

7. The antibody drug conjugate of claim 6, wherein the cytotoxic agent is a small molecular weight toxin, a peptide toxin, or a protein toxin.

8. The antibody drug conjugate of claim 6, wherein the antibody or antibody fragment is conjugated to the cytotoxic agent via sortase enzyme mediated antibody conjugation (SMAC).

9. The antibody drug conjugate of claim 6, wherein the cytotoxic agent is anthracycline (PNU) toxin derivative $Gly_{(n)}$-EDA-PNU, where n is any number from 1 to 21.

10. The ADC of claim 6, wherein the antibody, antibody-based binding protein or antibody fragment is humanized.

11. A pharmaceutical composition comprising (1) antibody drug conjugate of claim 6 and (2) a pharmaceutically acceptable carrier.

12. A method of treating a disease or condition associated with elevated expression of ROR1 in a subject, comprising administering the pharmaceutical composition of claim 11 to a subject having a disease or condition associated with elevated expression of ROR1, thereby treating the disease or condition associated with elevated expression of ROR1 in the subject.

* * * * *